(12) United States Patent
Kawaida et al.

(10) Patent No.: US 9,403,909 B2
(45) Date of Patent: Aug. 2, 2016

(54) ANTI-MST1R ANTIBODIES AND USES THEREOF

(75) Inventors: Reimi Kawaida, Tokyo (JP); Toshiaki Ohtsuka, Tokyo (JP); Toshinori Agatsuma, Tokyo (JP); Philip Rodley, Tokyo (JP); Sandra Miller, Munich (DE); Ulrike Schubert, Munich (DE)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 1262 days.

(21) Appl. No.: 13/206,736

(22) Filed: Aug. 10, 2011

(65) Prior Publication Data

US 2012/0034215 A1 Feb. 9, 2012

Related U.S. Application Data

(63) Continuation of application No. PCT/JP2010/052479, filed on Feb. 10, 2010.

(60) Provisional application No. 61/151,411, filed on Feb. 10, 2009.

(51) Int. Cl.
*A61K 39/395* (2006.01)
*C07K 16/28* (2006.01)
*A61K 39/00* (2006.01)

(52) U.S. Cl.
CPC ........ *C07K 16/2863* (2013.01); *A61K 39/39558* (2013.01); *A61K 2039/505* (2013.01); *C07K 2317/21* (2013.01); *C07K 2317/24* (2013.01); *C07K 2317/33* (2013.01); *C07K 2317/55* (2013.01); *C07K 2317/565* (2013.01); *G01N 2333/9121* (2013.01)

(58) Field of Classification Search
CPC .................... A61K 39/39558; A61K 2039/505
USPC ............................... 530/387.1, 387.3, 388.22
See application file for complete search history.

(56) References Cited

U.S. PATENT DOCUMENTS

| | | | |
|---|---|---|---|
| 6,300,064 B1 | 10/2001 | Knappik et al. | |
| 8,133,489 B2 * | 3/2012 | Pereira et al. | 424/145.1 |
| 2009/0246205 A1 | 10/2009 | Pereira et al. | |

FOREIGN PATENT DOCUMENTS

| | | |
|---|---|---|
| JP | 2008-508858 A | 3/2008 |
| WO | WO 01/05950 | 1/2001 |
| WO | WO 2006/020258 | 2/2006 |
| WO | WO 2009/094148 | 7/2009 |

OTHER PUBLICATIONS

Montero-Julian et al. (Hybridoma. Dec. 1998; 17 (6): 541-51).*
O'Toole et al. (Cancer Res. Sep. 15, 2006; 66 (18): 9162-70).*
Holm et al. (Mol. Immunol. Feb. 2007; 44 (6): 1075-1084).*
MacCallum et al. (J. Mol. Biol. Oct. 11, 1996; 262 (5): 732-745).*
Casset et al. (Biochem. Biophys. Res. Commun. Jul. 18, 2003; 307 (1): 198-205).*
De Pascalis et al. (J. Immunol. 2002; 169 (6): 3076-3084).*
Wu et al. (J. Mol. Biol. Nov. 19, 1999; 294 (1): 151-162).*
Vajdos et al. (J. Mol. Biol. Jul. 5, 2002; 320 (2): 415-428).*
Chien et al. (Proc. Natl. Acad. Sci. USA. Jul. 1989; 86 (14): 5532-5536).*
Caldas et al. (Mol. Immunol. May 2003; 39 (15): 941-952).*
Giusti et al. (Proc. Natl. Acad. Sci. USA. May 1987; 84 (9): 2926-2930).*
Winkler et al. (J. Immunol. Oct. 15, 2000; 165 (8): 4505-4514).*
Gussow et al. (Methods in Enzymology. 1991; 203: 99-121).*
Mariuzza et al. (Annu. Rev. Biophys. Biophys. Chem. 1987; 16: 139-159).*
Rudikoff et al. (Proc. Natl. Acad. Sci. USA. 1982; 79: 1979-1983).*
Riemer et al. (Mol. Immunol. 2005; 42: 1121-1124).*
Jiang et al. (J. Biol. Chem. Feb. 11, 2005; 280 (6): 4656-4662).*
Stancovski et al. (Proceedings of the National Academy of Science USA. 1991; 88: 8691-8695).*
Press et al. (J. Immunol. Dec. 15, 1988; 141 (12): 4410-4417).*
Campanero et al. (J. Cell Biol. Jun. 1990; 110 (6): 2157-65).*
Yamaguchi et al. (Biochem. Biophys. Res. Commun. Nov. 1, 2014; 454 (4): 600-603).*
Communication dated Mar. 14, 2013 issued in a foreign counterpart application.
Ausubel, F. M., et al., "Mutagenesis with Degenerate Oligonucleotides: Creating Numerous Mutations in a Small Dna Sequence", Current Protocols in Molecular Biology, vol. 1, Section 8.2, 1989, 14 pages.
Ausubel, F. M., et al, "Directed Mutagenesis Using the Polymerase Chain Reaction", Current Protocols in Molecular Biology, vol. 1, Chapter 8, Supplement 37, 1997, 11 pages.
Ausubel, F.M., et al. eds. Current Protocols in Molecular Biology. New York: John Wiley and Sons). Chapter 2, including various supplements, (1994).
Friguet, B., et al., "Measurements of the true affinity constant in solution of antigen-antiobdy complexes by enzyme-linked immunosorbent assay", J Immunol Methods, 1985, 77(2), pp. 305-319.
Germano, S., et al., Molecular targets in cancer therapy: the Ron approach, Oncol Rev 2008, 1, pp. 215-224.

(Continued)

*Primary Examiner* — Stephen Rawlings
(74) *Attorney, Agent, or Firm* — Locke Lord LLP

(57) ABSTRACT

The present disclosure provides recombinant antigen-binding regions and antibodies and functional fragments containing such antigen-binding regions that are specific for MST1R, which plays an integral role in various disorders or conditions, such as cancer. These antibodies, accordingly, can be used to treat these and other disorders and conditions. Antibodies of the disclosure also can be used in the diagnostics field, as well as for further investigating the role of MST1R in the progression of disorders associated with tumors. The disclosure also provides nucleic acid sequences encoding the foregoing antibodies, vectors containing the same, pharmaceutical compositions and kits with instructions for use.

39 Claims, 37 Drawing Sheets

(56) References Cited

OTHER PUBLICATIONS

Grossman, H.B., "Clinical applications of monoclonal antibody technology", Urol. Clin. North Amer., 1986, 13(3), pp. 465-474.

Haenel, C., et al., "Characterization of high-affinity antibodies by electrochemiluminescence-based equilibrium titration", Anal Biochem, 2005, 339, pp. 182-184.

Alfonso, R. et al, (editors), "The Value and Benefits of ICH to Drug Regulatory Authorities—Advancing Harmonization for Better Health", International Conference on Harmonisation, 2010, 36 pages.

Gait, M.J. (editor), "Oligonucleotide Synthesis, a practical approach", IRL Press, Oxford. (1984).

Khaw, B. A. et al., "Myocardial infarct Imaging of antibodies to canine cardiac myosin with indium-111-diethylenetriamine pentaacetic acid", Science, 1980, 209 (4453), pp. 295-297.

Khorana, H.G. et al., "Studies on polynucleotides. 103. Total synthesis of the structural gene for an alanine transfer ribonucleic acid from yeast", J. Mol. Biol. 1972, 72(2), pp. 209 217.

Knappik, A. et al., "Fully synthetic human combinatorial antibody libraries (HuCAL) based on modular consensus frameworks and CDRs randomized with trinucleotides", J. Mol. Biol., 2000, 296, pp. 57-86.

Krebs, B. et al., "High-throughput generation and engineering of recombinant human antibodies", J. Immunol. Methods., 2001, 254, pp. 67-84.

Lee, W. et al., "Prognostic Significance of Co-expression of RON and MET Receptors in Node-Negative Breast Cancer Patients", Clin Cancer Res., 2005, 11, pp. 2222-2228.

Lee, S.T., et al, GenBank Accession No: NM_002447.2, *Homo sapiens* macrophage stimulating 1 receptor (c-met-related tyrosine kinase) (MST1R), transcript variant 1, mRNA, first reference (Reference 10) dated 1993.

Varet, B, et al, GeneBank Accession No: NM_009074.1, Mus musculus macrophage stimulating 1 receptor (c-met-related tyrosine kinase) (Mst1r), mRNA, first reference (Reference 10) dated 1977.

Lee, S.T., et al, GenBank Accession No. NP_002438.2, macrophage-stimulating protein receptor isoform 1 preproprotein [*Homo sapiens*], first reference (Reference 10) dated 1993.

Varet, B., et al, GenBank Accession No: NP_033100.1, macrophage stimulating 1 receptor [Mus musculus], first reference (Reference 10) dated 1977.

O'Toole, J.M. et al., "Therapeutic Implications of a Human Neutralizing Antibody to the Macrophage-Stimulating Protein Receptor Tyrosine Kinase (RON), a c-MET Family Member", *Cancer Res.* 2006, 66, pp. 9162-9170.

Watson, N., pBR322 (ATCC Accession No. 37017), Cloning vector pBR322, complete sequence, first reference (Reference 22) dated 1988.

Katocs, A. S. et al., "Chapter 27 Biological Testing", "Chapter 28 Clinical Analysis", Remington's Pharmaceutical Sciences, 18th edition,1990, pp. 484-528.

Rothe, C. et al., "The human combinatorial antibody library HuCAL GOLD combines diversification of all six CDRs according to the natural immune system with a novel display method for efficient selection of high-affinity antibodies", J. Mol. Biol., 2008, 376(4), pp. 1182-1200.

Sambrook, J. et al., Molecular Cloning: A laboratory manual, Second Edition, Spring Harbor Laboratory Press, Cold Spring Harbor, USA 1989.

Unger, E.C. et al., "Magnetic resonance imaging using gadolinium labeled monoclonal antibody", Invest. Radiol., 1985, 20(7), pp. 693-700.

Virnekas, B. et al., "Trinucleotide phosphoramidites: ideal reagents for the synthesis of mixed oligonucleotides for random mutagenesis", Nucl. Acids Res., 1994, 22(25), pp. 5600-5607.

Wang, M. et al., "Oncogenic and invasive potentials of human macrophage-stimulating protein receptor, the RON receptor tyrosine kinase", Carcinogenesis, 2003, 23(8), pp. 1291-1300.

Written Opinion of the International Searching Authority for International Application No. PCT/JP2010/052479—Date of Completion of Opinion: Jul. 8, 2010, 12 pages.

Xiang-Ming, X. et al., "RNA-mediated gene silencing of the RON receptor tyrosine kinase alters oncogenic phenotypes of human colorectal carcinoma cells", Oncogene, 2004, 23, pp. 8464-8474.

Zhou, Y. et al., "Altered expression of the RON receptor tyrosine kinase in primary human colorectal adenocarcinomas: generation of different splicing RON variants and their oncogenic potential", Oncogene 2003, 22, pp. 186-197.

Roitt, A., et al., "Immunology" Mir, p. 150 (2000) (Original in Russian; English translation included).

Mirny, L., et al., "Protein Folding Theory: From Lattice to All-Atom Models", Annu. Rev. Biophys. Biomol. Struct. 30, pp. 361-396, (2001).

Sugiyama, Y., et al., "Generation and Application of a Monoclonal Antibody That Detects a Wide Variety of Protein Tyrosine Kinases", Analytical Biochemistry 347, pp. 112-120 (2005).

Pakula, A., et al., "Genetic Analysis of Protein Stability and Function", Annu. Rev. Genet. 23, pp. 289-310, (1989).

Davis, M., "The Evolutionary and Structural 'Logic' of Antigen Receptor Diversity", Seminars in Immunology 16, pp. 239-243, (2004).

Office Action issued in Russian Application No. 2011137405; dated Jul. 30, 2013.

Stuart Rudikoff et. al., "Single amino acid substitution altering antigen-binding specificity," Proc., Natl. Acad. Sci. USA, Immunology, vol. 79, Mar. 1982, pp. 1979-1983 (corrected citation-reference previously submitted in IDS Apr. 15, 2013).

Rybalsky, N.G., et al., "UDC 579.61: Monoclonal antibodies and hybridomas," Moscow: Academy of Agricultural Sciences, 1989, cited in corresponding RU Application No. 2011137405 (Complete Russian-language document with English translation of the Abstract).

Camp, E.R., et al., "Tyrosine Kinase Receptor RON in Human Pancreatic Cancer," Cancer, vol. 109, No. 6, pp. 1030-1039, 2007.

Montero-Julian, F.A., et al., "Characterization of Two Monoclonal Antibodies Against the RON Tyrosine Kinase Receptor," Hybridoma, vol. 17, No. 6, pp. 541-551, (1998).

Cheng, N., et al., "Transforming Growth Factor-β Signaling-Deficient Fibroblasts Enhance Hepatocyte Growth Factor Signaling in Mammary Carcinoma Cells to Promote Scattering and Invasion," Molecular Cancer Research, vol. 6, No. 10, pp. 1521-1533, 2008.

Lu, Y., et al., "Multiple variants of the RON receptor tyrosine kinase: Biochemical properties, tumorigenic activities, and potential drug targets", Cancer Lett., 2007, 257(2), pp. 157-164.

Yao, H-P, et al., "Agonistic Monoclonal Antibodies Potentiate Tumorigenic and Invasive Activities of Splicing Variant of the RON Receptor Tyrosine Kinase," Cancer Biology & Therapy, vol. 5, No. 9, pp. 1179-1186, 2006.

Sambrook & Russell, "Molecular Cloning, a Laboratory Manual", 3rd. Ed., 2001, vol. 2, 10.47.

* cited by examiner

FIG. 3A
CAGGTGCAATTGGTGGAAAGCGGCGGGGCTCGGTCCAACCGGGCCGGCAGCCTGCGTCTG
AGCTGCGCGGCCTCCGGATTTACCTTTAATTCTTATTCGTTATGTTGGTTGGCCGAAGCC
CCTGGGAAGGTCGGTGAGTGGGTCTCTCGTTCTCAAGCACTACACACCTTATTAT
GCCGATAGCGTGAAGGCGCCGTTTTACCATTTCACGTTATAATTCGAAAACACCCTGTAT
CTGCAAATGAACAGCCTGCGTGCCGAAGATACGGCCGTGTATTATTGCGCGGTGGTTAT
TTTCATGGTATGGATTATTGGGGCCAAGGCACCCTGGTGACCGGTTAGCTCA

FIG. 3B

CAGGTGCAATTGGGTTCAGAGCGGCCCGGAAGTGAAAAACCGGCGGAAAGCCGGAAAATT
AGCTGGAAAGGTTCCGGATATTCCTTACTAATTCTTAATTATTCGATGGCGCAGATG
CCTTGGGAAGGTCGGAGTGAGGCCCTTTATCTATCGGATGATTAGTGCTTAACCGTTAT
TCTCCCAGCTTTCAGGGCCAGGTGACCGGTGACCATTAGCGGTGATAAAGCATTAGCGCGTAT
CTTCAATGCGAGCCGGCCCTGAAAGCGGCACGGATCGGCCATCGTATTATTGCGGGTTTTCT
TATCGTCATTATCTTGGATATTGGATGGCACCGGTGACGGCCAAGGCACCGGTTAGC
TCA

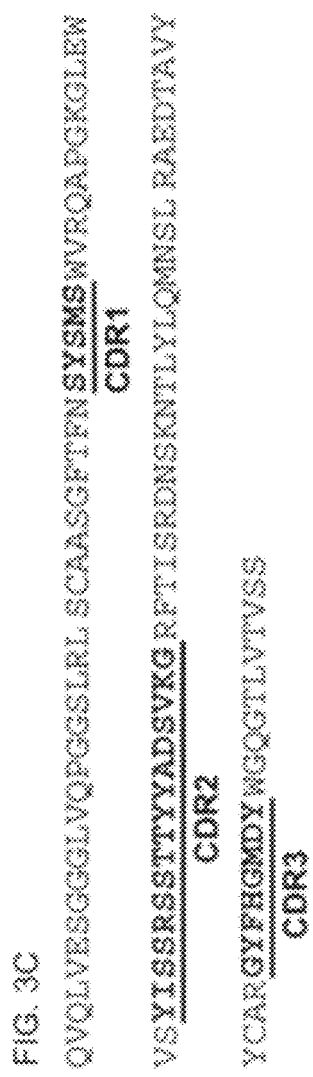

FIG. 3D

QVQLVQSGAEVKKPGESLKI SCKGSGYSFT NYWIS WVRQMPGKGLEW
                                    CDR1

MG FIYPDSYTRYSPSFQG QVTISADKSISTAYLQWSSL KASDTAMY
    CDR2

YCAR FSYRHYLDMDDH WGQGTLVTVSS
     CDR3

FIG. 4A

GATATCGTGCTGACCCAGAGCCCGGCGACCCTGTCCCTGAGCCCAGGCGAACGTGCGACC
CTGACCTGCAGAGCCAGCCAGTCTGTTTCTTTGATTATCTGGTTTGGTACCAGCAGAAA
CCAGGTCAAGCACCGCGTCTATTAATTATGGTGCTTCTAATCGTGCCTGGGGTCCCG
GCCCGTTTTAGCGGCTCTGGATCCGGCGATTTTACCCTGACCATTAGCAGCCTGGAA
CCTGAAGACTTTGCAACTTATTATTGCCAGCAGTATTATAATATGCCTTATACCTTTGGC
CAGGGTACCAAAGTTGAAATTAAACGTACG

FIG. 4B

GATATCGAACTGACCCGACCGGCCGACTCGAGTTGACCGTTGCACGAGTCGACCGCGTATC
TCGTGTAGCGCGATTCTCTGGTCTAAGTATGTTCATTGGTACCAGCAGAACCCCGGG
CAGGCCCAGTTCTTGTGTATTTATCCTGATTAATAAGCGTCCCTCGGGGATCCCGGAACGC
TTTACCGGATCCAACAGCGCGGACCCGGACCATTAGCGCACATTAGCGGCACTCAGCGGGAA
GACGAAGCCGATTATTATTGCCAGTCTTATCGATCGATCGTCTTACTTATGTTATGTTGGC
GGCGGCACGAAGTTAACGGTTCTTGGCGAG

FIG. 4C

GATATCGTGCTGACCCGGAGCCCGGCCCGGCCCTGACCCTGTCCTCCGGCGAACGTGCCGACC
CTGACCTGCCAGGCCAGCCAGCCAGTCCTTGTTTCTCTTTGAATTATCTGGGTTGGTACCAGCAGAA
CCAGGTCAAGCCACCGCGTCTATTAATTTATGGTGCTTCTAATCGTTACGTGCCATCTGGGTCCCG
GCGCGTTTTTAGCGGCTCTGGATCCGGGACGGATTTTACCCTGACCATTAGCAGCCTGGAA
CCTGAAGACTTTGCGACCTATTATTGCTTTCAGTATAGCTTATGTCCTTTTACGTTTTGGC
CAGGGTACCAAAGTTGAAATTAAACGTTACG

FIG. 40

GATATCCTGCTGACCCGAGCCCGGCCTCGTCCTGACCCTGAACCGTCCGACC
CTGAGCTGCAGCAGCCAGTCTGTTTCTTTGATTATCTGGTTACCAGCAGAAA
CCAGGTCAAGCACCGGTCTATTAATTATGGTGCTCAATCGTTCAACTGGATCG
GGCGTTTTACCTCTGGATCCGGATTTTACCCTTACCATTAGCAGCCTGGAA
CCTGAAGACTTTGCACTTATTATTGCCGGCAGTATAATTAATCCTTTACCTTTGGC
CAGGGTACCAAGTTGAAATTAAACGTACG

FIG. 4E

GATTATCGTGCTGACCCAGAGCCCGGACCCCTGTCCCGGCGGAACGTGCGACC
CTGACTTGCAGAGCCAGTCTGTTCTTTGATTATCTGGTTGGTACCAGCAGAAA
CCAGGTCAAGCACCCGGTCTATTAATTTATGGTGCTTCTAATCGTGCAATCGTCCG
GCCGGTTTTAGCGGCTCTGGATCCGGCACGGATTTTTACCCTGACCATCAGCTGGAA
CCTGAAGACTTTGCAGACTTATTATTGCCTCCAGTATTTAATCCTCTCATACGTTCGGC
CAGGGTACGGAAGTTGAAATTAAACGTACG

FIG. 4F

GATATCGTGCTGACCCAGAGCCCCGGAGCCCTGTCTCTGAGCCCGGAACGTGCGACC
CTGAGTGCAGAGGAGCCAGTCGTTTCTGTTCTTGATTAATTACCTGGTTGGTAGCAGAA
CCAGGTCAAGCACGGCGTCTATTAATTAAGTTGCTTCTAATCGTGCAACTGGGGTCCGG
GCGCGTTTAGCCGGCCTGGATCGGCATCGGAATTTTACCGGATTAGCCATTAGCAGCCTGGAA
CCTGAAAGACTTGCCGGACTTATTAATTGCTTGCAGCCTATTAATGCCTTTACCTTTGC
CAGGGTTACCGAAGTTGAATTAACGTACG

FIG. 4G

DIVLTQSPATLSLSPGERATLSCRASQSVSPDYLGWYQQKPGQAPRLLIYGASNRATG
                              ‾‾‾‾‾‾‾‾‾‾‾‾‾‾          ‾‾‾‾‾‾‾‾
                                    CDR1                  CDR2

VPARFSGSGSGTDFTLTISSLEPEDFATYYCQQYYMPYTFGQGTKVEIKRT
                              ‾‾‾‾‾‾‾‾‾
                                 CDR3

FIG. 4J

DIVLTQSPATLSLSPGERATLSCRASQSVSSDYLGWYQQKPGQAPRLLIYGASNRATG
                          |_____CDR1_____|           |_CDR2_|

VPARFSGSGSGTDFTLTISSLEPEDFATYYCQQYNINPFTFGQGTKVEIKRT
                              |__CDR3__|

FIG. 4K

DIVLTQSPATLSLSPGERATLSCRASQSVSPDYLGWYQQKPGQAPRLLIYGASNRATG
                        CDR1                              CDR2

VPARFSGSGSGTDFTLTISSLEPEDFATYYCLQYNPPHTFGQGTKVEIKRT
                                 CDR3

FIG. 4L

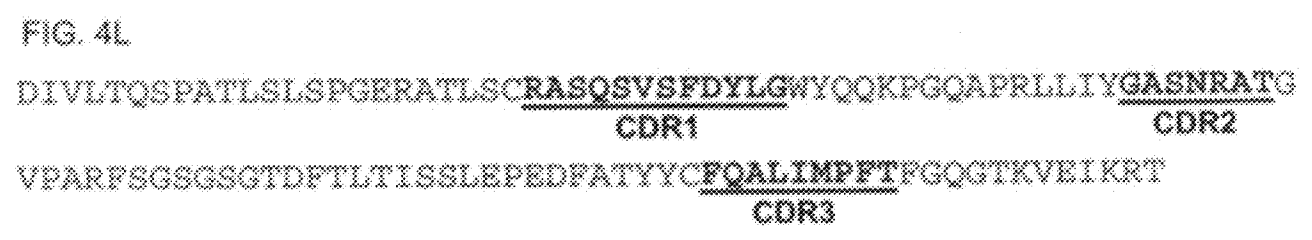

DIVLTQSPATLSLSPGERATLSCRASQSVSFDYLGWYQQKPGQAPRLLIYGASNRATG
                              CDR1                      CDR2

VPARFSGSGSGTDFTLTISSLEPEDFATYYCFQALIMPFTFGQGTKVEIKRT
                              CDR3

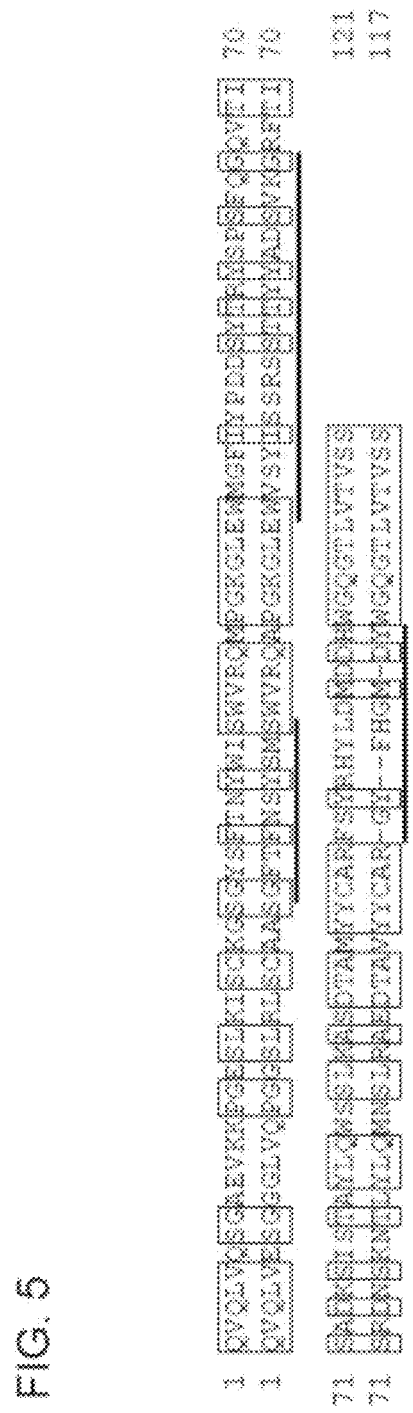

SEQUENCE LISTING

```
<160> NUMBER OF SEQ ID NOS: 83

<210> SEQ ID NO 1
<211> LENGTH: 8
<212> TYPE: PRT
<213> ORGANISM: Homo sapiens

<400> SEQUENCE: 1

Gly Tyr Phe His Gly Met Asp Tyr
1               5

<210> SEQ ID NO 2
<211> LENGTH: 17
<212> TYPE: PRT
<213> ORGANISM: Homo sapiens

<400> SEQUENCE: 2

Tyr Ile Ser Ser Arg Ser Ser Thr Thr Tyr Tyr Ala Asp Ser Val Lys
1               5                   10                  15

Gly
```

```
<210> SEQ ID NO 3
<211> LENGTH: 5
<212> TYPE: PRT
<213> ORGANISM: Homo sapiens

<400> SEQUENCE: 3

Ser Tyr Ser Met Ser
1               5

<210> SEQ ID NO 4
<211> LENGTH: 12
<212> TYPE: PRT
<213> ORGANISM: Homo sapiens

<400> SEQUENCE: 4

Phe Ser Tyr Arg His Tyr Leu Asp Met Asp His
1               5                   10

<210> SEQ ID NO 5
<211> LENGTH: 17
<212> TYPE: PRT
<213> ORGANISM: Homo sapiens

<400> SEQUENCE: 5

Phe Ile Tyr Pro Asp Asp Ser Tyr Thr Arg Tyr Ser Pro Ser Phe Gln
1               5                   10                  15

Gly

<210> SEQ ID NO 6
<211> LENGTH: 5
<212> TYPE: PRT
<213> ORGANISM: Homo sapiens

<400> SEQUENCE: 6

Asn Tyr Trp Ile Ser
1               5

<210> SEQ ID NO 7
<211> LENGTH: 9
<212> TYPE: PRT
<213> ORGANISM: Homo sapiens

<400> SEQUENCE: 7

Gln Gln Tyr Tyr Asn Met Pro Tyr Thr
1               5

<210> SEQ ID NO 8
<211> LENGTH: 11
<212> TYPE: PRT
<213> ORGANISM: Homo sapiens

<400> SEQUENCE: 8

Gln Ser Tyr Asp Ala Thr Glu Phe Thr Tyr Val
1               5                   10

<210> SEQ ID NO 9
<211> LENGTH: 9
<212> TYPE: PRT
<213> ORGANISM: Homo sapiens

<400> SEQUENCE: 9

Phe Gln Tyr Leu Ile Val Pro Phe Thr
1               5
```

-continued

<210> SEQ ID NO 10
<211> LENGTH: 9
<212> TYPE: PRT
<213> ORGANISM: Homo sapiens

<400> SEQUENCE: 10

Gln Gln Tyr Asn Ile Asn Pro Phe Thr
1               5

<210> SEQ ID NO 11
<211> LENGTH: 9
<212> TYPE: PRT
<213> ORGANISM: Homo sapiens

<400> SEQUENCE: 11

Leu Gln Tyr Phe Asn Pro Pro His Thr
1               5

<210> SEQ ID NO 12
<211> LENGTH: 9
<212> TYPE: PRT
<213> ORGANISM: Homo sapiens

<400> SEQUENCE: 12

Phe Gln Ala Leu Ile Met Pro Phe Thr
1               5

<210> SEQ ID NO 13
<211> LENGTH: 12
<212> TYPE: PRT
<213> ORGANISM: Homo sapiens

<400> SEQUENCE: 13

Arg Ala Ser Gln Ser Val Ser Phe Asp Tyr Leu Gly
1               5                   10

<210> SEQ ID NO 14
<211> LENGTH: 7
<212> TYPE: PRT
<213> ORGANISM: Homo sapiens

<400> SEQUENCE: 14

Gly Ala Ser Asn Arg Ala Thr
1               5

<210> SEQ ID NO 15
<211> LENGTH: 11
<212> TYPE: PRT
<213> ORGANISM: Homo sapiens

<400> SEQUENCE: 15

Ser Gly Asp Ser Leu Gly Ser Lys Tyr Val His
1               5                   10

<210> SEQ ID NO 16
<211> LENGTH: 7
<212> TYPE: PRT
<213> ORGANISM: Homo sapiens

<400> SEQUENCE: 16

Arg Asp Asn Lys Arg Pro Ser
1               5

<210> SEQ ID NO 17
<211> LENGTH: 547

<212> TYPE: PRT
<213> ORGANISM: Homo sapiens

<400> SEQUENCE: 17

```
Glu Asp Trp Gln Cys Pro Arg Thr Pro Tyr Ala Ala Ser Arg Asp Phe
1               5                   10                  15

Asp Val Lys Tyr Val Val Pro Ser Phe Ser Ala Gly Gly Leu Val Gln
            20                  25                  30

Ala Met Val Thr Tyr Glu Gly Asp Arg Asn Glu Ser Ala Val Phe Val
        35                  40                  45

Ala Ile Arg Asn Arg Leu His Val Leu Gly Pro Asp Leu Lys Ser Val
    50                  55                  60

Gln Ser Leu Ala Thr Gly Pro Ala Gly Asp Pro Gly Cys Gln Thr Cys
65                  70                  75                  80

Ala Ala Cys Gly Pro Gly Pro His Gly Pro Pro Gly Asp Thr Asp Thr
                85                  90                  95

Lys Val Leu Val Leu Asp Pro Ala Leu Pro Ala Leu Val Ser Cys Gly
            100                 105                 110

Ser Ser Leu Gln Gly Arg Cys Phe Leu His Asp Leu Glu Pro Gln Gly
        115                 120                 125

Thr Ala Val His Leu Ala Ala Pro Ala Cys Leu Phe Ser Ala His His
    130                 135                 140

Asn Arg Pro Asp Asp Cys Pro Asp Cys Val Ala Ser Pro Leu Gly Thr
145                 150                 155                 160

Arg Val Thr Val Val Glu Gln Gly Gln Ala Ser Tyr Phe Tyr Val Ala
                165                 170                 175

Ser Ser Leu Asp Ala Ala Val Ala Gly Ser Phe Ser Pro Arg Ser Val
            180                 185                 190

Ser Ile Arg Arg Leu Lys Ala Asp Ala Ser Gly Phe Ala Pro Gly Phe
        195                 200                 205

Val Ala Leu Ser Val Leu Pro Lys His Leu Val Ser Tyr Ser Ile Glu
    210                 215                 220

Tyr Val His Ser Phe His Thr Gly Ala Phe Val Tyr Phe Leu Thr Val
225                 230                 235                 240

Gln Pro Ala Ser Val Thr Asp Asp Pro Ser Ala Leu His Thr Arg Leu
                245                 250                 255

Ala Arg Leu Ser Ala Thr Glu Pro Glu Leu Gly Asp Tyr Arg Glu Leu
            260                 265                 270

Val Leu Asp Cys Arg Phe Ala Pro Lys Arg Arg Arg Gly Ala Pro
        275                 280                 285

Glu Gly Gly Gln Pro Tyr Pro Val Leu Gln Val Ala His Ser Ala Pro
    290                 295                 300

Val Gly Ala Gln Leu Ala Thr Glu Leu Ser Ile Ala Glu Gly Gln Glu
305                 310                 315                 320

Val Leu Phe Gly Val Phe Val Thr Gly Lys Asp Gly Gly Pro Gly Val
                325                 330                 335

Gly Pro Asn Ser Val Val Cys Ala Phe Pro Ile Asp Leu Leu Asp Thr
            340                 345                 350

Leu Ile Asp Glu Gly Val Glu Arg Cys Cys Glu Ser Pro Val His Pro
        355                 360                 365

Gly Leu Arg Arg Gly Leu Asp Phe Phe Gln Ser Pro Ser Phe Cys Pro
    370                 375                 380

Asn Pro Pro Gly Leu Glu Ala Leu Ser Pro Asn Thr Ser Cys Arg His
385                 390                 395                 400
```

```
Phe Pro Leu Leu Val Ser Ser Phe Ser Arg Val Asp Leu Phe Asn
                405                 410                 415

Gly Leu Leu Gly Pro Val Gln Val Thr Ala Leu Tyr Val Thr Arg Leu
            420                 425                 430

Asp Asn Val Thr Val Ala His Met Gly Thr Met Asp Gly Arg Ile Leu
            435                 440                 445

Gln Val Glu Leu Val Arg Ser Leu Asn Tyr Leu Leu Tyr Val Ser Asn
    450                 455                 460

Phe Ser Leu Gly Asp Ser Gly Gln Pro Val Gln Arg Asp Val Ser Arg
465                 470                 475                 480

Leu Gly Asp His Leu Leu Phe Ala Ser Gly Asp Gln Val Phe Gln Val
                485                 490                 495

Pro Ile Arg Gly Pro Gly Cys Arg His Phe Leu Thr Cys Gly Arg Cys
            500                 505                 510

Leu Arg Ala Trp His Phe Met Gly Cys Gly Trp Cys Gly Asn Met Cys
            515                 520                 525

Gly Gln Gln Lys Glu Cys Pro Gly Ser Trp Gln Gln Asp His Cys Pro
    530                 535                 540

Pro Lys Leu
545

<210> SEQ ID NO 18
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 18 cag gtg caa ttg gtg gaa agc ggc ggc ggc ctg gtg caa ccg ggc ggc        48
Gln Val Gln Leu Val Glu Ser Gly Gly Gly Leu Val Gln Pro Gly Gly
1               5                   10                  15 agc ctg cgt ctg agc tgc gcg gcc tcc gga ttt acc ttt aat tct tat        96
Ser Leu Arg Leu Ser Cys Ala Ala Ser Gly Phe Thr Phe Asn Ser Tyr
            20                  25                  30 tct atg tct tgg gtg cgc caa gcc cct ggg aag ggt ctc gag tgg gtg       144
Ser Met Ser Trp Val Arg Gln Ala Pro Gly Lys Gly Leu Glu Trp Val
        35                  40                  45 agc tat atc tct tct cgt tct agc act acc tat tat gcg gat agc gtg       192
Ser Tyr Ile Ser Ser Arg Ser Ser Thr Thr Tyr Tyr Ala Asp Ser Val
    50                  55                  60 aaa ggc cgt ttt acc att tca cgt gat aat tcg aaa aac acc ctg tat       240
Lys Gly Arg Phe Thr Ile Ser Arg Asp Asn Ser Lys Asn Thr Leu Tyr
65                  70                  75                  80 ctg caa atg aac agc ctg cgt gcg gaa gat acg gcc gtg tat tat tgc       288
Leu Gln Met Asn Ser Leu Arg Ala Glu Asp Thr Ala Val Tyr Tyr Cys
                85                  90                  95 gcg cgt ggt tat ttt cat ggt atg gat tat tgg ggc caa ggc acc ctg       336
Ala Arg Gly Tyr Phe His Gly Met Asp Tyr Trp Gly Gln Gly Thr Leu
            100                 105                 110 gtg acg gtt agc tca                                                   351
Val Thr Val Ser Ser
        115

<210> SEQ ID NO 19
<211> LENGTH: 117
<212> TYPE: PRT
<213> ORGANISM: Homo sapiens
```

<400> SEQUENCE: 19

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ser Met Ser Trp Val Arg Gln Ala Pro Gly Lys Gly Leu Glu Trp Val
        35                  40                  45

Ser Tyr Ile Ser Ser Arg Ser Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Phe His Gly Met Asp Tyr Trp Gly Gln Gly Thr Leu
            100                 105                 110

Val Thr Val Ser Ser
        115

<210> SEQ ID NO 20
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 20 cag gtg caa ttg gtt cag agc ggc gcg gaa gtg aaa aaa ccg ggc gaa      48
Gln Val Gln Leu Val Gln Ser Gly Ala Glu Val Lys Lys Pro Gly Glu
1               5                   10                  15 agc ctg aaa att agc tgc aaa ggt tcc gga tat tcc ttt act aat tat      96
Ser Leu Lys Ile Ser Cys Lys Gly Ser Gly Tyr Ser Phe Thr Asn Tyr
            20                  25                  30 tgg att tct tgg gtg cgc cag atg cct ggg aag ggt ctc gag tgg atg     144
Trp Ile Ser Trp Val Arg Gln Met Pro Gly Lys Gly Leu Glu Trp Met
        35                  40                  45 ggc ttt atc tat ccg gat gat agc tat acc cgt tat tct ccg agc ttt     192
Gly Phe Ile Tyr Pro Asp Asp Ser Tyr Thr Arg Tyr Ser Pro Ser Phe
    50                  55                  60 cag ggc cag gtg acc att agc gcg gat aaa agc att agc acc gcg tat     240
Gln Gly Gln Val Thr Ile Ser Ala Asp Lys Ser Ile Ser Thr Ala Tyr
65                  70                  75                  80 ctt caa tgg agc agc ctg aaa gcg agc gat acg gcc atg tat tat tgc     288
Leu Gln Trp Ser Ser Leu Lys Ala Ser Asp Thr Ala Met Tyr Tyr Cys
                85                  90                  95 gcg cgt ttt tct tat cgt cat tat ctt gat atg gat gat cat tgg ggc     336
Ala Arg Phe Ser Tyr Arg His Tyr Leu Asp Met Asp Asp His Trp Gly
            100                 105                 110 caa ggc acc ctg gtg acg gtt agc tca                                  363
Gln Gly Thr Leu Val Thr Val Ser Ser
        115                 120

<210> SEQ ID NO 21
<211> LENGTH: 121
<212> TYPE: PRT
<213> ORGANISM: Homo sapiens

<400> SEQUENCE: 21

Gln Val Gln Leu Val Gln Ser Gly Ala Glu Val Lys Lys Pro Gly Glu

```
               1               5                  10                 15
            Ser Leu Lys Ile Ser Cys Lys Gly Ser Gly Tyr Ser Phe Thr Asn Tyr
                           20                 25                 30

Trp Ile Ser Trp Val Arg Gln Met Pro Gly Lys Gly Leu Glu Trp Met
                        35                 40                 45

Gly Phe Ile Tyr Pro Asp Asp Ser Tyr Thr Arg Tyr Ser Pro Ser Phe
                     50                 55                 60

Gln Gly Gln Val Thr Ile Ser Ala Asp Lys Ser Ile Ser Thr Ala Tyr
            65                 70                 75                 80

Leu Gln Trp Ser Ser Leu Lys Ala Ser Asp Thr Ala Met Tyr Tyr Cys
                           85                 90                 95

Ala Arg Phe Ser Tyr Arg His Tyr Leu Asp Met Asp Asp His Trp Gly
                         100                105                110

Gln Gly Thr Leu Val Thr Val Ser Ser
                       115                120

<210> SEQ ID NO 22
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 22 gat atc gtg ctg acc cag agc ccg gcg acc ctg agc ctg tct ccg ggc      48
Asp Ile Val Leu Thr Gln Ser Pro Ala Thr Leu Ser Leu Ser Pro Gly
1               5                  10                 15 gaa cgt gcg acc ctg agc tgc aga gcg agc cag tct gtt tct ttt gat      96
Glu Arg Ala Thr Leu Ser Cys Arg Ala Ser Gln Ser Val Ser Phe Asp
             20                 25                 30 tat ctg ggt tgg tac cag cag aaa cca ggt caa gca ccg cgt cta tta     144
Tyr Leu Gly Trp Tyr Gln Gln Lys Pro Gly Gln Ala Pro Arg Leu Leu
         35                 40                 45 att tat ggt gct tct aat cgt gca act ggg gtc ccg gcg cgt ttt agc     192
Ile Tyr Gly Ala Ser Asn Arg Ala Thr Gly Val Pro Ala Arg Phe Ser
     50                 55                 60 ggc tct gga tcc ggc acg gat ttt acc ctg acc att agc agc ctg gaa     240
Gly Ser Gly Ser Gly Thr Asp Phe Thr Leu Thr Ile Ser Ser Leu Glu
65                 70                 75                 80 cct gaa gac ttt gcg act tat tat tgc cag cag tat tat aat atg cct     288
Pro Glu Asp Phe Ala Thr Tyr Tyr Cys Gln Gln Tyr Tyr Asn Met Pro
                85                 90                 95 tat acc ttt ggc cag ggt acg aaa gtt gaa att aaa cgt acg             330
Tyr Thr Phe Gly Gln Gly Thr Lys Val Glu Ile Lys Arg Thr
            100                105                110

<210> SEQ ID NO 23
<211> LENGTH: 110
<212> TYPE: PRT
<213> ORGANISM: Homo sapiens

<400> SEQUENCE: 23

Asp Ile Val Leu Thr Gln Ser Pro Ala Thr Leu Ser Leu Ser Pro Gly
1               5                  10                 15

Glu Arg Ala Thr Leu Ser Cys Arg Ala Ser Gln Ser Val Ser Phe Asp
             20                 25                 30

Tyr Leu Gly Trp Tyr Gln Gln Lys Pro Gly Gln Ala Pro Arg Leu Leu
         35                 40                 45
```

```
Ile Tyr Gly Ala Ser Asn Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Thr Tyr Tyr Cys Gln Gln Tyr Tyr Asn Met Pro
                85                  90                  95
Tyr Thr Phe Gly Gln Gly Thr Lys Val Glu Ile Lys Arg Thr
            100                 105                 110
```

<210> SEQ ID NO 24
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 24

```
gat atc gaa ctg acc cag ccg cct tca gtg agc gtt gca cca ggt cag    48
Asp Ile Glu Leu Thr Gln Pro Pro Ser Val Ser Val Ala Pro Gly Gln
1               5                   10                  15 acc gcg cgt atc tcg tgt agc ggc gat tct ctt ggt tct aag tat gtt    96
Thr Ala Arg Ile Ser Cys Ser Gly Asp Ser Leu Gly Ser Lys Tyr Val
            20                  25                  30 cat tgg tac cag cag aaa ccc ggg cag gcg cca gtt ctt gtg att tat   144
His Trp Tyr Gln Gln Lys Pro Gly Gln Ala Pro Val Leu Val Ile Tyr
        35                  40                  45 cgt gat aat aag cgt ccc tca ggc atc ccg gaa cgc ttt agc gga tcc   192
Arg Asp Asn Lys Arg Pro Ser Gly Ile Pro Glu Arg Phe Ser Gly Ser
    50                  55                  60 aac agc ggc aac acc gcg acc ctg acc att agc ggc act cag gcg gaa   240
Asn Ser Gly Asn Thr Ala Thr Leu Thr Ile Ser Gly Thr Gln Ala Glu
65                  70                  75                  80 gac gaa gcg gat tat tat tgc cag tct tat gat gct act gag ttt act   288
Asp Glu Ala Asp Tyr Tyr Cys Gln Ser Tyr Asp Ala Thr Glu Phe Thr
                85                  90                  95 tat gtg ttt ggc ggc ggc acg aag tta acc gtt ctt ggc cag           330
Tyr Val Phe Gly Gly Gly Thr Lys Leu Thr Val Leu Gly Gln
            100                 105                 110
```

<210> SEQ ID NO 25
<211> LENGTH: 110
<212> TYPE: PRT
<213> ORGANISM: Homo sapiens

<400> SEQUENCE: 25

```
Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Ser Lys Tyr Val
            20                  25                  30

His Trp Tyr Gln Gln Lys Pro Gly Gln Ala Pro Val Leu Val Ile Tyr
        35                  40                  45

Arg Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Ala Thr Glu Phe Thr
                85                  90                  95

Tyr Val Phe Gly Gly Gly Thr Lys Leu Thr Val Leu Gly Gln
            100                 105                 110
```

<210> SEQ ID NO 26
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 26

```
gat atc gtg ctg acc cag agc ccg gcg acc ctg agc ctg tct ccg ggc        48
Asp Ile Val Leu Thr Gln Ser Pro Ala Thr Leu Ser Leu Ser Pro Gly
1               5                   10                  15 gaa cgt gcg acc ctg agc tgc aga gcg agc cag tct gtt tct ttt gat        96
Glu Arg Ala Thr Leu Ser Cys Arg Ala Ser Gln Ser Val Ser Phe Asp
            20                  25                  30 tat ctg ggt tgg tac cag cag aaa cca ggt caa gca ccg cgt cta tta       144
Tyr Leu Gly Trp Tyr Gln Gln Lys Pro Gly Gln Ala Pro Arg Leu Leu
        35                  40                  45 att tat ggt gct tct aat cgt gca act ggg gtc ccg gcg cgt ttt agc       192
Ile Tyr Gly Ala Ser Asn Arg Ala Thr Gly Val Pro Ala Arg Phe Ser
    50                  55                  60 ggc tct gga tcc ggc acg gat ttt acc ctg acc att agc agc ctg gaa       240
Gly Ser Gly Ser Gly Thr Asp Phe Thr Leu Thr Ile Ser Ser Leu Glu
65                  70                  75                  80 cct gaa gac ttt gcg acc tat tat tgc ttt cag tat ctt att gtt cct       288
Pro Glu Asp Phe Ala Thr Tyr Tyr Cys Phe Gln Tyr Leu Ile Val Pro
                85                  90                  95 ttt acc ttt ggc cag ggt acg aaa gtt gaa att aaa cgt acg               330
Phe Thr Phe Gly Gln Gly Thr Lys Val Glu Ile Lys Arg Thr
            100                 105                 110
```

<210> SEQ ID NO 27
<211> LENGTH: 110
<212> TYPE: PRT
<213> ORGANISM: Homo sapiens

<400> SEQUENCE: 27

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Phe Asp
            20                  25                  30

Tyr Leu Gly Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Phe Gln Tyr Leu Ile Val Pro
                85                  90                  95

Phe Thr Phe Gly Gln Gly Thr Lys Val Glu Ile Lys Arg Thr
            100                 105                 110
```

<210> SEQ ID NO 28
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 28

```
gat atc gtg ctg acc cag agc ccg gcg acc ctg agc ctg tct ccg ggc      48
Asp Ile Val Leu Thr Gln Ser Pro Ala Thr Leu Ser Leu Ser Pro Gly
1               5                   10                  15 gaa cgt gcg acc ctg agc tgc aga gcg agc cag tct gtt tct ttt gat      96
Glu Arg Ala Thr Leu Ser Cys Arg Ala Ser Gln Ser Val Ser Phe Asp
            20                  25                  30 tat ctg ggt tgg tac cag cag aaa cca ggt caa gca ccg cgt cta tta    144
Tyr Leu Gly Trp Tyr Gln Gln Lys Pro Gly Gln Ala Pro Arg Leu Leu
        35                  40                  45 att tat ggt gct tct aat cgt gca act ggg gtc ccg gcg cgt ttt agc    192
Ile Tyr Gly Ala Ser Asn Arg Ala Thr Gly Val Pro Ala Arg Phe Ser
    50                  55                  60 ggc tct gga tcc ggc acg gat ttt acc ctg acc att agc agc ctg gaa    240
Gly Ser Gly Ser Gly Thr Asp Phe Thr Leu Thr Ile Ser Ser Leu Glu
65                  70                  75                  80 cct gaa gac ttt gcg acc tat tat tgc cag cag tat aat att aat cct    288
Pro Glu Asp Phe Ala Thr Tyr Tyr Cys Gln Gln Tyr Asn Ile Asn Pro
                85                  90                  95 ttt acc ttt ggc cag ggt acg aaa gtt gaa att aaa cgt acg              330
Phe Thr Phe Gly Gln Gly Thr Lys Val Glu Ile Lys Arg Thr
            100                 105                 110

<210> SEQ ID NO 29
<211> LENGTH: 110
<212> TYPE: PRT
<213> ORGANISM: Homo sapiens

<400> SEQUENCE: 29

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Phe Asp
            20                  25                  30

Tyr Leu Gly Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Asn Ile Asn Pro
                85                  90                  95

Phe Thr Phe Gly Gln Gly Thr Lys Val Glu Ile Lys Arg Thr
            100                 105                 110

<210> SEQ ID NO 30
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 30 gat atc gtg ctg acc cag agc ccg gcg acc ctg agc ctg tct ccg ggc      48
Asp Ile Val Leu Thr Gln Ser Pro Ala Thr Leu Ser Leu Ser Pro Gly
1               5                   10                  15 gaa cgt gcg acc ctg agc tgc aga gcg agc cag tct gtt tct ttt gat      96
Glu Arg Ala Thr Leu Ser Cys Arg Ala Ser Gln Ser Val Ser Phe Asp
            20                  25                  30 tat ctg ggt tgg tac cag cag aaa cca ggt caa gca ccg cgt cta tta    144
Tyr Leu Gly Trp Tyr Gln Gln Lys Pro Gly Gln Ala Pro Arg Leu Leu
```

| | | | | | | | | | | | | | | | | |
|---|---|---|---|---|---|---|---|---|---|---|---|---|---|---|---|---|
| | | 35 | | | | 40 | | | | | 45 | | | | | |
| att | tat | ggt | gct | tct | aat | cgt | gca | act | ggg | gtc | ccg | gcg | cgt | ttt | agc | 192 |
| Ile | Tyr | Gly | Ala | Ser | Asn | Arg | Ala | Thr | Gly | Val | Pro | Ala | Arg | Phe | Ser | |
| | | 50 | | | | 55 | | | | | 60 | | | | | |
| ggc | tct | gga | tcc | ggc | acg | gat | ttt | acc | ctg | acc | att | agc | agc | ctg | gaa | 240 |
| Gly | Ser | Gly | Ser | Gly | Thr | Asp | Phe | Thr | Leu | Thr | Ile | Ser | Ser | Leu | Glu | |
| 65 | | | | | 70 | | | | | 75 | | | | | 80 | |
| cct | gaa | gac | ttt | gcg | acc | tat | tat | tgc | ctt | cag | tat | ttt | aat | cct | cct | 288 |
| Pro | Glu | Asp | Phe | Ala | Thr | Tyr | Tyr | Cys | Leu | Gln | Tyr | Phe | Asn | Pro | Pro | |
| | | | | 85 | | | | | 90 | | | | | 95 | | |
| cat | acc | ttt | ggc | cag | ggt | acg | aaa | gtt | gaa | att | aaa | cgt | acg | | | 330 |
| His | Thr | Phe | Gly | Gln | Gly | Thr | Lys | Val | Glu | Ile | Lys | Arg | Thr | | | |
| | | | 100 | | | | | 105 | | | | | 110 | | | |

<210> SEQ ID NO 31
<211> LENGTH: 110
<212> TYPE: PRT
<213> ORGANISM: Homo sapiens

<400> SEQUENCE: 31

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Phe Asp
            20                  25                  30

Tyr Leu Gly Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Tyr Phe Asn Pro Pro
                85                  90                  95

His Thr Phe Gly Gln Gly Thr Lys Val Glu Ile Lys Arg Thr
            100                 105                 110

<210> SEQ ID NO 32
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 32

| | | | | | | | | | | | | | | | | |
|---|---|---|---|---|---|---|---|---|---|---|---|---|---|---|---|---|
| gat | atc | gtg | ctg | acc | cag | agc | ccg | gcg | acc | ctg | agc | ctg | tct | ccg | ggc | 48 |
| Asp | Ile | Val | Leu | Thr | Gln | Ser | Pro | Ala | Thr | Leu | Ser | Leu | Ser | Pro | Gly | |
| 1 | | | | 5 | | | | | 10 | | | | | 15 | | |
| gaa | cgt | gcg | acc | ctg | agc | tgc | aga | gcg | agc | cag | tct | gtt | tct | ttt | gat | 96 |
| Glu | Arg | Ala | Thr | Leu | Ser | Cys | Arg | Ala | Ser | Gln | Ser | Val | Ser | Phe | Asp | |
| | | 20 | | | | | 25 | | | | | 30 | | | | |
| tat | ctg | ggt | tgg | tac | cag | cag | aaa | cca | ggt | caa | gca | ccg | cgt | cta | tta | 144 |
| Tyr | Leu | Gly | Trp | Tyr | Gln | Gln | Lys | Pro | Gly | Gln | Ala | Pro | Arg | Leu | Leu | |
| | | | 35 | | | | | 40 | | | | | 45 | | | |
| att | tat | ggt | gct | tct | aat | cgt | gca | act | ggg | gtc | ccg | gcg | cgt | ttt | agc | 192 |
| Ile | Tyr | Gly | Ala | Ser | Asn | Arg | Ala | Thr | Gly | Val | Pro | Ala | Arg | Phe | Ser | |
| | | 50 | | | | 55 | | | | | 60 | | | | | |
| ggc | tct | gga | tcc | ggc | acg | gat | ttt | acc | ctg | acc | att | agc | agc | ctg | gaa | 240 |
| Gly | Ser | Gly | Ser | Gly | Thr | Asp | Phe | Thr | Leu | Thr | Ile | Ser | Ser | Leu | Glu | |
| 65 | | | | | 70 | | | | | 75 | | | | | 80 | |
| cct | gaa | gac | ttt | gcg | acc | tat | tat | tgc | ttt | cag | gct | ctt | att | atg | cct | 288 |
| Pro | Glu | Asp | Phe | Ala | Thr | Tyr | Tyr | Cys | Phe | Gln | Ala | Leu | Ile | Met | Pro | |
| | | | | 85 | | | | | 90 | | | | | 95 | | |

```
              Pro Glu Asp Phe Ala Thr Tyr Tyr Cys Phe Gln Ala Leu Ile Met Pro
                              85                  90                  95 ttt acc ttt ggc cag ggt acg aaa gtt gaa att aaa cgt acg                        330
Phe Thr Phe Gly Gln Gly Thr Lys Val Glu Ile Lys Arg Thr
            100                 105                 110

<210> SEQ ID NO 33
<211> LENGTH: 110
<212> TYPE: PRT
<213> ORGANISM: Homo sapiens

<400> SEQUENCE: 33

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Phe Asp
            20                  25                  30

Tyr Leu Gly Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Phe Gln Ala Leu Ile Met Pro
                85                  90                  95

Phe Thr Phe Gly Gln Gly Thr Lys Val Glu Ile Lys Arg Thr
            100                 105                 110

<210> SEQ ID NO 34
<211> LENGTH: 24
<212> TYPE: DNA
<213> ORGANISM: Artificial Sequence
<220> FEATURE:
<223> OTHER INFORMATION: PCR forward primer

<400> SEQUENCE: 34
ttggcccagt ccagacctcg agtc                                                      24

<210> SEQ ID NO 35
<211> LENGTH: 25
<212> TYPE: DNA
<213> ORGANISM: Artificial Sequence
<220> FEATURE:
<223> OTHER INFORMATION: PCR reverse primer

<400> SEQUENCE: 35
actctgtgga gtgagggacc taatg                                                     25

<210> SEQ ID NO 36
<211> LENGTH: 4200
<212> TYPE: DNA
<213> ORGANISM: Macaca fascicularis
<220> FEATURE:
<221> NAME/KEY: CDS
<222> LOCATION: (1)..(4200)

<400> SEQUENCE: 36 atg gag ctc ctc cct ccg ctg cct cag tcc ttc tta ctg ctg ctg ctg            48
Met Glu Leu Leu Pro Pro Leu Pro Gln Ser Phe Leu Leu Leu Leu Leu
1               5                   10                  15 ttg cct gcc aag ccc gcg gcg gcc aag gaa tgg cag tgc ccg cgc acc            96
Leu Pro Ala Lys Pro Ala Ala Ala Lys Glu Trp Gln Cys Pro Arg Thr
            20                  25                  30
```

-continued

| | | |
|---|---|---|
| ccc tac gcg gcc tct cga gac ttt aac gtg aag tac atg gtg ccc agc<br>Pro Tyr Ala Ala Ser Arg Asp Phe Asn Val Lys Tyr Met Val Pro Ser<br>35 40 45 | 144 | |
| ttc tcc gcc gga ggc ctg gtg cag acc atg gtg acc tac cag ggc gac<br>Phe Ser Ala Gly Gly Leu Val Gln Thr Met Val Thr Tyr Gln Gly Asp<br>50 55 60 | 192 | |
| aaa aat gag agt gct gtg ttt gta gcc ata cgc aat cgc ctg cac gtg<br>Lys Asn Glu Ser Ala Val Phe Val Ala Ile Arg Asn Arg Leu His Val<br>65 70 75 80 | 240 | |
| ctt ggg cct gac ctg aag tct gtc cag agc ctg gcc acg ggc cct gct<br>Leu Gly Pro Asp Leu Lys Ser Val Gln Ser Leu Ala Thr Gly Pro Ala<br>85 90 95 | 288 | |
| ggg gac cct ggc tgc cag acg tgt gca gcc tgt ggc cca ggc ccc cac<br>Gly Asp Pro Gly Cys Gln Thr Cys Ala Ala Cys Gly Pro Gly Pro His<br>100 105 110 | 336 | |
| ggc cct tcc ggt gac aca gac aca aag gtg ctg gtg ctg gag ccc gcg<br>Gly Pro Ser Gly Asp Thr Asp Thr Lys Val Leu Val Leu Glu Pro Ala<br>115 120 125 | 384 | |
| ctg cct gcc ctg gtc agt tgt ggc tcc agc ctg cag ggc cgc tgc ttc<br>Leu Pro Ala Leu Val Ser Cys Gly Ser Ser Leu Gln Gly Arg Cys Phe<br>130 135 140 | 432 | |
| ctg cat gac cta gat ccc caa ggg aca gcc gtg cat ctg gca gcg cca<br>Leu His Asp Leu Asp Pro Gln Gly Thr Ala Val His Leu Ala Ala Pro<br>145 150 155 160 | 480 | |
| gcc tgc ctc ttc tca gcc cac cat aac cgg ccc gat gac tgc ccc gac<br>Ala Cys Leu Phe Ser Ala His His Asn Arg Pro Asp Asp Cys Pro Asp<br>165 170 175 | 528 | |
| tgt gtg gcc agc cca ttg ggc acc cgt gtg act gtg gtt gag caa ggc<br>Cys Val Ala Ser Pro Leu Gly Thr Arg Val Thr Val Val Glu Gln Gly<br>180 185 190 | 576 | |
| cag gcc tcc tat ttc tac gtg gca tcc tca ctg gac gca gcc gtg gct<br>Gln Ala Ser Tyr Phe Tyr Val Ala Ser Ser Leu Asp Ala Ala Val Ala<br>195 200 205 | 624 | |
| gcc agc ttc agc cca cgc tca gtg tct atc agg cgt ctc aag gcc gac<br>Ala Ser Phe Ser Pro Arg Ser Val Ser Ile Arg Arg Leu Lys Ala Asp<br>210 215 220 | 672 | |
| gcc tcg gga ttt gca ccg ggc ttt gtg gca ttg tca gtg ctg ccc aag<br>Ala Ser Gly Phe Ala Pro Gly Phe Val Ala Leu Ser Val Leu Pro Lys<br>225 230 235 240 | 720 | |
| cat ctt gtc tcc tac agt att gaa tat gtg cac agc ttc cat acg gga<br>His Leu Val Ser Tyr Ser Ile Glu Tyr Val His Ser Phe His Thr Gly<br>245 250 255 | 768 | |
| gcc ttc gtc tac ttc ctg act gta cag ccg gcc agc gtg act gat gct<br>Ala Phe Val Tyr Phe Leu Thr Val Gln Pro Ala Ser Val Thr Asp Ala<br>260 265 270 | 816 | |
| cct ggt gcc ctg cac aca cgc ctg gca cga ctt agc gcc act gag cca<br>Pro Gly Ala Leu His Thr Arg Leu Ala Arg Leu Ser Ala Thr Glu Pro<br>275 280 285 | 864 | |
| gag ttg ggt gac tat cgg gag ctg gtc ctc gac tgc aga ttt gct cca<br>Glu Leu Gly Asp Tyr Arg Glu Leu Val Leu Asp Cys Arg Phe Ala Pro<br>290 295 300 | 912 | |
| aaa cgc agg cgc cgg ggg gcc cca gag ggc gga cag ccc tac cct gtg<br>Lys Arg Arg Arg Arg Gly Ala Pro Glu Gly Gly Gln Pro Tyr Pro Val<br>305 310 315 320 | 960 | |
| ctg cgg gtg gcc cac tct gct cca gtg ggt gct caa ctt gcc act gag<br>Leu Arg Val Ala His Ser Ala Pro Val Gly Ala Gln Leu Ala Thr Glu<br>325 330 335 | 1008 | |
| ctg agc att gct gag ggc cag gaa gtg cta ttt ggg gtc ttt gtg gct<br>Leu Ser Ile Ala Glu Gly Gln Glu Val Leu Phe Gly Val Phe Val Ala<br>340 345 350 | 1056 | |

|  |  |
|---|---|
| ggc aag gat agt ggc cct ggc gtg ggc ccc aac tct gtc gtc tgt gcc<br>Gly Lys Asp Ser Gly Pro Gly Val Gly Pro Asn Ser Val Val Cys Ala<br>        355                      360                  365 | 1104 |
| ttc ccc att gac ctg ctg gac aca tta att gat gaa ggt gtg gag cgc<br>Phe Pro Ile Asp Leu Leu Asp Thr Leu Ile Asp Glu Gly Val Glu Arg<br>370                      375                      380 | 1152 |
| tgt tgt gaa tcc cca gtc cat cca ggc ctc cgg cga ggc ctc gac ttc<br>Cys Cys Glu Ser Pro Val His Pro Gly Leu Arg Arg Gly Leu Asp Phe<br>385                      390                      395                  400 | 1200 |
| ttc cag tca ccc agt ttt tgc ccc aac ccg cct ggc ctg gag gcc ccc<br>Phe Gln Ser Pro Ser Phe Cys Pro Asn Pro Pro Gly Leu Glu Ala Pro<br>                      405                      410                  415 | 1248 |
| agc ccc aac acc agc tgc cgc cac ttc cct ttg ctg gtc agt agc agc<br>Ser Pro Asn Thr Ser Cys Arg His Phe Pro Leu Leu Val Ser Ser Ser<br>                    420                      425                      430 | 1296 |
| ttc tca cgt gtg gac cta ttc aat ggg ctg ttg gga aca gta gag gtc<br>Phe Ser Arg Val Asp Leu Phe Asn Gly Leu Leu Gly Thr Val Glu Val<br>                  435                      440                      445 | 1344 |
| act gca ctg tat gtg aca cgc ctt gac aac gtc aca gtg gca cac atg<br>Thr Ala Leu Tyr Val Thr Arg Leu Asp Asn Val Thr Val Ala His Met<br>450                      455                      460 | 1392 |
| ggc aca gcg gat ggg cgt atc ctg cag gtg gag ctg gcc agg tca ctc<br>Gly Thr Ala Asp Gly Arg Ile Leu Gln Val Glu Leu Ala Arg Ser Leu<br>465                      470                      475                  480 | 1440 |
| aac tac ttg ctg tat gtg tcc aac ttc tca ctg ggt gac agt ggg cag<br>Asn Tyr Leu Leu Tyr Val Ser Asn Phe Ser Leu Gly Asp Ser Gly Gln<br>                    485                      490                      495 | 1488 |
| ccc gtg cag cgg gat gtc agt cgc ctt ggg gac cac cta ttc ttc gcc<br>Pro Val Gln Arg Asp Val Ser Arg Leu Gly Asp His Leu Phe Phe Ala<br>                  500                      505                      510 | 1536 |
| tct ggg gac cag gtt ttc cag gta cct atc caa ggc cct ggc tgc cgc<br>Ser Gly Asp Gln Val Phe Gln Val Pro Ile Gln Gly Pro Gly Cys Arg<br>                  515                      520                      525 | 1584 |
| cac ttc ctc acc tgt ggg cgt tgc cta agg gca cag cgt ttc atg ggc<br>His Phe Leu Thr Cys Gly Arg Cys Leu Arg Ala Gln Arg Phe Met Gly<br>                  530                      535                      540 | 1632 |
| tgt ggc tgg tgt ggg aac atg tgt ggc cgg cag aag gag tgt cct ggc<br>Cys Gly Trp Cys Gly Asn Met Cys Gly Arg Gln Lys Glu Cys Pro Gly<br>545                      550                      555                  560 | 1680 |
| tcc tgg caa cag gac cac tgt ccg cct aag ctt act gag ttc cac ccc<br>Ser Trp Gln Gln Asp His Cys Pro Pro Lys Leu Thr Glu Phe His Pro<br>                  565                      570                      575 | 1728 |
| cac agt gga cct tta agg ggc agt aca agg ctg acc ctg tgt ggc tcc<br>His Ser Gly Pro Leu Arg Gly Ser Thr Arg Leu Thr Leu Cys Gly Ser<br>                    580                      585                      590 | 1776 |
| aac ttc tac ctg cac cct tct ggt ctg gtg cct gag gga acc cat cag<br>Asn Phe Tyr Leu His Pro Ser Gly Leu Val Pro Glu Gly Thr His Gln<br>                  595                      600                      605 | 1824 |
| atc acg gtg ggc caa agt ccc tgc cgg cca ctg ccc aag gac agc tca<br>Ile Thr Val Gly Gln Ser Pro Cys Arg Pro Leu Pro Lys Asp Ser Ser<br>610                      615                      620 | 1872 |
| aaa ctc aga cca gtg ccc cgg aaa gac ttt gta gag gag ttt gag tgt<br>Lys Leu Arg Pro Val Pro Arg Lys Asp Phe Val Glu Glu Phe Glu Cys<br>625                      630                      635                  640 | 1920 |
| gaa ctg gag ccc ttg ggc acc caa gca gtg ggg cct acc aac gtc agc<br>Glu Leu Glu Pro Leu Gly Thr Gln Ala Val Gly Pro Thr Asn Val Ser<br>                  645                      650                      655 | 1968 |
| ctc acc gtg act aac atg cca ccg ggc aag cac ttc cgg gta gac ggc<br>Leu Thr Val Thr Asn Met Pro Pro Gly Lys His Phe Arg Val Asp Gly | 2016 |

-continued

```
              660                 665                 670
acc tcc atg ctg aga ggc ttc ttt ttc atg gag cca gtg ctg ata gca    2064
Thr Ser Met Leu Arg Gly Phe Phe Phe Met Glu Pro Val Leu Ile Ala
        675                 680                 685 gtg caa ccc ctc ttt ggc cca cgg gca gga ggc acc tgt ctc act ctt    2112
Val Gln Pro Leu Phe Gly Pro Arg Ala Gly Gly Thr Cys Leu Thr Leu
690                 695                 700 gaa ggc cag agt ctg tct gta ggc acc agc cgg gct gtg ctg gtc aat    2160
Glu Gly Gln Ser Leu Ser Val Gly Thr Ser Arg Ala Val Leu Val Asn
705                 710                 715                 720 ggg act gag tgt ctg cta gca cgg gtc agt gag ggg cag ctt tta tgt    2208
Gly Thr Glu Cys Leu Leu Ala Arg Val Ser Glu Gly Gln Leu Leu Cys
            725                 730                 735 gcc aca ccc cct ggg gcc atg gtg gcc agt gtc ccc ctt agc ctg cag    2256
Ala Thr Pro Pro Gly Ala Met Val Ala Ser Val Pro Leu Ser Leu Gln
        740                 745                 750 gtg ggg ggt gcc cag gta cct ggt tcc tgg acc ttc cac tac aga gaa    2304
Val Gly Gly Ala Gln Val Pro Gly Ser Trp Thr Phe His Tyr Arg Glu
    755                 760                 765 gac cct gtc gtg cta agc atc agc ccc aac tgt ggc tac agc aac tcc    2352
Asp Pro Val Val Leu Ser Ile Ser Pro Asn Cys Gly Tyr Ser Asn Ser
770                 775                 780 cac atc acc atc tgt ggc cag cat cta act tca gca tgg cac tta gtg    2400
His Ile Thr Ile Cys Gly Gln His Leu Thr Ser Ala Trp His Leu Val
785                 790                 795                 800 ctg tca ttc cat gac ggg ctt agg gca gtg gag agc agg tgt gag agg    2448
Leu Ser Phe His Asp Gly Leu Arg Ala Val Glu Ser Arg Cys Glu Arg
            805                 810                 815 cag ctt cca gag cag cag ttg tgc cgc ctg cct gaa tat gtg gtc caa    2496
Gln Leu Pro Glu Gln Gln Leu Cys Arg Leu Pro Glu Tyr Val Val Gln
        820                 825                 830 gac ccc cag gga tgg gtg gca gga aat ctg agt gcc tgg ggg gat gga    2544
Asp Pro Gln Gly Trp Val Ala Gly Asn Leu Ser Ala Trp Gly Asp Gly
    835                 840                 845 gct gct ggc ttt aca ctg cct ggc ttt cgc ttc cta acc cca ccc cat    2592
Ala Ala Gly Phe Thr Leu Pro Gly Phe Arg Phe Leu Thr Pro Pro His
850                 855                 860 cca ccc agt gcc aac cta att cca ctg aag cct gag gag cat gcc att    2640
Pro Pro Ser Ala Asn Leu Ile Pro Leu Lys Pro Glu Glu His Ala Ile
865                 870                 875                 880 aag ttt gag tat att ggg ctg ggt gct gtg act gac tgc gtg ggt gtc    2688
Lys Phe Glu Tyr Ile Gly Leu Gly Ala Val Thr Asp Cys Val Gly Val
            885                 890                 895 aac gtg acc gtg ggt ggt gag agc tgc cag cac gag ttc cgg ggg gac    2736
Asn Val Thr Val Gly Gly Glu Ser Cys Gln His Glu Phe Arg Gly Asp
        900                 905                 910 atg gtt gtc tgc ccc ctg ccc cca tcc ctg cag ctt ggc aag gat ggt    2784
Met Val Val Cys Pro Leu Pro Pro Ser Leu Gln Leu Gly Lys Asp Gly
    915                 920                 925 gcc cca ctg cag gtc tgc gtg gat ggt gaa tgt cac atc ctg ggt aga    2832
Ala Pro Leu Gln Val Cys Val Asp Gly Glu Cys His Ile Leu Gly Arg
930                 935                 940 gtg gtg tgg cca ggg cca gat ggg gtc cca cag agc acg ctc ctt ggt    2880
Val Val Trp Pro Gly Pro Asp Gly Val Pro Gln Ser Thr Leu Leu Gly
945                 950                 955                 960 atc ctg ctg cct ttg ctg ctg ctt gtg gcc gca ttg gcc act gca ctg    2928
Ile Leu Leu Pro Leu Leu Leu Leu Val Ala Ala Leu Ala Thr Ala Leu
            965                 970                 975 gtc ttc agc tac tgg tgg cag agg aag cag cta gtt ctt cct ccc aac    2976
```

```
                                                                    -continued Val Phe Ser Tyr Trp Trp Gln Arg Lys Gln Leu Val Leu Pro Pro Asn
            980                 985                 990 ctg gat gac ctg gca tcc ctg gac  cag act act gga gcc  aca ccc ctg    3024
Leu Asp Asp Leu Ala Ser Leu Asp  Gln Thr Thr Gly Ala  Thr Pro Leu
            995                  1000                1005 cct att ctc tac tcg ggc tct gac tac aga agt ggc ctt gca cgc          3069
Pro Ile Leu Tyr Ser Gly Ser Asp Tyr Arg Ser Gly Leu Ala Arg
    1010                1015                1020 cct gcc act gat ggt cta gat tcc act tgt gtc cat gga gca tcc          3114
Pro Ala Thr Asp Gly Leu Asp Ser Thr Cys Val His Gly Ala Ser
    1025                1030                1035 ttc tcc aat agt gaa gat gaa tcc tgt gtt cca ctg ctg cgg aaa          3159
Phe Ser Asn Ser Glu Asp Glu Ser Cys Val Pro Leu Leu Arg Lys
    1040                1045                1050 gag tcc atc cag cta agg gac ctg gac tct gcg ctg ttg gct gag          3204
Glu Ser Ile Gln Leu Arg Asp Leu Asp Ser Ala Leu Leu Ala Glu
    1055                1060                1065 gtc aag gat gtg ctg att ccc cat gag cgg gtg gtc gcc cac agt          3249
Val Lys Asp Val Leu Ile Pro His Glu Arg Val Val Ala His Ser
    1070                1075                1080 gac cga gtc att ggc aaa ggc cac ttt gga gtt gtc tac cat gga          3294
Asp Arg Val Ile Gly Lys Gly His Phe Gly Val Val Tyr His Gly
    1085                1090                1095 gaa tac ata gac cag gcc cag aat cga atc caa tgt gcc atc aag          3339
Glu Tyr Ile Asp Gln Ala Gln Asn Arg Ile Gln Cys Ala Ile Lys
    1100                1105                1110 tca cta agt cgc atc aca gag atg cag cag gtg gag gcc ttc ctt          3384
Ser Leu Ser Arg Ile Thr Glu Met Gln Gln Val Glu Ala Phe Leu
    1115                1120                1125 cga gag ggg ctg ctc atg cgt ggc ctg aac cac ccg aat gtg ctg          3429
Arg Glu Gly Leu Leu Met Arg Gly Leu Asn His Pro Asn Val Leu
    1130                1135                1140 gct ctc att ggt atc atg ttg cca ccc gag ggc ctg ccc cat gtg          3474
Ala Leu Ile Gly Ile Met Leu Pro Pro Glu Gly Leu Pro His Val
    1145                1150                1155 ctg ctg ccc tat atg tgc cac ggt gac ctg ctc cag ttc atc cgc          3519
Leu Leu Pro Tyr Met Cys His Gly Asp Leu Leu Gln Phe Ile Arg
    1160                1165                1170 tca cct cag cgg aac ccc acc gtg aag gac ctc atc agc ttt ggc          3564
Ser Pro Gln Arg Asn Pro Thr Val Lys Asp Leu Ile Ser Phe Gly
    1175                1180                1185 ctg cag gta gcc cat ggc atg gag tac ctc gca gag cag aag ttt          3609
Leu Gln Val Ala His Gly Met Glu Tyr Leu Ala Glu Gln Lys Phe
    1190                1195                1200 gtg cac agg gac ctg gct gcg cga aac tgc atg ctg gac gag tca          3654
Val His Arg Asp Leu Ala Ala Arg Asn Cys Met Leu Asp Glu Ser
    1205                1210                1215 ttc act gtc aaa gtg gct gac ttt ggt ttg gcc cgt gac atc ctg          3699
Phe Thr Val Lys Val Ala Asp Phe Gly Leu Ala Arg Asp Ile Leu
    1220                1225                1230 gac aag gaa tac tat agt gtt caa cag cat cgc cac gct cgc cta          3744
Asp Lys Glu Tyr Tyr Ser Val Gln Gln His Arg His Ala Arg Leu
    1235                1240                1245 cct gtg aag tgg atg gcg ctg gag agc ctg cag acc tat aga ttt          3789
Pro Val Lys Trp Met Ala Leu Glu Ser Leu Gln Thr Tyr Arg Phe
    1250                1255                1260 acc acc aag tct gat gtg tgg tca ttt ggt gtg ctg ctg tgg gaa          3834
Thr Thr Lys Ser Asp Val Trp Ser Phe Gly Val Leu Leu Trp Glu
    1265                1270                1275
```

| | | | | | | | | | | | | | | |
|---|---|---|---|---|---|---|---|---|---|---|---|---|---|---|
| ctg | ttg | aca | cgg | ggt | gcc | cca | cca | tac | ccc | cac | atc | gac | cct | ttt | 3879 |
| Leu | Leu | Thr | Arg | Gly | Ala | Pro | Pro | Tyr | Pro | His | Ile | Asp | Pro | Phe | |
| 1280 | | | | 1285 | | | | | 1290 | | | | | | |
| gac | ctc | acc | cac | ttc | ctg | gcc | cag | ggt | cgg | cgc | ctg | ccc | cag | cct | 3924 |
| Asp | Leu | Thr | His | Phe | Leu | Ala | Gln | Gly | Arg | Arg | Leu | Pro | Gln | Pro | |
| 1295 | | | | | 1300 | | | | | 1305 | | | | | |
| gag | tat | tgc | ccc | aat | tct | ctg | tac | caa | gtg | atg | cag | caa | tgc | tgg | 3969 |
| Glu | Tyr | Cys | Pro | Asn | Ser | Leu | Tyr | Gln | Val | Met | Gln | Gln | Cys | Trp | |
| 1310 | | | | | 1315 | | | | | 1320 | | | | | |
| gag | gcg | gac | cca | gca | gca | cga | ccc | acc | ttc | gga | gta | cta | gtg | ggg | 4014 |
| Glu | Ala | Asp | Pro | Ala | Ala | Arg | Pro | Thr | Phe | Gly | Val | Leu | Val | Gly | |
| 1325 | | | | 1330 | | | | | 1335 | | | | | | |
| gaa | gtg | gag | cag | ata | gtg | tct | gca | ctg | ctt | ggg | gac | cat | tat | gtg | 4059 |
| Glu | Val | Glu | Gln | Ile | Val | Ser | Ala | Leu | Leu | Gly | Asp | His | Tyr | Val | |
| 1340 | | | | 1345 | | | | | 1350 | | | | | | |
| cag | ctg | cca | gca | acc | tac | atg | aac | ctg | ggc | ccc | agc | acc | tca | cat | 4104 |
| Gln | Leu | Pro | Ala | Thr | Tyr | Met | Asn | Leu | Gly | Pro | Ser | Thr | Ser | His | |
| 1355 | | | | 1360 | | | | | 1365 | | | | | | |
| gag | atg | aat | gtg | cat | cca | gaa | cag | cag | cag | tcc | tca | ccc | atg | cca | 4149 |
| Glu | Met | Asn | Val | His | Pro | Glu | Gln | Gln | Gln | Ser | Ser | Pro | Met | Pro | |
| 1370 | | | | 1375 | | | | | 1380 | | | | | | |
| ggg | agt | gca | cac | cga | ccc | cgg | cca | ctc | tca | gag | cct | cct | cgg | ccc | 4194 |
| Gly | Ser | Ala | His | Arg | Pro | Arg | Pro | Leu | Ser | Glu | Pro | Pro | Arg | Pro | |
| 1385 | | | | 1390 | | | | | 1395 | | | | | | |
| act | tga | | | | | | | | | | | | | | 4200 |
| Thr | | | | | | | | | | | | | | | |

<210> SEQ ID NO 37
<211> LENGTH: 1399
<212> TYPE: PRT
<213> ORGANISM: Macaca fascicularis

<400> SEQUENCE: 37

Met Glu Leu Leu Pro Pro Leu Pro Gln Ser Phe Leu Leu Leu Leu Leu
1               5                   10                  15

Leu Pro Ala Lys Pro Ala Ala Ala Lys Glu Trp Gln Cys Pro Arg Thr
            20                  25                  30

Pro Tyr Ala Ala Ser Arg Asp Phe Asn Val Lys Tyr Met Val Pro Ser
        35                  40                  45

Phe Ser Ala Gly Gly Leu Val Gln Thr Met Val Thr Tyr Gln Gly Asp
    50                  55                  60

Lys Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Ser Gly Asp Thr Asp Thr Lys Val Leu Val Leu Glu Pro Ala
        115                 120                 125

Leu Pro Ala Leu Val Ser Cys Gly Ser Ser Leu Gln Gly Arg Cys Phe
    130                 135                 140

Leu His Asp Leu Asp Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

-continued

```
Gln Ala Ser Tyr Phe Tyr Val Ala Ser Ser Leu Asp Ala Val Ala
        195                 200                 205

Ala Ser Phe Ser Pro Arg Ser Val Ser Ile Arg Arg Leu Lys Ala Asp
210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Ala
            260                 265                 270

Pro Gly Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
290                 295                 300

Lys Arg Arg Arg Gly Ala Pro Glu Gly Gly Gln Pro Tyr Pro Val
305                 310                 315                 320

Leu Arg Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Ala
            340                 345                 350

Gly Lys Asp Ser Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Pro
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Thr Val Glu Val
        435                 440                 445

Thr Ala Leu Tyr Val Thr Arg Leu Asp Asn Val Thr Val Ala His Met
450                 455                 460

Gly Thr Ala Asp Gly Arg Ile Leu Gln Val Glu Leu Ala Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Phe Phe Ala
            500                 505                 510

Ser Gly Asp Gln Val Phe Gln Val Pro Ile Gln Gly Pro Gly Cys Arg
        515                 520                 525

His Phe Leu Thr Cys Gly Arg Cys Leu Arg Ala Gln Arg Phe Met Gly
    530                 535                 540

Cys Gly Trp Cys Gly Asn Met Cys Gly Arg Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Ile Thr Val Gly Gln Ser Pro Cys Arg Pro Leu Pro Lys Asp Ser Ser
```

```
              610                 615                 620
Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
                660                 665                 670

Thr Ser Met Leu Arg Gly Phe Phe Met Glu Pro Val Leu Ile Ala
            675                 680                 685

Val Gln Pro Leu Phe Gly Pro Arg Ala Gly Thr Cys Leu Thr Leu
690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Met Val Ala Ser Val Pro Leu Ser Leu Gln
                740                 745                 750

Val Gly Gly Ala Gln Val Pro Gly Ser Trp Thr Phe His Tyr Arg Glu
            755                 760                 765

Asp Pro Val Val Leu Ser Ile Ser Pro Asn Cys Gly Tyr Ser Asn Ser
770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Gln
                820                 825                 830

Asp Pro Gln Gly Trp Val Ala Gly Asn Leu Ser Ala Trp Gly Asp Gly
            835                 840                 845

Ala Ala Gly Phe Thr Leu Pro Gly Phe Arg Phe Leu Thr Pro Pro His
            850                 855                 860

Pro Pro Ser Ala Asn Leu Ile Pro Leu Lys Pro Glu Glu His Ala Ile
865                 870                 875                 880

Lys Phe Glu Tyr Ile Gly Leu Gly Ala Val Thr Asp Cys Val Gly Val
                885                 890                 895

Asn Val Thr Val Gly Gly Glu Ser Cys Gln His Glu Phe Arg Gly Asp
                900                 905                 910

Met Val Val Cys Pro Leu Pro Pro Ser Leu Gln Leu Gly Lys Asp Gly
            915                 920                 925

Ala Pro Leu Gln Val Cys Val Asp Gly Glu Cys His Ile Leu Gly Arg
            930                 935                 940

Val Val Trp Pro Gly Pro Asp Gly Val Pro Gln Ser Thr Leu Leu Gly
945                 950                 955                 960

Ile Leu Leu Pro Leu Leu Leu Val Ala Ala Leu Ala Thr Ala Leu
                965                 970                 975

Val Phe Ser Tyr Trp Trp Gln Arg Lys Gln Leu Val Leu Pro Pro Asn
            980                 985                 990

Leu Asp Asp Leu Ala Ser Leu Asp  Gln Thr Thr Gly Ala  Thr Pro Leu
            995                 1000                 1005

Pro Ile Leu Tyr Ser Gly Ser  Asp Tyr Arg Ser Gly  Leu Ala Arg
    1010                 1015                 1020

Pro Ala  Thr Asp Gly Leu Asp  Ser Thr Cys Val His  Gly Ala Ser
    1025                 1030                 1035
```

Phe Ser Asn Ser Glu Asp Glu Ser Cys Val Pro Leu Leu Arg Lys
1040                1045                1050

Glu Ser Ile Gln Leu Arg Asp Leu Asp Ser Ala Leu Leu Ala Glu
1055                1060                1065

Val Lys Asp Val Leu Ile Pro His Glu Arg Val Val Ala His Ser
1070                1075                1080

Asp Arg Val Ile Gly Lys Gly His Phe Gly Val Val Tyr His Gly
1085                1090                1095

Glu Tyr Ile Asp Gln Ala Gln Asn Arg Ile Gln Cys Ala Ile Lys
1100                1105                1110

Ser Leu Ser Arg Ile Thr Glu Met Gln Gln Val Glu Ala Phe Leu
1115                1120                1125

Arg Glu Gly Leu Leu Met Arg Gly Leu Asn His Pro Asn Val Leu
1130                1135                1140

Ala Leu Ile Gly Ile Met Leu Pro Pro Glu Gly Leu Pro His Val
1145                1150                1155

Leu Leu Pro Tyr Met Cys His Gly Asp Leu Leu Gln Phe Ile Arg
1160                1165                1170

Ser Pro Gln Arg Asn Pro Thr Val Lys Asp Leu Ile Ser Phe Gly
1175                1180                1185

Leu Gln Val Ala His Gly Met Glu Tyr Leu Ala Glu Gln Lys Phe
1190                1195                1200

Val His Arg Asp Leu Ala Ala Arg Asn Cys Met Leu Asp Glu Ser
1205                1210                1215

Phe Thr Val Lys Val Ala Asp Phe Gly Leu Ala Arg Asp Ile Leu
1220                1225                1230

Asp Lys Glu Tyr Tyr Ser Val Gln Gln His Arg His Ala Arg Leu
1235                1240                1245

Pro Val Lys Trp Met Ala Leu Glu Ser Leu Gln Thr Tyr Arg Phe
1250                1255                1260

Thr Thr Lys Ser Asp Val Trp Ser Phe Gly Val Leu Leu Trp Glu
1265                1270                1275

Leu Leu Thr Arg Gly Ala Pro Pro Tyr Pro His Ile Asp Pro Phe
1280                1285                1290

Asp Leu Thr His Phe Leu Ala Gln Gly Arg Arg Leu Pro Gln Pro
1295                1300                1305

Glu Tyr Cys Pro Asn Ser Leu Tyr Gln Val Met Gln Gln Cys Trp
1310                1315                1320

Glu Ala Asp Pro Ala Ala Arg Pro Thr Phe Gly Val Leu Val Gly
1325                1330                1335

Glu Val Glu Gln Ile Val Ser Ala Leu Leu Gly Asp His Tyr Val
1340                1345                1350

Gln Leu Pro Ala Thr Tyr Met Asn Leu Gly Pro Ser Thr Ser His
1355                1360                1365

Glu Met Asn Val His Pro Glu Gln Gln Gln Ser Ser Pro Met Pro
1370                1375                1380

Gly Ser Ala His Arg Pro Arg Pro Leu Ser Glu Pro Pro Arg Pro
1385                1390                1395

Thr

<210> SEQ ID NO 38
<211> LENGTH: 23
<212> TYPE: DNA

```
<213> ORGANISM: Artificial Sequence
<220> FEATURE:
<223> OTHER INFORMATION: PCR forward primer for human MST1R

<400> SEQUENCE: 38
gaggactggc agtgcccgcg cac                                              23

<210> SEQ ID NO 39
<211> LENGTH: 23
<212> TYPE: DNA
<213> ORGANISM: Artificial Sequence
<220> FEATURE:
<223> OTHER INFORMATION: PCR reverse primer for human MST1R

<400> SEQUENCE: 39
tcaagtgggc cgaggaggct ctg                                              23

<210> SEQ ID NO 40
<211> LENGTH: 24
<212> TYPE: DNA
<213> ORGANISM: Artificial Sequence
<220> FEATURE:
<223> OTHER INFORMATION: PCR forward primer for cynomolgus monkey MST1R

<400> SEQUENCE: 40
aaggaatggc agtgcccgcg cacc                                             24

<210> SEQ ID NO 41
<211> LENGTH: 25
<212> TYPE: DNA
<213> ORGANISM: Artificial Sequence
<220> FEATURE:
<223> OTHER INFORMATION: PCR forward primer for mouse MST1R

<400> SEQUENCE: 41
tcaagtgggc cgaggaggct ctgag                                            25

<210> SEQ ID NO 42
<211> LENGTH: 23
<212> TYPE: DNA
<213> ORGANISM: Artificial Sequence
<220> FEATURE:
<223> OTHER INFORMATION: PCR forward primer for mouse MST1R

<400> SEQUENCE: 42
tccaccaacc tgaactggca gtg                                              23

<210> SEQ ID NO 43
<211> LENGTH: 23
<212> TYPE: DNA
<213> ORGANISM: Artificial Sequence
<220> FEATURE:
<223> OTHER INFORMATION: PCR reverse primer for mouse MST1R

<400> SEQUENCE: 43
tcaagtgggc agggtggct ctg                                               23

<210> SEQ ID NO 44
<211> LENGTH: 4785
<212> TYPE: DNA
<213> ORGANISM: Homo sapiens
<220> FEATURE:
<221> NAME/KEY: CDS
<222> LOCATION: (265)..(4467)

<400> SEQUENCE: 44
```

-continued

```
agtgtacagc ggcggctggg gcggcaggtg aggcggctgg ggcgttgctg tcgtgcgtcc      60
gcaggcgtca ggtgctcaga cccgagggcc gggaagggat ttgggtttca caggaacctg     120 gggcggggt ccgctatctt ggggctgtcg ggaccgctgc ttaaatttgg cccagtccag      180
acctcgagtc gggcccccag ccaggcccac gccaggtcc aggcccaggc cggtagggat      240
cctctagggt cccagctcgc ctcg atg gag ctc ctc ccg ccg ctg cct cag        291
                            Met Glu Leu Leu Pro Pro Leu Pro Gln
                              1               5 tcc ttc ctg ttg ctg ctg ttg cct gcc aag ccc gcg gcg ggc gag           339
Ser Phe Leu Leu Leu Leu Leu Pro Ala Lys Pro Ala Ala Gly Glu
 10              15                  20                  25 gac tgg cag tgc ccg cgc acc ccc tac gcg gcc tct cgc gac ttt gac       387
Asp Trp Gln Cys Pro Arg Thr Pro Tyr Ala Ala Ser Arg Asp Phe Asp
                30                  35                  40 gtg aag tac gtg gtg ccc agc ttc tcc gcc gga ggc ctg gta cag gcc       435
Val Lys Tyr Val Val Pro Ser Phe Ser Ala Gly Gly Leu Val Gln Ala
            45                  50                  55 atg gtg acc tac gag ggc gac aga aat gag agt gct gtg ttt gta gcc       483
Met Val Thr Tyr Glu Gly Asp Arg Asn Glu Ser Ala Val Phe Val Ala
         60                  65                  70 ata cgc aat cgc ctg cat gtg ctt ggg cct gac ctg aag tct gtc cag       531
Ile Arg Asn Arg Leu His Val Leu Gly Pro Asp Leu Lys Ser Val Gln
 75                  80                  85 agc ctg gcc acg ggc cct gct gga gac cct ggc tgc cag acg tgt gca       579
Ser Leu Ala Thr Gly Pro Ala Gly Asp Pro Gly Cys Gln Thr Cys Ala
 90                  95                 100                 105 gcc tgt ggc cca gga ccc cac ggc cct ccc ggt gac aca gac aca aag       627
Ala Cys Gly Pro Gly Pro His Gly Pro Pro Gly Asp Thr Asp Thr Lys
                110                 115                 120 gtg ctg gtg ctg gat ccc gcg ctg cct gcg ctg gtc agt tgt ggc tcc       675
Val Leu Val Leu Asp Pro Ala Leu Pro Ala Leu Val Ser Cys Gly Ser
            125                 130                 135 agc ctg cag ggc cgc tgc ttc ctg cat gac cta gag ccc caa ggg aca       723
Ser Leu Gln Gly Arg Cys Phe Leu His Asp Leu Glu Pro Gln Gly Thr
        140                 145                 150 gcc gtg cat ctg gca gcg cca gcc tgc ctc ttc tca gcc cac cat aac       771
Ala Val His Leu Ala Ala Pro Ala Cys Leu Phe Ser Ala His His Asn
 155                 160                 165 cgg ccc gat gac tgc ccc gac tgt gtg gcc agc cca ttg ggc acc cgt       819
Arg Pro Asp Asp Cys Pro Asp Cys Val Ala Ser Pro Leu Gly Thr Arg
170                 175                 180                 185 gta act gtg gtt gag caa ggc cag gcc tcc tat ttc tac gtg gca tcc       867
Val Thr Val Val Glu Gln Gly Gln Ala Ser Tyr Phe Tyr Val Ala Ser
                190                 195                 200 tca ctg gac gca gcc gtg gct gcc agc ttc agc cca cgc tca gtg tct       915
Ser Leu Asp Ala Ala Val Ala Ala Ser Phe Ser Pro Arg Ser Val Ser
            205                 210                 215 atc agg cgt ctc aag gct gac gcc tcg gga ttc gca ccg ggc ttt gtg       963
Ile Arg Arg Leu Lys Ala Asp Ala Ser Gly Phe Ala Pro Gly Phe Val
        220                 225                 230 gcg ttg tca gtg ctg ccc aag cat ctt gtc tcc tac agt att gaa tac      1011
Ala Leu Ser Val Leu Pro Lys His Leu Val Ser Tyr Ser Ile Glu Tyr
 235                 240                 245 gtg cac agc ttc cac acg gga gcc ttc gta tac ttc ctg act gta cag      1059
Val His Ser Phe His Thr Gly Ala Phe Val Tyr Phe Leu Thr Val Gln
250                 255                 260                 265 ccg gcc agc gtg aca gat gat cct agt gcc ctg cac aca cgc ctg gca      1107
Pro Ala Ser Val Thr Asp Asp Pro Ser Ala Leu His Thr Arg Leu Ala
                270                 275                 280
```

```
cgg ctt agc gcc act gag cca gag ttg ggt gac tat cgg gag ctg gtc    1155
Arg Leu Ser Ala Thr Glu Pro Glu Leu Gly Asp Tyr Arg Glu Leu Val
            285                 290                 295 ctc gac tgc aga ttt gct cca aaa cgc agg cgc cgg ggg gcc cca gaa    1203
Leu Asp Cys Arg Phe Ala Pro Lys Arg Arg Arg Arg Gly Ala Pro Glu
        300                 305                 310 ggc gga cag ccc tac cct gtg ctg cgg gtg gcc cac tcc gct cca gtg    1251
Gly Gly Gln Pro Tyr Pro Val Leu Arg Val Ala His Ser Ala Pro Val
            315                 320                 325 ggt gcc caa ctt gcc act gag ctg agc atc gcc gag ggc cag gaa gta    1299
Gly Ala Gln Leu Ala Thr Glu Leu Ser Ile Ala Glu Gly Gln Glu Val
330                 335                 340                 345 cta ttt ggg gtc ttt gtg act ggc aag gat ggt ggt cct ggc gtg ggc    1347
Leu Phe Gly Val Phe Val Thr Gly Lys Asp Gly Gly Pro Gly Val Gly
                350                 355                 360 ccc aac tct gtc gtc tgt gcc ttc ccc att gac ctg ctg gac aca cta    1395
Pro Asn Ser Val Val Cys Ala Phe Pro Ile Asp Leu Leu Asp Thr Leu
                365                 370                 375 att gat gag ggt gtg gag cgc tgt tgt gaa tcc cca gtc cat cca ggc    1443
Ile Asp Glu Gly Val Glu Arg Cys Cys Glu Ser Pro Val His Pro Gly
            380                 385                 390 ctc cgg cga ggc ctc gac ttc ttc cag tcg ccc agt ttt tgc ccc aac    1491
Leu Arg Arg Gly Leu Asp Phe Phe Gln Ser Pro Ser Phe Cys Pro Asn
            395                 400                 405 ccg cct ggc ctg gaa gcc ctc agc ccc aac acc agc tgc cgc cac ttc    1539
Pro Pro Gly Leu Glu Ala Leu Ser Pro Asn Thr Ser Cys Arg His Phe
410                 415                 420                 425 cct ctg ctg gtc agt agc agc ttc tca cgt gtg gac cta ttc aat ggg    1587
Pro Leu Leu Val Ser Ser Ser Phe Ser Arg Val Asp Leu Phe Asn Gly
                430                 435                 440 ctg ttg gga cca gta cag gtc act gca ttg tat gtg aca cgc ctt gac    1635
Leu Leu Gly Pro Val Gln Val Thr Ala Leu Tyr Val Thr Arg Leu Asp
                445                 450                 455 aac gtc aca gtg gca cac atg ggc aca atg gat ggg cgt atc ctg cag    1683
Asn Val Thr Val Ala His Met Gly Thr Met Asp Gly Arg Ile Leu Gln
            460                 465                 470 gtg gag ctg gtc agg tca cta aac tac ttg ctg tat gtg tcc aac ttc    1731
Val Glu Leu Val Arg Ser Leu Asn Tyr Leu Leu Tyr Val Ser Asn Phe
475                 480                 485 tca ctg ggt gac agt ggg cag ccc gtg cag cgg gat gtc agt cgt ctt    1779
Ser Leu Gly Asp Ser Gly Gln Pro Val Gln Arg Asp Val Ser Arg Leu
490                 495                 500                 505 ggg gac cac cta ctc ttt gcc tct ggg gac cag gtt ttc cag gta cct    1827
Gly Asp His Leu Leu Phe Ala Ser Gly Asp Gln Val Phe Gln Val Pro
                510                 515                 520 atc caa ggc cct ggc tgc cgc cac ttc ctg acc tgt ggg cgt tgc cta    1875
Ile Gln Gly Pro Gly Cys Arg His Phe Leu Thr Cys Gly Arg Cys Leu
            525                 530                 535 agg gca tgg cat ttc atg ggc tgt ggc tgg tgt ggg aac atg tgc ggc    1923
Arg Ala Trp His Phe Met Gly Cys Gly Trp Cys Gly Asn Met Cys Gly
            540                 545                 550 cag cag aag gag tgt cct ggc tcc tgg caa cag gac cac tgc cca cct    1971
Gln Gln Lys Glu Cys Pro Gly Ser Trp Gln Gln Asp His Cys Pro Pro
            555                 560                 565 aag ctt act gag ttc cac ccc cac agt gga cct cta agg ggc agt aca    2019
Lys Leu Thr Glu Phe His Pro His Ser Gly Pro Leu Arg Gly Ser Thr
570                 575                 580                 585 agg ctg acc ctg tgt ggc tcc aac ttc tac ctt cac cct tct ggt ctg    2067
Arg Leu Thr Leu Cys Gly Ser Asn Phe Tyr Leu His Pro Ser Gly Leu
```

-continued

```
                  590                 595                 600
gtg cct gag gga acc cat cag gtc act gtg ggc caa agt ccc tgc cgg       2115
Val Pro Glu Gly Thr His Gln Val Thr Val Gly Gln Ser Pro Cys Arg
            605                 610                 615 cca ctg ccc aag gac agc tca aaa ctc aga cca gtg ccc cgg aaa gac       2163
Pro Leu Pro Lys Asp Ser Ser Lys Leu Arg Pro Val Pro Arg Lys Asp
        620                 625                 630 ttt gta gag gag ttt gag tgt gaa ctg gag ccc ttg ggc acc cag gca       2211
Phe Val Glu Glu Phe Glu Cys Glu Leu Glu Pro Leu Gly Thr Gln Ala
    635                 640                 645 gtg ggg cct acc aac gtc agc ctc acc gtg act aac atg cca ccg ggc       2259
Val Gly Pro Thr Asn Val Ser Leu Thr Val Thr Asn Met Pro Pro Gly
650                 655                 660                 665 aag cac ttc cgg gta gac ggc acc tcc gtg ctg aga ggc ttc tct ttc       2307
Lys His Phe Arg Val Asp Gly Thr Ser Val Leu Arg Gly Phe Ser Phe
                670                 675                 680 atg gag cca gtg ctg ata gca gtg caa ccc ctc ttt ggc cca cgg gca       2355
Met Glu Pro Val Leu Ile Ala Val Gln Pro Leu Phe Gly Pro Arg Ala
            685                 690                 695 gga ggc acc tgt ctc act ctt gaa ggc cag agt ctg tct gta ggc acc       2403
Gly Gly Thr Cys Leu Thr Leu Glu Gly Gln Ser Leu Ser Val Gly Thr
        700                 705                 710 agc cgg gct gtg ctg gtc aat ggg act gag tgt ctg cta gca cgg gtc       2451
Ser Arg Ala Val Leu Val Asn Gly Thr Glu Cys Leu Leu Ala Arg Val
    715                 720                 725 agt gag ggg cag ctt tta tgt gcc aca ccc cct ggg gcc acg gtg gcc       2499
Ser Glu Gly Gln Leu Leu Cys Ala Thr Pro Pro Gly Ala Thr Val Ala
730                 735                 740                 745 agt gtc ccc ctt agc ctg cag gtg ggg ggt gcc cag gta cct ggt tcc       2547
Ser Val Pro Leu Ser Leu Gln Val Gly Gly Ala Gln Val Pro Gly Ser
                750                 755                 760 tgg acc ttc cag tac aga gaa gac cct gtc gtg cta agc atc agc ccc       2595
Trp Thr Phe Gln Tyr Arg Glu Asp Pro Val Val Leu Ser Ile Ser Pro
            765                 770                 775 aac tgt ggc tac atc aac tcc cac atc acc atc tgt ggc cag cat cta       2643
Asn Cys Gly Tyr Ile Asn Ser His Ile Thr Ile Cys Gly Gln His Leu
        780                 785                 790 act tca gca tgg cac tta gtg ctg tca ttc cat gac ggg ctt agg gca       2691
Thr Ser Ala Trp His Leu Val Leu Ser Phe His Asp Gly Leu Arg Ala
    795                 800                 805 gtg gaa agc agg tgt gag agg cag ctt cca gag cag cag ctg tgc cgc       2739
Val Glu Ser Arg Cys Glu Arg Gln Leu Pro Glu Gln Gln Leu Cys Arg
810                 815                 820                 825 ctt cct gaa tat gtg gtc cga gac ccc cag gga tgg gtg gca ggg aat       2787
Leu Pro Glu Tyr Val Val Arg Asp Pro Gln Gly Trp Val Ala Gly Asn
                830                 835                 840 ctg agt gcc cga ggg gat gga gct gct ggc ttt aca ctg cct ggc ttt       2835
Leu Ser Ala Arg Gly Asp Gly Ala Ala Gly Phe Thr Leu Pro Gly Phe
            845                 850                 855 cgc ttc cta ccc cca ccc cat cca ccc agt gcc aac cta gtt cca ctg       2883
Arg Phe Leu Pro Pro Pro His Pro Pro Ser Ala Asn Leu Val Pro Leu
        860                 865                 870 aag cct gag gag cat gcc att aag ttt gag tat att ggg ctg ggc gct       2931
Lys Pro Glu Glu His Ala Ile Lys Phe Glu Tyr Ile Gly Leu Gly Ala
    875                 880                 885 gtg gct gac tgt gtg ggt atc aac gtg acc gtg ggt ggt gag agc tgc       2979
Val Ala Asp Cys Val Gly Ile Asn Val Thr Val Gly Gly Glu Ser Cys
890                 895                 900                 905 cag cac gag ttc cgg ggg gac atg gtt gtc tgc ccc ctg ccc cca tcc       3027
```

|  |  |
|---|---:|
| Gln His Glu Phe Arg Gly Asp Met Val Val Cys Pro Leu Pro Pro Ser<br>          910                      915                    920 |  |
| ctg cag ctt ggc cag gat ggt gcc cca ttg cag gtc tgc gta gat ggt<br>Leu Gln Leu Gly Gln Asp Gly Ala Pro Leu Gln Val Cys Val Asp Gly<br>          925                      930                    935 | 3075 |
| gaa tgt cat atc ctg ggt aga gtg gtg cgg cca ggg cca gat ggg gtc<br>Glu Cys His Ile Leu Gly Arg Val Val Arg Pro Gly Pro Asp Gly Val<br>          940                      945                    950 | 3123 |
| cca cag agc acg ctc ctt ggt atc ctg ctg cct ttg ctg ctg ctt gtg<br>Pro Gln Ser Thr Leu Leu Gly Ile Leu Leu Pro Leu Leu Leu Leu Val<br>955                      960                    965 | 3171 |
| gct gca ctg gcg act gca ctg gtc ttc agc tac tgg tgg cgg agg aag<br>Ala Ala Leu Ala Thr Ala Leu Val Phe Ser Tyr Trp Trp Arg Arg Lys<br>970                      975                    980                    985 | 3219 |
| cag cta gtt ctt cct ccc aac ctg aat gac ctg gca tcc ctg gac cag<br>Gln Leu Val Leu Pro Pro Asn Leu Asn Asp Leu Ala Ser Leu Asp Gln<br>          990                      995                    1000 | 3267 |
| act gct gga gcc aca ccc ctg cct att ctg tac tcg ggc tct gac<br>Thr Ala Gly Ala Thr Pro Leu Pro Ile Leu Tyr Ser Gly Ser Asp<br>                1005                    1010                    1015 | 3312 |
| tac aga agt ggc ctt gca ctc cct gcc att gat ggt ctg gat tcc<br>Tyr Arg Ser Gly Leu Ala Leu Pro Ala Ile Asp Gly Leu Asp Ser<br>                1020                    1025                    1030 | 3357 |
| acc act tgt gtc cat gga gca tcc ttc tcc gat agt gaa gat gaa<br>Thr Thr Cys Val His Gly Ala Ser Phe Ser Asp Ser Glu Asp Glu<br>                1035                    1040                    1045 | 3402 |
| tcc tgt gtg cca ctg ctg cgg aaa gag tcc atc cag cta agg gac<br>Ser Cys Val Pro Leu Leu Arg Lys Glu Ser Ile Gln Leu Arg Asp<br>                1050                    1055                    1060 | 3447 |
| ctg gac tct gcg ctc ttg gct gag gtc aag gat gtg ctg att ccc<br>Leu Asp Ser Ala Leu Leu Ala Glu Val Lys Asp Val Leu Ile Pro<br>                1065                    1070                    1075 | 3492 |
| cat gag cgg gtg gtc acc cac agt gac cga gtc att ggc aaa ggc<br>His Glu Arg Val Val Thr His Ser Asp Arg Val Ile Gly Lys Gly<br>                1080                    1085                    1090 | 3537 |
| cac ttt gga gtt gtc tac cac gga gaa tac ata gac cag gcc cag<br>His Phe Gly Val Val Tyr His Gly Glu Tyr Ile Asp Gln Ala Gln<br>                1095                    1100                    1105 | 3582 |
| aat cga atc caa tgt gcc atc aag tca cta agt cgc atc aca gag<br>Asn Arg Ile Gln Cys Ala Ile Lys Ser Leu Ser Arg Ile Thr Glu<br>                1110                    1115                    1120 | 3627 |
| atg cag cag gtg gag gcc ttc ctg cga gag ggg ctg ctc atg cgt<br>Met Gln Gln Val Glu Ala Phe Leu Arg Glu Gly Leu Leu Met Arg<br>                1125                    1130                    1135 | 3672 |
| ggc ctg aac cac ccg aat gtg ctg gct ctc att ggt atc atg ttg<br>Gly Leu Asn His Pro Asn Val Leu Ala Leu Ile Gly Ile Met Leu<br>                1140                    1145                    1150 | 3717 |
| cca cct gag ggc ctg ccc cat gtg ctg ctg ccc tat atg tgc cac<br>Pro Pro Glu Gly Leu Pro His Val Leu Leu Pro Tyr Met Cys His<br>                1155                    1160                    1165 | 3762 |
| ggt gac ctg ctc cag ttc atc cgc tca cct cag cgg aac ccc acc<br>Gly Asp Leu Leu Gln Phe Ile Arg Ser Pro Gln Arg Asn Pro Thr<br>                1170                    1175                    1180 | 3807 |
| gtg aag gac ctc atc agc ttt ggc ctg cag gta gcc cgc ggc atg<br>Val Lys Asp Leu Ile Ser Phe Gly Leu Gln Val Ala Arg Gly Met<br>                1185                    1190                    1195 | 3852 |
| gag tac ctg gca gag cag aag ttt gtg cac agg gac ctg gct gcg<br>Glu Tyr Leu Ala Glu Gln Lys Phe Val His Arg Asp Leu Ala Ala<br>                1200                    1205                    1210 | 3897 |

| | | | | | | | | | | | | |
|---|---|---|---|---|---|---|---|---|---|---|---|---|
| cgg | aac | tgc | atg | ctg | gac | gag | tca | ttc | aca | gtc | aag | gtg | gct | gac | 3942 |
| Arg | Asn | Cys | Met | Leu | Asp | Glu | Ser | Phe | Thr | Val | Lys | Val | Ala | Asp | |
| | | | 1215 | | | | 1220 | | | | 1225 | | | | |

| ttt | ggt | ttg | gcc | cgc | gac | atc | ctg | gac | agg | gag | tac | tat | agt | gtt | 3987 |
| Phe | Gly | Leu | Ala | Arg | Asp | Ile | Leu | Asp | Arg | Glu | Tyr | Tyr | Ser | Val | |
| | | 1230 | | | | 1235 | | | | 1240 | | | | | |

| caa | cag | cat | cgc | cac | gct | cgc | cta | cct | gtg | aag | tgg | atg | gcg | ctg | 4032 |
| Gln | Gln | His | Arg | His | Ala | Arg | Leu | Pro | Val | Lys | Trp | Met | Ala | Leu | |
| | | 1245 | | | | 1250 | | | | 1255 | | | | | |

| gag | agc | ctg | cag | acc | tat | aga | ttt | acc | acc | aag | tct | gat | gtg | tgg | 4077 |
| Glu | Ser | Leu | Gln | Thr | Tyr | Arg | Phe | Thr | Thr | Lys | Ser | Asp | Val | Trp | |
| | | 1260 | | | | 1265 | | | | 1270 | | | | | |

| tca | ttt | ggt | gtg | ctg | ctg | tgg | gaa | ctg | ctg | aca | cgg | ggt | gcc | cca | 4122 |
| Ser | Phe | Gly | Val | Leu | Leu | Trp | Glu | Leu | Leu | Thr | Arg | Gly | Ala | Pro | |
| | | 1275 | | | | 1280 | | | | 1285 | | | | | |

| cca | tac | cgc | cac | att | gac | cct | ttt | gac | ctt | acc | cac | ttc | ctg | gcc | 4167 |
| Pro | Tyr | Arg | His | Ile | Asp | Pro | Phe | Asp | Leu | Thr | His | Phe | Leu | Ala | |
| | | 1290 | | | | 1295 | | | | 1300 | | | | | |

| cag | ggt | cgg | cgc | ctg | ccc | cag | cct | gag | tat | tgc | cct | gat | tct | ctg | 4212 |
| Gln | Gly | Arg | Arg | Leu | Pro | Gln | Pro | Glu | Tyr | Cys | Pro | Asp | Ser | Leu | |
| | | 1305 | | | | 1310 | | | | 1315 | | | | | |

| tac | caa | gtg | atg | cag | caa | tgc | tgg | gag | gca | gac | cca | gca | gtg | cga | 4257 |
| Tyr | Gln | Val | Met | Gln | Gln | Cys | Trp | Glu | Ala | Asp | Pro | Ala | Val | Arg | |
| | | 1320 | | | | 1325 | | | | 1330 | | | | | |

| ccc | acc | ttc | aga | gta | cta | gtg | ggg | gag | gtg | gag | cag | ata | gtg | tct | 4302 |
| Pro | Thr | Phe | Arg | Val | Leu | Val | Gly | Glu | Val | Glu | Gln | Ile | Val | Ser | |
| | | 1335 | | | | 1340 | | | | 1345 | | | | | |

| gca | ctg | ctt | ggg | gac | cat | tat | gtg | cag | ctg | cca | gca | acc | tac | atg | 4347 |
| Ala | Leu | Leu | Gly | Asp | His | Tyr | Val | Gln | Leu | Pro | Ala | Thr | Tyr | Met | |
| | | 1350 | | | | 1355 | | | | 1360 | | | | | |

| aac | ttg | ggc | ccc | agc | acc | tcg | cat | gag | atg | aat | gtg | cgt | cca | gaa | 4392 |
| Asn | Leu | Gly | Pro | Ser | Thr | Ser | His | Glu | Met | Asn | Val | Arg | Pro | Glu | |
| | | 1365 | | | | 1370 | | | | 1375 | | | | | |

| cag | ccg | cag | ttc | tca | ccc | atg | cca | ggg | aat | gta | cgc | cgg | ccc | cgg | 4437 |
| Gln | Pro | Gln | Phe | Ser | Pro | Met | Pro | Gly | Asn | Val | Arg | Arg | Pro | Arg | |
| | | 1380 | | | | 1385 | | | | 1390 | | | | | |

| cca | ctc | tca | gag | cct | cct | cgg | ccc | act | tga | cttagttctt | gggctggacc | 4487 |
| Pro | Leu | Ser | Glu | Pro | Pro | Arg | Pro | Thr | | | | |
| | | 1395 | | | | 1400 | | | | | | | tgcttagctg ccttgagcta accccaagct gcctctgggc catgccaggc cagagggcag 4547 tggccctcca ccttgttcct gcccttaac tttcagaggc aataggtaaa tggggcccat 4607 taggtccctc actccacaga gtgagccagt gagggcagtc ctgcaacatg tatttatgga 4667 gtgcctgctg tggaccctgt cttctgggca cagtggactc agcagtgacc acaccaacac 4727 tgacccttga accaataaag gaacaaatga ctattaaagc acaaaaaaaa aaaaaaaa 4785

<210> SEQ ID NO 45
<211> LENGTH: 1400
<212> TYPE: PRT
<213> ORGANISM: Homo sapiens

<400> SEQUENCE: 45

Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

-continued

Phe Ser Ala Gly Gly Leu Val Gln Ala Met Val Thr Tyr Glu Gly Asp
 50                  55                  60

Arg Asn Glu Ser Ala Val Phe Val Ala Ile Arg Asn Arg Leu His Val
 65                  70                  75                  80

Leu Gly Pro Asp Leu Lys Ser Val Gln Ser Leu Ala Thr Gly Pro Ala
                 85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
            115                 120                 125

Leu Pro Ala Leu Val Ser Cys Gly Ser Ser Leu Gln Gly Arg Cys Phe
130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
            195                 200                 205

Ala Ser Phe Ser Pro Arg Ser Val Ser Ile Arg Arg Leu Lys Ala Asp
210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
            275                 280                 285

Glu Leu Gly Asp Tyr Arg Glu Leu Val Leu Asp Cys Arg Phe Ala Pro
290                 295                 300

Lys Arg Arg Arg Arg Gly Ala Pro Glu Gly Gly Gln Pro Tyr Pro Val
305                 310                 315                 320

Leu Arg Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
            355                 360                 365

Phe Pro Ile Asp Leu Leu Asp Thr Leu Ile Asp Glu Gly Val Glu Arg
370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Gly Leu Glu Ala Leu
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
            435                 440                 445

Thr Ala Leu Tyr Val Thr Arg Leu Asp Asn Val Thr Val Ala His Met
450                 455                 460

Gly Thr Met Asp Gly Arg Ile Leu Gln Val Glu Leu Val Arg Ser Leu

```
                465                 470                 475                 480
            Asn Tyr Leu Leu Tyr Val Ser Asn Phe Ser Leu Gly Asp Ser Gly Gln
                                485                 490                 495

Pro Val Gln Arg Asp Val Ser Arg Leu Gly Asp His Leu Leu Phe Ala
                            500                 505                 510

Ser Gly Asp Gln Val Phe Gln Val Pro Ile Gln Pro Gly Cys Arg
                        515                 520                 525

His Phe Leu Thr Cys Gly Arg Cys Leu Arg Ala Trp His Phe Met Gly
                        530                 535                 540

Cys Gly Trp Cys Gly Asn Met Cys Gly Gln Gln Lys Glu Cys Pro Gly
            545                 550                 555                 560

Ser Trp Gln Gln Asp His Cys Pro Pro Lys Leu Thr Glu Phe His Pro
                                565                 570                 575

His Ser Gly Pro Leu Arg Gly Ser Thr Arg Leu Thr Leu Cys Gly Ser
                            580                 585                 590

Asn Phe Tyr Leu His Pro Ser Gly Leu Val Pro Glu Gly Thr His Gln
                        595                 600                 605

Val Thr Val Gly Gln Ser Pro Cys Arg Pro Leu Pro Lys Asp Ser Ser
                    610                 615                 620

Lys Leu Arg Pro Val Pro Arg Lys Asp Phe Val Glu Glu Phe Glu Cys
            625                 630                 635                 640

Glu Leu Glu Pro Leu Gly Thr Gln Ala Val Gly Pro Thr Asn Val Ser
                                645                 650                 655

Leu Thr Val Thr Asn Met Pro Pro Gly Lys His Phe Arg Val Asp Gly
                            660                 665                 670

Thr Ser Val Leu Arg Gly Phe Ser Phe Met Glu Pro Val Leu Ile Ala
                        675                 680                 685

Val Gln Pro Leu Phe Gly Pro Arg Ala Gly Gly Thr Cys Leu Thr Leu
                    690                 695                 700

Glu Gly Gln Ser Leu Ser Val Gly Thr Ser Arg Ala Val Leu Val Asn
            705                 710                 715                 720

Gly Thr Glu Cys Leu Leu Ala Arg Val Ser Glu Gly Gln Leu Leu Cys
                                725                 730                 735

Ala Thr Pro Pro Gly Ala Thr Val Ala Ser Val Pro Leu Ser Leu Gln
                            740                 745                 750

Val Gly Gly Ala Gln Val Pro Gly Ser Trp Thr Phe Gln Tyr Arg Glu
                        755                 760                 765

Asp Pro Val Val Leu Ser Ile Ser Pro Asn Cys Gly Tyr Ile Asn Ser
                    770                 775                 780

His Ile Thr Ile Cys Gly Gln His Leu Thr Ser Ala Trp His Leu Val
            785                 790                 795                 800

Leu Ser Phe His Asp Gly Leu Arg Ala Val Glu Ser Arg Cys Glu Arg
                                805                 810                 815

Gln Leu Pro Glu Gln Gln Leu Cys Arg Leu Pro Glu Tyr Val Val Arg
                            820                 825                 830

Asp Pro Gln Gly Trp Val Ala Gly Asn Leu Ser Ala Arg Gly Asp Gly
                        835                 840                 845

Ala Ala Gly Phe Thr Leu Pro Gly Phe Arg Phe Leu Pro Pro His His
                    850                 855                 860

Pro Pro Ser Ala Asn Leu Val Pro Leu Lys Pro Glu Glu His Ala Ile
            865                 870                 875                 880

Lys Phe Glu Tyr Ile Gly Leu Gly Ala Val Ala Asp Cys Val Gly Ile
                                885                 890                 895
```

```
Asn Val Thr Val Gly Gly Glu Ser Cys Gln His Glu Phe Arg Gly Asp
            900                 905                 910

Met Val Val Cys Pro Leu Pro Pro Ser Leu Gln Leu Gly Gln Asp Gly
            915                 920                 925

Ala Pro Leu Gln Val Cys Val Asp Gly Glu Cys His Ile Leu Gly Arg
        930                 935                 940

Val Val Arg Pro Gly Pro Asp Gly Val Pro Gln Ser Thr Leu Leu Gly
945                 950                 955                 960

Ile Leu Leu Pro Leu Leu Leu Val Ala Ala Leu Ala Thr Ala Leu
                965                 970                 975

Val Phe Ser Tyr Trp Trp Arg Arg Lys Gln Leu Val Leu Pro Pro Asn
        980                 985                 990

Leu Asn Asp Leu Ala Ser Leu Asp Gln Thr Ala Gly Ala Thr Pro Leu
            995                 1000                1005

Pro Ile Leu Tyr Ser Gly Ser Asp Tyr Arg Ser Gly Leu Ala Leu
    1010                1015                1020

Pro Ala Ile Asp Gly Leu Asp Ser Thr Thr Cys Val His Gly Ala
    1025                1030                1035

Ser Phe Ser Asp Ser Glu Asp Glu Ser Cys Val Pro Leu Leu Arg
    1040                1045                1050

Lys Glu Ser Ile Gln Leu Arg Asp Leu Asp Ser Ala Leu Leu Ala
    1055                1060                1065

Glu Val Lys Asp Val Leu Ile Pro His Glu Arg Val Val Thr His
    1070                1075                1080

Ser Asp Arg Val Ile Gly Lys Gly His Phe Gly Val Val Tyr His
    1085                1090                1095

Gly Glu Tyr Ile Asp Gln Ala Gln Asn Arg Ile Gln Cys Ala Ile
    1100                1105                1110

Lys Ser Leu Ser Arg Ile Thr Glu Met Gln Gln Val Glu Ala Phe
    1115                1120                1125

Leu Arg Glu Gly Leu Leu Met Arg Gly Leu Asn His Pro Asn Val
    1130                1135                1140

Leu Ala Leu Ile Gly Ile Met Leu Pro Pro Glu Gly Leu Pro His
    1145                1150                1155

Val Leu Leu Pro Tyr Met Cys His Gly Asp Leu Leu Gln Phe Ile
    1160                1165                1170

Arg Ser Pro Gln Arg Asn Pro Thr Val Lys Asp Leu Ile Ser Phe
    1175                1180                1185

Gly Leu Gln Val Ala Arg Gly Met Glu Tyr Leu Ala Glu Gln Lys
    1190                1195                1200

Phe Val His Arg Asp Leu Ala Ala Arg Asn Cys Met Leu Asp Glu
    1205                1210                1215

Ser Phe Thr Val Lys Val Ala Asp Phe Gly Leu Ala Arg Asp Ile
    1220                1225                1230

Leu Asp Arg Glu Tyr Tyr Ser Val Gln Gln His Arg His Ala Arg
    1235                1240                1245

Leu Pro Val Lys Trp Met Ala Leu Glu Ser Leu Gln Thr Tyr Arg
    1250                1255                1260

Phe Thr Thr Lys Ser Asp Val Trp Ser Phe Gly Val Leu Leu Trp
    1265                1270                1275

Glu Leu Leu Thr Arg Gly Ala Pro Pro Tyr Arg His Ile Asp Pro
    1280                1285                1290
```

| | | | | | | | | | | |
|---|---|---|---|---|---|---|---|---|---|---|
| Phe | Asp | Leu | Thr | His | Phe | Leu | Ala | Gln | Gly | Arg | Arg | Leu | Pro | Gln |
| 1295 | | | | 1300 | | | | | 1305 | |

| Pro | Glu | Tyr | Cys | Pro | Asp | Ser | Leu | Tyr | Gln | Val | Met | Gln | Gln | Cys |
|---|---|---|---|---|---|---|---|---|---|---|---|---|---|---|
| 1310 | | | | | 1315 | | | | | 1320 | |

| Trp | Glu | Ala | Asp | Pro | Ala | Val | Arg | Pro | Thr | Phe | Arg | Val | Leu | Val |
|---|---|---|---|---|---|---|---|---|---|---|---|---|---|---|
| 1325 | | | | | 1330 | | | | | 1335 | |

| Gly | Glu | Val | Glu | Gln | Ile | Val | Ser | Ala | Leu | Leu | Gly | Asp | His | Tyr |
|---|---|---|---|---|---|---|---|---|---|---|---|---|---|---|
| 1340 | | | | | 1345 | | | | | 1350 | |

| Val | Gln | Leu | Pro | Ala | Thr | Tyr | Met | Asn | Leu | Gly | Pro | Ser | Thr | Ser |
|---|---|---|---|---|---|---|---|---|---|---|---|---|---|---|
| 1355 | | | | | 1360 | | | | | 1365 | |

| His | Glu | Met | Asn | Val | Arg | Pro | Glu | Gln | Pro | Gln | Phe | Ser | Pro | Met |
|---|---|---|---|---|---|---|---|---|---|---|---|---|---|---|
| 1370 | | | | | 1375 | | | | | 1380 | |

| Pro | Gly | Asn | Val | Arg | Arg | Pro | Arg | Pro | Leu | Ser | Glu | Pro | Pro | Arg |
|---|---|---|---|---|---|---|---|---|---|---|---|---|---|---|
| 1385 | | | | | 1390 | | | | | 1395 | |

Pro Thr
1400

<210> SEQ ID NO 46
<211> LENGTH: 4720
<212> TYPE: DNA
<213> ORGANISM: Mus musculus
<220> FEATURE:
<221> NAME/KEY: CDS
<222> LOCATION: (257)..(4393)

<400> SEQUENCE: 46

```
gctgtagcag cggcagctag aagcagcagc tggggcccct ggtgaggtga tcgtgccatt        60
gccgtgtccg tgggtccaca gccaggtgct cagaccacaa gccagagaga aaggttgggt       120
ttgccaggga ccaggcaggg gggcagctg cccaggagct ttcagtaccg ctgcgtaaag       180
ctggtctcag ctcggaccct gagtctggtt cgatcaagtc ctggaccttc tgggattccc       240
aaggggcccc agctca atg ggg ctg cct ctg ccg ctg ctt caa tcc tct ctt      292
              Met Gly Leu Pro Leu Pro Leu Leu Gln Ser Ser Leu
                1               5                  10 ctg cta atg ctt ctt ttg cgg ctg tcg gcg gcg tcc acc aac ctg aac       340
Leu Leu Met Leu Leu Leu Arg Leu Ser Ala Ala Ser Thr Asn Leu Asn
        15                  20                  25 tgg cag tgc cca cga ata ccc tac gca gcc tcc cga gac ttc agt gtc       388
Trp Gln Cys Pro Arg Ile Pro Tyr Ala Ala Ser Arg Asp Phe Ser Val
 30                  35                  40 aag tac gtg gtc ccc agc ttc tcc gcg ggg ggc cgg gta cag gcc acc       436
Lys Tyr Val Val Pro Ser Phe Ser Ala Gly Gly Arg Val Gln Ala Thr
45                  50                  55                  60 gca gcc tac gag gac agt aca aat agt gcg gtg ttt gtg gcc aca cgc       484
Ala Ala Tyr Glu Asp Ser Thr Asn Ser Ala Val Phe Val Ala Thr Arg
                 65                  70                  75 aat cac ctg cac gtg ctt ggg cct gac ctg cag ttc ata gag aac ctg       532
Asn His Leu His Val Leu Gly Pro Asp Leu Gln Phe Ile Glu Asn Leu
             80                  85                  90 acc act ggc cct atc ggg aac cct ggc tgc cag act tgt gcg agc tgt       580
Thr Thr Gly Pro Ile Gly Asn Pro Gly Cys Gln Thr Cys Ala Ser Cys
         95                 100                 105 ggt cca ggc cct cat gga cca cca aag gac aca gac aca ctg gtg cta       628
Gly Pro Gly Pro His Gly Pro Pro Lys Asp Thr Asp Thr Leu Val Leu
     110                 115                 120 gtg atg gag cca ggt ttg cca gcc ctg gtc agc tgt ggc tca acc cta       676
Val Met Glu Pro Gly Leu Pro Ala Leu Val Ser Cys Gly Ser Thr Leu
125                 130                 135                 140
```

-continued

```
cag ggc cgc tgc ttc ctg cat gag ctg gag cct cgg ggg aaa gcc ctg      724
Gln Gly Arg Cys Phe Leu His Glu Leu Glu Pro Arg Gly Lys Ala Leu
            145                 150                 155 cac tta gca gct cca gcc tgc cta ttc tca gca aac aat aac aag cct      772
His Leu Ala Ala Pro Ala Cys Leu Phe Ser Ala Asn Asn Asn Lys Pro
        160                 165                 170 gag gcc tgc acg gac tgt gtg gct agc ccc ctg ggc act cgt gtg act      820
Glu Ala Cys Thr Asp Cys Val Ala Ser Pro Leu Gly Thr Arg Val Thr
    175                 180                 185 gtg gtg gag cag ggg cat gct tcc tac ttc tat gtg gca tct tcg cta      868
Val Val Glu Gln Gly His Ala Ser Tyr Phe Tyr Val Ala Ser Ser Leu
190                 195                 200 gac cca gag ttg gcc gct agc ttt agc ccc cgc tcg gtg tcc atc cgt      916
Asp Pro Glu Leu Ala Ala Ser Phe Ser Pro Arg Ser Val Ser Ile Arg
205                 210                 215                 220 cgt cta aag tct gat act tct gga ttc caa cca ggt ttt ccg tcg ctg      964
Arg Leu Lys Ser Asp Thr Ser Gly Phe Gln Pro Gly Phe Pro Ser Leu
            225                 230                 235 tcg gtg ctg ccc aaa tat ttg gcc tcc tac ctc atc aaa tat gtg tac     1012
Ser Val Leu Pro Lys Tyr Leu Ala Ser Tyr Leu Ile Lys Tyr Val Tyr
        240                 245                 250 agc ttc cac tcg ggg gat ttt gtc tac ttt ctg act gtc cag ccc atc     1060
Ser Phe His Ser Gly Asp Phe Val Tyr Phe Leu Thr Val Gln Pro Ile
    255                 260                 265 agt gtc aca agc cct ccc agt gcc ttg cat aca cgt ctg gtc cgg ctc     1108
Ser Val Thr Ser Pro Pro Ser Ala Leu His Thr Arg Leu Val Arg Leu
270                 275                 280 aat gct gta gag cca gag att ggt gac tac cgg gag ctg gtc ttg gac     1156
Asn Ala Val Glu Pro Glu Ile Gly Asp Tyr Arg Glu Leu Val Leu Asp
285                 290                 295                 300 tgt cat ttt gca cct aaa cgc cgg cgc cgt gga gcc ccg gag ggc aca     1204
Cys His Phe Ala Pro Lys Arg Arg Arg Arg Gly Ala Pro Glu Gly Thr
            305                 310                 315 cag ccc tac cca gtg ctt cag gca gcc cac tct gct cca gtg gat gcc     1252
Gln Pro Tyr Pro Val Leu Gln Ala Ala His Ser Ala Pro Val Asp Ala
        320                 325                 330 aaa ctg gct gtg gaa ctg agc att tca gag ggc cag gaa gtg ctt ttt     1300
Lys Leu Ala Val Glu Leu Ser Ile Ser Glu Gly Gln Glu Val Leu Phe
    335                 340                 345 ggg gtc ttt gtg acc gtc aag gat ggt ggc tct ggc atg ggt ccc aac     1348
Gly Val Phe Val Thr Val Lys Asp Gly Gly Ser Gly Met Gly Pro Asn
350                 355                 360 tct gtt gta tgt gcc ttc ccc att tac cac ctg aac atc ctg att gaa     1396
Ser Val Val Cys Ala Phe Pro Ile Tyr His Leu Asn Ile Leu Ile Glu
365                 370                 375                 380 gag ggt gtc gaa tat tgc tgt cac tct tca aat tct tct tcc ctg ttg     1444
Glu Gly Val Glu Tyr Cys Cys His Ser Ser Asn Ser Ser Ser Leu Leu
            385                 390                 395 tcg aga ggc ctt gac ttc ttc cag acg ccc agt ttt tgt cct aat ccg     1492
Ser Arg Gly Leu Asp Phe Phe Gln Thr Pro Ser Phe Cys Pro Asn Pro
        400                 405                 410 cct ggt gga gag gcc tcc ggc ccc agc tcc cgt tgc cac tac ttc cct     1540
Pro Gly Gly Glu Ala Ser Gly Pro Ser Ser Arg Cys His Tyr Phe Pro
    415                 420                 425 ttg atg gtc cac gct agc ttc acc cgt gtg gac ctc ttc aat gga ctg     1588
Leu Met Val His Ala Ser Phe Thr Arg Val Asp Leu Phe Asn Gly Leu
430                 435                 440 tta gga tca gtg aag gtc acc gca ctg cat gtg aca cgt ctt ggc aat     1636
Leu Gly Ser Val Lys Val Thr Ala Leu His Val Thr Arg Leu Gly Asn
445                 450                 455                 460
```

| | | |
|---|---|---|
| gtt aca gtg gcc cac atg ggc act gtg gat ggg cgt gtc cta cag gtg<br>Val Thr Val Ala His Met Gly Thr Val Asp Gly Arg Val Leu Gln Val<br>465                     470                  475 | | 1684 |
| gag ata gcc agg tca ctc aac tac ctg ctg tat gtg tcc aac ttc tcc<br>Glu Ile Ala Arg Ser Leu Asn Tyr Leu Leu Tyr Val Ser Asn Phe Ser<br>480                   485                   490 | | 1732 |
| ctg ggc agc agt gga cag cct gtt cat cgg gat gtc agc cgc ctc ggg<br>Leu Gly Ser Ser Gly Gln Pro Val His Arg Asp Val Ser Arg Leu Gly<br>495                     500                  505 | | 1780 |
| aat gac cta ctc ttt gcc tct ggg gac cag gtc ttc aag gtg ccc atc<br>Asn Asp Leu Leu Phe Ala Ser Gly Asp Gln Val Phe Lys Val Pro Ile<br>510                   515                 520 | | 1828 |
| cag ggc cct ggc tgt cgt cat ttt ctc acc tgt tgg cgt tgc ctg aga<br>Gln Gly Pro Gly Cys Arg His Phe Leu Thr Cys Trp Arg Cys Leu Arg<br>525             530                  535                  540 | | 1876 |
| gca cag cgc ttc atg gga tgt ggc tgg tgt ggg gac cgg tgt gac cgg<br>Ala Gln Arg Phe Met Gly Cys Gly Trp Cys Gly Asp Arg Cys Asp Arg<br>                   545                  550                  555 | | 1924 |
| cag aag gag tgt cct ggc tcc tgg caa cag gac cac tgt ccg cct gag<br>Gln Lys Glu Cys Pro Gly Ser Trp Gln Gln Asp His Cys Pro Pro Glu<br>560                   565                   570 | | 1972 |
| atc agt gag ttc tat cct cac agc ggg cct cta agg ggc act acg agg<br>Ile Ser Glu Phe Tyr Pro His Ser Gly Pro Leu Arg Gly Thr Thr Arg<br>575                     580                  585 | | 2020 |
| ctc acc ctt tgt ggc tcc aac ttc tac ctg cga cct gat gat gtc gta<br>Leu Thr Leu Cys Gly Ser Asn Phe Tyr Leu Arg Pro Asp Asp Val Val<br>590                   595                   600 | | 2068 |
| cct gag gga aca cac cag atc acc gtg ggc caa agt ccc tgc cga ctg<br>Pro Glu Gly Thr His Gln Ile Thr Val Gly Gln Ser Pro Cys Arg Leu<br>605             610                  615                  620 | | 2116 |
| ctg cct aag gac tct tca agc cct agg cca ggg tcc ctc aag gaa ttc<br>Leu Pro Lys Asp Ser Ser Ser Pro Arg Pro Gly Ser Leu Lys Glu Phe<br>                   625                  630                  635 | | 2164 |
| ata cag gaa ctt gaa tgt gag ctg gag ccc ctg gtc acc cag gca gtg<br>Ile Gln Glu Leu Glu Cys Glu Leu Glu Pro Leu Val Thr Gln Ala Val<br>640                   645                   650 | | 2212 |
| ggg act aca aac atc agc ctt gtc atc acc aac atg cca gca ggc aag<br>Gly Thr Thr Asn Ile Ser Leu Val Ile Thr Asn Met Pro Ala Gly Lys<br>655                     660                   665 | | 2260 |
| cac ttc cga gtg gaa ggc atc tct gta cag gaa ggc ttc tct ttc gtg<br>His Phe Arg Val Glu Gly Ile Ser Val Gln Glu Gly Phe Ser Phe Val<br>670                   675                   680 | | 2308 |
| gag cca gtg ctg aca tca ata aaa cct gac ttt ggc ccg cgg gct ggg<br>Glu Pro Val Leu Thr Ser Ile Lys Pro Asp Phe Gly Pro Arg Ala Gly<br>685             690                  695                  700 | | 2356 |
| ggt act tat ctc acc ctc gaa ggc cag agc ctg tct att gcc acc agc<br>Gly Thr Tyr Leu Thr Leu Glu Gly Gln Ser Leu Ser Ile Ala Thr Ser<br>                   705                  710                  715 | | 2404 |
| cga gct gcg ctg gtc aat gga acc cag tgc cgg ctg gaa cag gtc aat<br>Arg Ala Ala Leu Val Asn Gly Thr Gln Cys Arg Leu Glu Gln Val Asn<br>720                     725                   730 | | 2452 |
| gag gag cag atc tta tgt gtc acg cct cct gga gct ggc acg gcc agg<br>Glu Glu Gln Ile Leu Cys Val Thr Pro Pro Gly Ala Gly Thr Ala Arg<br>735                     740                   745 | | 2500 |
| gtc ccc ctt cat ctg cag ata ggg ggt gct gag gtg cct ggc tcc tgg<br>Val Pro Leu His Leu Gln Ile Gly Gly Ala Glu Val Pro Gly Ser Trp<br>750                     755                   760 | | 2548 |
| acc ttt cac tac aag gaa gac cct att gtg ttg gac atc agt ccc aag<br>Thr Phe His Tyr Lys Glu Asp Pro Ile Val Leu Asp Ile Ser Pro Lys | | 2596 |

-continued

```
              765                 770                 775                 780
tgt ggc tac agt ggc tcc cac atc atg atc cat ggc cag cat ctg act          2644
Cys Gly Tyr Ser Gly Ser His Ile Met Ile His Gly Gln His Leu Thr
                    785                 790                 795 tca gca tgg cac ttc acg cta tca ttc cat gat gga caa agt aca gtg          2692
Ser Ala Trp His Phe Thr Leu Ser Phe His Asp Gly Gln Ser Thr Val
                    800                 805                 810 gag agc agg tgt gcg ggg cag ttt gtg gaa caa cag cag cgt cga tgt          2740
Glu Ser Arg Cys Ala Gly Gln Phe Val Glu Gln Gln Gln Arg Arg Cys
                    815                 820                 825 cgc ctg cct gaa tat gtg gtc cga aac cct cag ggg tgg gca aca ggg          2788
Arg Leu Pro Glu Tyr Val Val Arg Asn Pro Gln Gly Trp Ala Thr Gly
                    830                 835                 840 aat ctg agc gtc tgg ggt gat gga gca gct ggc ttc aca ctg cct ggt          2836
Asn Leu Ser Val Trp Gly Asp Gly Ala Ala Gly Phe Thr Leu Pro Gly
845                 850                 855                 860 ttt cgc ttc ctg ccc cca ccc agt cca ctc aga gct ggc ctg gtt gag          2884
Phe Arg Phe Leu Pro Pro Pro Ser Pro Leu Arg Ala Gly Leu Val Glu
                    865                 870                 875 ttg aaa cct gaa gaa cat tca gtt aaa gtt gag tat gtc ggg ctg ggc          2932
Leu Lys Pro Glu Glu His Ser Val Lys Val Glu Tyr Val Gly Leu Gly
                    880                 885                 890 gct gtg gca gac tgt gtg act gtg aac atg acc gtg ggt ggt gag gtc          2980
Ala Val Ala Asp Cys Val Thr Val Asn Met Thr Val Gly Gly Glu Val
                    895                 900                 905 tgc caa cat gag ctc cgg ggg gat gtg gtg atc tgc ccc ctg ccc cct          3028
Cys Gln His Glu Leu Arg Gly Asp Val Val Ile Cys Pro Leu Pro Pro
                    910                 915                 920 tcc ctg caa ctt ggc aag gat ggt gtc cca ttg cag gtc tgt gta gac          3076
Ser Leu Gln Leu Gly Lys Asp Gly Val Pro Leu Gln Val Cys Val Asp
925                 930                 935                 940 ggt ggg tgt cac atc ctg agc caa gtg gtt cgc tca agc cca ggc agg          3124
Gly Gly Cys His Ile Leu Ser Gln Val Val Arg Ser Ser Pro Gly Arg
                    945                 950                 955 gcc tca cag agg ata ctc ctt att gct ctt ctg gtc ttg atc ctg ctt          3172
Ala Ser Gln Arg Ile Leu Leu Ile Ala Leu Leu Val Leu Ile Leu Leu
                    960                 965                 970 gtg gct gtg ctg gcc gtt gcc ctg atc ttt aac tcc cga aga cgg aaa          3220
Val Ala Val Leu Ala Val Ala Leu Ile Phe Asn Ser Arg Arg Arg Lys
                    975                 980                 985 aag cag cta ggt gct cac tcc ctc tcc cca aca aca ctc tct gac atc          3268
Lys Gln Leu Gly Ala His Ser Leu Ser Pro Thr Thr Leu Ser Asp Ile
                    990                 995                 1000 aac gat aca gct tcc ggg gct ccg aac cat gaa gaa tcg tca gag           3313
Asn Asp Thr Ala Ser Gly Ala Pro Asn His Glu Glu Ser Ser Glu
1005                1010                1015 agt agg gat ggg aca agt gtc cca ctg ctg cgg aca gag tct atc           3358
Ser Arg Asp Gly Thr Ser Val Pro Leu Leu Arg Thr Glu Ser Ile
1020                1025                1030 cgg ctc cag gat ctg gac agg atg ctc cta gct gag gtc aag gat           3403
Arg Leu Gln Asp Leu Asp Arg Met Leu Leu Ala Glu Val Lys Asp
1035                1040                1045 gta ctg att ccc cat gaa caa gtg gtc atc cat act gac caa gtc           3448
Val Leu Ile Pro His Glu Gln Val Val Ile His Thr Asp Gln Val
1050                1055                1060 att ggc aaa ggc cac ttt ggt gtt gtc tac cac gga gaa tat aca           3493
Ile Gly Lys Gly His Phe Gly Val Val Tyr His Gly Glu Tyr Thr
1065                1070                1075 gac gga gca cag aat cag acc cac tgt gcc atc aag tct ctg agt           3538
```

| | | | | | | | | | | | | |
|---|---|---|---|---|---|---|---|---|---|---|---|---|
|Asp|Gly|Ala|Gln|Asn|Gln|Thr|His|Cys|Ala|Ile|Lys|Ser|Leu|Ser|
|1080| | | |1085| | | | |1090| | | | | |

```
cgc att aca gag gtg cag gag gtg gag gct ttc ctg cgg gag ggg       3583
Arg Ile Thr Glu Val Gln Glu Val Glu Ala Phe Leu Arg Glu Gly
1095            1100                1105 ctg ctc atg cgt ggc cta cat cac cca aac atc ctg gct ctc atc       3628
Leu Leu Met Arg Gly Leu His His Pro Asn Ile Leu Ala Leu Ile
1110            1115                1120 ggt atc atg ctg ccc ccg gag ggg ctt ccc cgg gtg ctg ttg ccc       3673
Gly Ile Met Leu Pro Pro Glu Gly Leu Pro Arg Val Leu Leu Pro
1125            1130                1135 tat atg cgc cac gga gac ctg ctt cgt ttc att cgc tcc cct cag       3718
Tyr Met Arg His Gly Asp Leu Leu Arg Phe Ile Arg Ser Pro Gln
1140            1145                1150 agg aac ccc act gtg aag gat ctt gtc agc ttt ggc ctg cag gta       3763
Arg Asn Pro Thr Val Lys Asp Leu Val Ser Phe Gly Leu Gln Val
1155            1160                1165 gcc tgt ggt atg gag tac ctg gca gag cag aag ttc gtg cac aga       3808
Ala Cys Gly Met Glu Tyr Leu Ala Glu Gln Lys Phe Val His Arg
1170            1175                1180 gac ctg gct gct agg aac tgc atg ctg gac gag tca ttc aca gtc       3853
Asp Leu Ala Ala Arg Asn Cys Met Leu Asp Glu Ser Phe Thr Val
1185            1190                1195 aag gtg gct gac ttt ggt ctg gca cgg ggc gtc cta gac aag gaa       3898
Lys Val Ala Asp Phe Gly Leu Ala Arg Gly Val Leu Asp Lys Glu
1200            1205                1210 tac tac agt gtt cgc cag cat cgc cat gct cgc ctg cca gtc aaa       3943
Tyr Tyr Ser Val Arg Gln His Arg His Ala Arg Leu Pro Val Lys
1215            1220                1225 tgg atg gca ctg gag agc ctg cag acc tac agg ttc acc acc aag       3988
Trp Met Ala Leu Glu Ser Leu Gln Thr Tyr Arg Phe Thr Thr Lys
1230            1235                1240 tcc gat gtg tgg tca ttc ggg gtg ctg ctc tgg gag cta cta aca       4033
Ser Asp Val Trp Ser Phe Gly Val Leu Leu Trp Glu Leu Leu Thr
1245            1250                1255 cgg ggt gct cca ccc tac ccc cat atc gat ccc ttc gac ctc tct       4078
Arg Gly Ala Pro Pro Tyr Pro His Ile Asp Pro Phe Asp Leu Ser
1260            1265                1270 cac ttc ctg gct cag ggc cgc cgc ctg cct cag cct gag tac tgt       4123
His Phe Leu Ala Gln Gly Arg Arg Leu Pro Gln Pro Glu Tyr Cys
1275            1280                1285 cct gat tca ctg tat cac gtg atg ctt cga tgc tgg gag gct gac       4168
Pro Asp Ser Leu Tyr His Val Met Leu Arg Cys Trp Glu Ala Asp
1290            1295                1300 cca gcg gca cga ccc acc ttc aga gcc cta gtg ctg gaa gta aag       4213
Pro Ala Ala Arg Pro Thr Phe Arg Ala Leu Val Leu Glu Val Lys
1305            1310                1315 cag gta gtg gcc tca ctg ctt ggg gac cac tat gtg cag ctg aca       4258
Gln Val Val Ala Ser Leu Leu Gly Asp His Tyr Val Gln Leu Thr
1320            1325                1330 gca gct tat gtg aac gta ggc ccc aga gcg gtg gat gat ggg agt       4303
Ala Ala Tyr Val Asn Val Gly Pro Arg Ala Val Asp Asp Gly Ser
1335            1340                1345 gtg cct ccg gag cag gta cag ccc tcg cct cag cat tgc agg agc       4348
Val Pro Pro Glu Gln Val Gln Pro Ser Pro Gln His Cys Arg Ser
1350            1355                1360 acg tca aag ccc cgg cct ctc tca gag cca ccc ctg ccc act tga       4393
Thr Ser Lys Pro Arg Pro Leu Ser Glu Pro Pro Leu Pro Thr
1365            1370                1375
```

```
ccaaagccct gagtaggcca caggcactag atctgctaag tggccttgag caaattacaa    4453
gctgcctctg ggcctaggac aagcctcagc atggaaaacc tccactcttt agctttctgg    4513
ggccactgaa ggtgggaaac cgggcccatt tgagcccctc gttccagcat gagccagtga    4573 cattttgta gcatgtattt atgtaatgtc tgttttgtac ctgtttcgga atacagagga     4633
tccagcagtg atcacagaga tactacagta taaataata taaataata aatgaatgaa     4693 tattcgagca caaaaaaaaa aaaaaaa                                        4720
```

<210> SEQ ID NO 47
<211> LENGTH: 1378
<212> TYPE: PRT
<213> ORGANISM: Mus musculus

<400> SEQUENCE: 47

```
Met Gly Leu Pro Leu Pro Leu Leu Gln Ser Ser Leu Leu Leu Met Leu
1               5                   10                  15

Leu Leu Arg Leu Ser Ala Ala Ser Thr Asn Leu Asn Trp Gln Cys Pro
            20                  25                  30

Arg Ile Pro Tyr Ala Ala Ser Arg Asp Phe Ser Val Lys Tyr Val Val
        35                  40                  45

Pro Ser Phe Ser Ala Gly Gly Arg Val Gln Ala Thr Ala Ala Tyr Glu
    50                  55                  60

Asp Ser Thr Asn Ser Ala Val Phe Val Ala Thr Arg Asn His Leu His
65                  70                  75                  80

Val Leu Gly Pro Asp Leu Gln Phe Ile Glu Asn Leu Thr Thr Gly Pro
                85                  90                  95

Ile Gly Asn Pro Gly Cys Gln Thr Cys Ala Ser Cys Gly Pro Gly Pro
            100                 105                 110

His Gly Pro Pro Lys Asp Thr Asp Thr Leu Val Leu Val Met Glu Pro
        115                 120                 125

Gly Leu Pro Ala Leu Val Ser Cys Gly Ser Thr Leu Gln Gly Arg Cys
    130                 135                 140

Phe Leu His Glu Leu Glu Pro Arg Gly Lys Ala Leu His Leu Ala Ala
145                 150                 155                 160

Pro Ala Cys Leu Phe Ser Ala Asn Asn Asn Lys Pro Glu Ala Cys Thr
                165                 170                 175

Asp Cys Val Ala Ser Pro Leu Gly Thr Arg Val Thr Val Val Glu Gln
            180                 185                 190

Gly His Ala Ser Tyr Phe Tyr Val Ala Ser Ser Leu Asp Pro Glu Leu
        195                 200                 205

Ala Ala Ser Phe Ser Pro Arg Ser Val Ser Ile Arg Arg Leu Lys Ser
    210                 215                 220

Asp Thr Ser Gly Phe Gln Pro Gly Phe Pro Ser Leu Ser Val Leu Pro
225                 230                 235                 240

Lys Tyr Leu Ala Ser Tyr Leu Ile Lys Tyr Val Tyr Ser Phe His Ser
                245                 250                 255

Gly Asp Phe Val Tyr Phe Leu Thr Val Gln Pro Ile Ser Val Thr Ser
            260                 265                 270

Pro Pro Ser Ala Leu His Thr Arg Leu Val Arg Leu Asn Ala Val Glu
        275                 280                 285

Pro Glu Ile Gly Asp Tyr Arg Glu Leu Val Leu Asp Cys His Phe Ala
    290                 295                 300

Pro Lys Arg Arg Arg Gly Ala Pro Glu Gly Thr Gln Pro Tyr Pro
305                 310                 315                 320
```

```
Val Leu Gln Ala Ala His Ser Ala Pro Val Asp Ala Lys Leu Ala Val
                325                 330                 335

Glu Leu Ser Ile Ser Glu Gly Gln Glu Val Leu Phe Gly Val Phe Val
                340                 345                 350

Thr Val Lys Asp Gly Gly Ser Gly Met Gly Pro Asn Ser Val Val Cys
            355                 360                 365

Ala Phe Pro Ile Tyr His Leu Asn Ile Leu Ile Glu Glu Gly Val Glu
        370                 375                 380

Tyr Cys Cys His Ser Ser Asn Ser Ser Ser Leu Leu Ser Arg Gly Leu
385                 390                 395                 400

Asp Phe Phe Gln Thr Pro Ser Phe Cys Pro Asn Pro Pro Gly Gly Glu
                405                 410                 415

Ala Ser Gly Pro Ser Ser Arg Cys His Tyr Phe Pro Leu Met Val His
            420                 425                 430

Ala Ser Phe Thr Arg Val Asp Leu Phe Asn Gly Leu Leu Gly Ser Val
        435                 440                 445

Lys Val Thr Ala Leu His Val Thr Arg Leu Gly Asn Val Thr Val Ala
450                 455                 460

His Met Gly Thr Val Asp Gly Arg Val Leu Gln Val Glu Ile Ala Arg
465                 470                 475                 480

Ser Leu Asn Tyr Leu Leu Tyr Val Ser Asn Phe Ser Leu Gly Ser Ser
                485                 490                 495

Gly Gln Pro Val His Arg Asp Val Ser Arg Leu Gly Asn Asp Leu Leu
            500                 505                 510

Phe Ala Ser Gly Asp Gln Val Phe Lys Val Pro Ile Gln Gly Pro Gly
        515                 520                 525

Cys Arg His Phe Leu Thr Cys Trp Arg Cys Leu Arg Ala Gln Arg Phe
        530                 535                 540

Met Gly Cys Gly Trp Cys Gly Asp Arg Cys Asp Arg Gln Lys Glu Cys
545                 550                 555                 560

Pro Gly Ser Trp Gln Gln Asp His Cys Pro Pro Glu Ile Ser Glu Phe
                565                 570                 575

Tyr Pro His Ser Gly Pro Leu Arg Gly Thr Thr Arg Leu Thr Leu Cys
            580                 585                 590

Gly Ser Asn Phe Tyr Leu Arg Pro Asp Asp Val Val Pro Glu Gly Thr
        595                 600                 605

His Gln Ile Thr Val Gly Gln Ser Pro Cys Arg Leu Leu Pro Lys Asp
        610                 615                 620

Ser Ser Pro Arg Pro Gly Ser Leu Lys Glu Phe Ile Gln Glu Leu
625                 630                 635                 640

Glu Cys Glu Leu Glu Pro Leu Val Thr Gln Ala Val Gly Thr Thr Asn
                645                 650                 655

Ile Ser Leu Val Ile Thr Asn Met Pro Ala Gly Lys His Phe Arg Val
            660                 665                 670

Glu Gly Ile Ser Val Gln Glu Gly Phe Ser Phe Val Glu Pro Val Leu
        675                 680                 685

Thr Ser Ile Lys Pro Asp Phe Gly Pro Arg Ala Gly Gly Thr Tyr Leu
        690                 695                 700

Thr Leu Glu Gly Gln Ser Leu Ser Ile Ala Thr Ser Arg Ala Ala Leu
705                 710                 715                 720

Val Asn Gly Thr Gln Cys Arg Leu Glu Gln Val Asn Glu Glu Gln Ile
                725                 730                 735
```

```
Leu Cys Val Thr Pro Pro Gly Ala Gly Thr Ala Arg Val Pro Leu His
            740                 745                 750

Leu Gln Ile Gly Gly Ala Glu Val Pro Gly Ser Trp Thr Phe His Tyr
        755                 760                 765

Lys Glu Asp Pro Ile Val Leu Asp Ile Ser Pro Lys Cys Gly Tyr Ser
770                 775                 780

Gly Ser His Ile Met Ile His Gly Gln His Leu Thr Ser Ala Trp His
785                 790                 795                 800

Phe Thr Leu Ser Phe His Asp Gly Gln Ser Thr Val Glu Ser Arg Cys
                805                 810                 815

Ala Gly Gln Phe Val Glu Gln Gln Arg Arg Cys Arg Leu Pro Glu
                820                 825                 830

Tyr Val Val Arg Asn Pro Gln Gly Trp Ala Thr Gly Asn Leu Ser Val
                835                 840                 845

Trp Gly Asp Gly Ala Ala Gly Phe Thr Leu Pro Gly Phe Arg Phe Leu
        850                 855                 860

Pro Pro Pro Ser Pro Leu Arg Ala Gly Leu Val Glu Leu Lys Pro Glu
865                 870                 875                 880

Glu His Ser Val Lys Val Glu Tyr Val Gly Leu Gly Ala Val Ala Asp
                885                 890                 895

Cys Val Thr Val Asn Met Thr Val Gly Gly Glu Val Cys Gln His Glu
                900                 905                 910

Leu Arg Gly Asp Val Val Ile Cys Pro Leu Pro Pro Ser Leu Gln Leu
            915                 920                 925

Gly Lys Asp Gly Val Pro Leu Gln Val Cys Val Asp Gly Gly Cys His
    930                 935                 940

Ile Leu Ser Gln Val Val Arg Ser Ser Pro Gly Arg Ala Ser Gln Arg
945                 950                 955                 960

Ile Leu Leu Ile Ala Leu Leu Val Leu Leu Val Ala Val Leu
                965                 970                 975

Ala Val Ala Leu Ile Phe Asn Ser Arg Arg Arg Lys Lys Gln Leu Gly
            980                 985                 990

Ala His Ser Leu Ser Pro Thr Thr  Leu Ser Asp Ile Asn Asp Thr Ala
        995                 1000                 1005

Ser Gly Ala Pro Asn His Glu  Glu Ser Ser Glu  Arg Asp Gly
    1010                 1015                 1020

Thr Ser Val Pro Leu Leu Arg  Thr Glu Ser Ile Arg  Leu Gln Asp
    1025                 1030                 1035

Leu Asp Arg Met Leu Leu Ala  Glu Val Lys Asp Val  Leu Ile Pro
    1040                 1045                 1050

His Glu Gln Val Val Ile His  Thr Asp Gln Val Ile  Gly Lys Gly
    1055                 1060                 1065

His Phe Gly Val Val Tyr His  Gly Glu Tyr Thr Asp  Gly Ala Gln
    1070                 1075                 1080

Asn Gln Thr His Cys Ala Ile  Lys Ser Leu Ser Arg  Ile Thr Glu
    1085                 1090                 1095

Val Gln Glu Val Glu Ala Phe  Leu Arg Glu Gly Leu  Leu Met Arg
    1100                 1105                 1110

Gly Leu His His Pro Asn Ile  Leu Ala Leu Ile Gly  Ile Met Leu
    1115                 1120                 1125

Pro Pro Glu Gly Leu Pro Arg  Val Leu Leu Pro Tyr  Met Arg His
    1130                 1135                 1140

Gly Asp  Leu Leu Arg Phe Ile  Arg Ser Pro Gln Arg  Asn Pro Thr
```

```
                1145                1150                1155

Val Lys Asp Leu Val Ser Phe Gly Leu Gln Val Ala Cys Gly Met
    1160                1165                1170

Glu Tyr Leu Ala Glu Gln Lys Phe Val His Arg Asp Leu Ala Ala
    1175                1180                1185

Arg Asn Cys Met Leu Asp Glu Ser Phe Thr Val Lys Val Ala Asp
    1190                1195                1200

Phe Gly Leu Ala Arg Gly Val Leu Asp Lys Glu Tyr Tyr Ser Val
    1205                1210                1215

Arg Gln His Arg His Ala Arg Leu Pro Val Lys Trp Met Ala Leu
    1220                1225                1230

Glu Ser Leu Gln Thr Tyr Arg Phe Thr Thr Lys Ser Asp Val Trp
    1235                1240                1245

Ser Phe Gly Val Leu Leu Trp Glu Leu Leu Thr Arg Gly Ala Pro
    1250                1255                1260

Pro Tyr Pro His Ile Asp Pro Phe Asp Leu Ser His Phe Leu Ala
    1265                1270                1275

Gln Gly Arg Arg Leu Pro Gln Pro Glu Tyr Cys Pro Asp Ser Leu
    1280                1285                1290

Tyr His Val Met Leu Arg Cys Trp Glu Ala Asp Pro Ala Ala Arg
    1295                1300                1305

Pro Thr Phe Arg Ala Leu Val Leu Glu Val Lys Gln Val Val Ala
    1310                1315                1320

Ser Leu Leu Gly Asp His Tyr Val Gln Leu Thr Ala Ala Tyr Val
    1325                1330                1335

Asn Val Gly Pro Arg Ala Val Asp Asp Gly Ser Val Pro Pro Glu
    1340                1345                1350

Gln Val Gln Pro Ser Pro Gln His Cys Arg Ser Thr Ser Lys Pro
    1355                1360                1365

Arg Pro Leu Ser Glu Pro Pro Leu Pro Thr
    1370                1375

<210> SEQ ID NO 48
<211> LENGTH: 1413
<212> TYPE: DNA
<213> ORGANISM: Artificial Sequence
<220> FEATURE:
<223> OTHER INFORMATION: MOR07919 heavy chain
<220> FEATURE:
<221> NAME/KEY: CDS
<222> LOCATION: (1)..(1413)

<400> SEQUENCE: 48 atg aaa cac ctg tgg ttc ttc ctc ctg ctg gtg gca gct ccc aga tgg     48
Met Lys His Leu Trp Phe Phe Leu Leu Leu Val Ala Ala Pro Arg Trp
1               5                   10                  15 gtc ctg tcc cag gtg caa ttg gtt cag agc ggc gcg gaa gtg aaa aaa    96
Val Leu Ser Gln Val Gln Leu Val Gln Ser Gly Ala Glu Val Lys Lys
            20                  25                  30 ccg ggc gaa agc ctg aaa att agc tgc aaa ggt tcc gga tat tcc ttt   144
Pro Gly Glu Ser Leu Lys Ile Ser Cys Lys Gly Ser Gly Tyr Ser Phe
        35                  40                  45 act aat tat tgg att tct tgg gtg cgc cag atg cct ggg aag ggt ctc   192
Thr Asn Tyr Trp Ile Ser Trp Val Arg Gln Met Pro Gly Lys Gly Leu
    50                  55                  60 gag tgg atg ggc ttt atc tat ccg gat gat agc tat acc cgt tat tct   240
Glu Trp Met Gly Phe Ile Tyr Pro Asp Asp Ser Tyr Thr Arg Tyr Ser
65                  70                  75                  80
```

-continued

| | | |
|---|---|---|
| ccg agc ttt cag ggc cag gtg acc att agc gcg gat aaa agc att agc<br>Pro Ser Phe Gln Gly Gln Val Thr Ile Ser Ala Asp Lys Ser Ile Ser<br>85  90  95 | 288 |
| acc gcg tat ctt caa tgg agc agc ctg aaa gcg agc gat acg gcc atg<br>Thr Ala Tyr Leu Gln Trp Ser Ser Leu Lys Ala Ser Asp Thr Ala Met<br>100  105  110 | 336 |
| tat tat tgc gcg cgt ttt tct tat cgt cat tat ctt gat atg gat gat<br>Tyr Tyr Cys Ala Arg Phe Ser Tyr Arg His Tyr Leu Asp Met Asp Asp<br>115  120  125 | 384 |
| cat tgg ggc caa ggc acc ctg gtg acg gtt agc tca gcc tcc acc aag<br>His Trp Gly Gln Gly Thr Leu Val Thr Val Ser Ser Ala Ser Thr Lys<br>130  135  140 | 432 |
| ggt cca tcg gtc ttc ccc ctg gca ccc tcc tcc aag agc acc tct ggg<br>Gly Pro Ser Val Phe Pro Leu Ala Pro Ser Ser Lys Ser Thr Ser Gly<br>145  150  155  160 | 480 |
| ggc aca gcg gcc ctg ggc tgc ctg gtc aag gac tac ttc ccc gaa ccg<br>Gly Thr Ala Ala Leu Gly Cys Leu Val Lys Asp Tyr Phe Pro Glu Pro<br>165  170  175 | 528 |
| gtg acg gtg tcg tgg aac tca ggc gcc ctg acc agc ggc gtg cac acc<br>Val Thr Val Ser Trp Asn Ser Gly Ala Leu Thr Ser Gly Val His Thr<br>180  185  190 | 576 |
| ttc ccg gct gtc cta cag tcc tca gga ctc tac tcc ctc agc agc gtg<br>Phe Pro Ala Val Leu Gln Ser Ser Gly Leu Tyr Ser Leu Ser Ser Val<br>195  200  205 | 624 |
| gtg acc gtg ccc tcc agc agc ttg ggc acc cag acc tac atc tgc aac<br>Val Thr Val Pro Ser Ser Ser Leu Gly Thr Gln Thr Tyr Ile Cys Asn<br>210  215  220 | 672 |
| gtg aat cac aag ccc agc aac acc aag gtg gac aag aga gtt gag ccc<br>Val Asn His Lys Pro Ser Asn Thr Lys Val Asp Lys Arg Val Glu Pro<br>225  230  235  240 | 720 |
| aaa tct tgt gac aaa act cac aca tgc cca ccg tgc cca gca cct gaa<br>Lys Ser Cys Asp Lys Thr His Thr Cys Pro Pro Cys Pro Ala Pro Glu<br>245  250  255 | 768 |
| ctc ctg ggg gga ccg tca gtc ttc ctc ttc ccc cca aaa ccc aag gac<br>Leu Leu Gly Gly Pro Ser Val Phe Leu Phe Pro Pro Lys Pro Lys Asp<br>260  265  270 | 816 |
| acc ctc atg atc tcc cgg acc cct gag gtc aca tgc gtg gtg gtg gac<br>Thr Leu Met Ile Ser Arg Thr Pro Glu Val Thr Cys Val Val Val Asp<br>275  280  285 | 864 |
| gtg agc cac gaa gac cct gag gtc aag ttc aac tgg tac gtg gac ggc<br>Val Ser His Glu Asp Pro Glu Val Lys Phe Asn Trp Tyr Val Asp Gly<br>290  295  300 | 912 |
| gtg gag gtg cat aat gcc aag aca aag ccg cgg gag gag cag tac aac<br>Val Glu Val His Asn Ala Lys Thr Lys Pro Arg Glu Glu Gln Tyr Asn<br>305  310  315  320 | 960 |
| agc acg tac cgg gtg gtc agc gtc ctc acc gtc ctg cac cag gac tgg<br>Ser Thr Tyr Arg Val Val Ser Val Leu Thr Val Leu His Gln Asp Trp<br>325  330  335 | 1008 |
| ctg aat ggc aag gag tac aag tgc aag gtc tcc aac aaa gcc ctc cca<br>Leu Asn Gly Lys Glu Tyr Lys Cys Lys Val Ser Asn Lys Ala Leu Pro<br>340  345  350 | 1056 |
| gcc ccc atc gag aaa acc atc tcc aaa gcc aaa ggg cag ccc cga gaa<br>Ala Pro Ile Glu Lys Thr Ile Ser Lys Ala Lys Gly Gln Pro Arg Glu<br>355  360  365 | 1104 |
| cca cag gtg tac acc ctg ccc cca tcc cgg gag gag atg acc aag aac<br>Pro Gln Val Tyr Thr Leu Pro Pro Ser Arg Glu Glu Met Thr Lys Asn<br>370  375  380 | 1152 |
| cag gtc agc ctg acc tgc ctg gtc aaa ggc ttc tat ccc agc gac atc<br>Gln Val Ser Leu Thr Cys Leu Val Lys Gly Phe Tyr Pro Ser Asp Ile | 1200 |

```
                385                 390                 395                 400
gcc gtg gag tgg gag agc aat ggg cag ccg gag aac aac tac aag acc          1248
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tac agc aag          1296
Thr Pro Pro Val Leu Asp Ser Asp Gly Ser Phe Phe Leu Tyr Ser Lys
                420                 425                 430 ctc acc gtg gac aag agc agg tgg cag cag ggg aac gtc ttc tca tgc          1344
Leu Thr Val Asp Lys Ser Arg Trp Gln Gln Gly Asn Val Phe Ser Cys
                435                 440                 445 tcc gtg atg cat gag gct ctg cac aac cac tac acg cag aag agc ctc          1392
Ser Val Met His Glu Ala Leu His Asn His Tyr Thr Gln Lys Ser Leu
                450                 455                 460 tcc ctg tct ccg ggt aaa tga                                               1413
Ser Leu Ser Pro Gly Lys
465                 470

<210> SEQ ID NO 49
<211> LENGTH: 470
<212> TYPE: PRT
<213> ORGANISM: Artificial Sequence
<220> FEATURE:
<223> OTHER INFORMATION: Synthetic Construct

<400> SEQUENCE: 49

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Glu Ser Leu Lys Ile Ser Cys Lys Gly Ser Gly Tyr Ser Phe
            35                  40                  45

Thr Asn Tyr Trp Ile Ser Trp Val Arg Gln Met Pro Gly Lys Gly Leu
        50                  55                  60

Glu Trp Met Gly Phe Ile Tyr Pro Asp Asp Ser Tyr Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
                100                 105                 110

Tyr Tyr Cys Ala Arg Phe Ser Tyr Arg His Tyr Leu Asp Met Asp Asp
            115                 120                 125

His Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
        210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255
```

```
Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 50
<211> LENGTH: 1401
<212> TYPE: DNA
<213> ORGANISM: Artificial Sequence
<220> FEATURE:
<223> OTHER INFORMATION: MOR07692, MOR07923, MOR07924, MOR07925 and
      MOR07926 heavy chain
<220> FEATURE:
<221> NAME/KEY: CDS
<222> LOCATION: (1)..(1401)

<400> SEQUENCE: 50 atg aaa cac ctg tgg ttc ttc ctc ctg ctg gtg gca gct ccc aga tgg     48
Met Lys His Leu Trp Phe Phe Leu Leu Leu Val Ala Ala Pro Arg Trp
1               5                   10                  15 gtc ctg tcc cag gtg caa ttg gtg gaa agc ggc ggc ggc ctg gtg caa     96
Val Leu Ser Gln Val Gln Leu Val Glu Ser Gly Gly Gly Leu Val Gln
            20                  25                  30 ccg ggc ggc agc ctg cgt ctg agc tgc gcg gcc tcc gga ttt acc ttt    144
Pro Gly Gly Ser Leu Arg Leu Ser Cys Ala Ala Ser Gly Phe Thr Phe
        35                  40                  45 aat tct tat tct atg tct tgg gtg cgc caa gcc cct ggg aag ggt ctc    192
Asn Ser Tyr Ser Met Ser Trp Val Arg Gln Ala Pro Gly Lys Gly Leu
    50                  55                  60 gag tgg gtg agc tat atc tct tct cgt tct agc act acc tat tat gcg    240
Glu Trp Val Ser Tyr Ile Ser Ser Arg Ser Ser Thr Thr Tyr Tyr Ala
65                  70                  75                  80 gat agc gtg aaa ggc cgt ttt acc att tca cgt gat aat tcg aaa aac    288
Asp Ser Val Lys Gly Arg Phe Thr Ile Ser Arg Asp Asn Ser Lys Asn
```

-continued

|     |     |     | 85  |     |     |     | 90  |     |     |     | 95  |     |     |      |
|-----|-----|-----|-----|-----|-----|-----|-----|-----|-----|-----|-----|-----|-----|------|

```
acc ctg tat ctg caa atg aac agc ctg cgt gcg gaa gat acg gcc gtg         336
Thr Leu Tyr Leu Gln Met Asn Ser Leu Arg Ala Glu Asp Thr Ala Val
            100                 105                 110 tat tat tgc gcg cgt ggt tat ttt cat ggt atg gat tat tgg ggc caa         384
Tyr Tyr Cys Ala Arg Gly Tyr Phe His Gly Met Asp Tyr Trp Gly Gln
            115                 120                 125 ggc acc ctg gtg acg gtt agc tca gcc tcc acc aag ggt cca tcg gtc         432
Gly Thr Leu Val Thr Val Ser Ser Ala Ser Thr Lys Gly Pro Ser Val
        130                 135                 140 ttc ccc ctg gca ccc tcc tcc aag agc acc tct ggg ggc aca gcg gcc         480
Phe Pro Leu Ala Pro Ser Ser Lys Ser Thr Ser Gly Gly Thr Ala Ala
145                 150                 155                 160 ctg ggc tgc ctg gtc aag gac tac ttc ccc gaa ccg gtg acg gtg tcg         528
Leu Gly Cys Leu Val Lys Asp Tyr Phe Pro Glu Pro Val Thr Val Ser
                165                 170                 175 tgg aac tca ggc gcc ctg acc agc ggc gtg cac acc ttc ccg gct gtc         576
Trp Asn Ser Gly Ala Leu Thr Ser Gly Val His Thr Phe Pro Ala Val
            180                 185                 190 cta cag tcc tca gga ctc tac tcc ctc agc agc gtg gtg acc gtg ccc         624
Leu Gln Ser Ser Gly Leu Tyr Ser Leu Ser Ser Val Val Thr Val Pro
                195                 200                 205 tcc agc agc ttg ggc acc cag acc tac atc tgc aac gtg aat cac aag         672
Ser Ser Ser Leu Gly Thr Gln Thr Tyr Ile Cys Asn Val Asn His Lys
        210                 215                 220 ccc agc aac acc aag gtg gac aag aga gtt gag ccc aaa tct tgt gac         720
Pro Ser Asn Thr Lys Val Asp Lys Arg Val Glu Pro Lys Ser Cys Asp
225                 230                 235                 240 aaa act cac aca tgc cca ccg tgc cca gca cct gaa ctc ctg ggg gga         768
Lys Thr His Thr Cys Pro Pro Cys Pro Ala Pro Glu Leu Leu Gly Gly
                245                 250                 255 ccg tca gtc ttc ctc ttc ccc cca aaa ccc aag gac acc ctc atg atc         816
Pro Ser Val Phe Leu Phe Pro Pro Lys Pro Lys Asp Thr Leu Met Ile
            260                 265                 270 tcc cgg acc cct gag gtc aca tgc gtg gtg gtg gac gtg agc cac gaa         864
Ser Arg Thr Pro Glu Val Thr Cys Val Val Val Asp Val Ser His Glu
        275                 280                 285 gac cct gag gtc aag ttc aac tgg tac gtg gac ggc gtg gag gtg cat         912
Asp Pro Glu Val Lys Phe Asn Trp Tyr Val Asp Gly Val Glu Val His
    290                 295                 300 aat gcc aag aca aag ccg cgg gag gag cag tac aac agc acg tac cgg         960
Asn Ala Lys Thr Lys Pro Arg Glu Glu Gln Tyr Asn Ser Thr Tyr Arg
305                 310                 315                 320 gtg gtc agc gtc ctc acc gtc ctg cac cag gac tgg ctg aat ggc aag        1008
Val Val Ser Val Leu Thr Val Leu His Gln Asp Trp Leu Asn Gly Lys
                325                 330                 335 gag tac aag tgc aag gtc tcc aac aaa gcc ctc cca gcc ccc atc gag        1056
Glu Tyr Lys Cys Lys Val Ser Asn Lys Ala Leu Pro Ala Pro Ile Glu
            340                 345                 350 aaa acc atc tcc aaa gcc aaa ggg cag ccc cga gaa cca cag gtg tac        1104
Lys Thr Ile Ser Lys Ala Lys Gly Gln Pro Arg Glu Pro Gln Val Tyr
        355                 360                 365 acc ctg ccc cca tcc cgg gag gag atg acc aag aac cag gtc agc ctg        1152
Thr Leu Pro Pro Ser Arg Glu Glu Met Thr Lys Asn Gln Val Ser Leu
    370                 375                 380 acc tgc ctg gtc aaa ggc ttc tat ccc agc gac atc gcc gtg gag tgg        1200
Thr Cys Leu Val Lys Gly Phe Tyr Pro Ser Asp Ile Ala Val Glu Trp
385                 390                 395                 400 gag agc aat ggg cag ccg gag aac aac tac aag acc acg cct ccc gtg        1248
Glu Ser Asn Gly Gln Pro Glu Asn Asn Tyr Lys Thr Thr Pro Pro Val
```

```
Glu Ser Asn Gly Gln Pro Glu Asn Asn Tyr Lys Thr Thr Pro Pro Val
                405                 410                 415 ctg gac tcc gac ggc tcc ttc ttc ctc tac agc aag ctc acc gtg gac    1296
Leu Asp Ser Asp Gly Ser Phe Phe Leu Tyr Ser Lys Leu Thr Val Asp
        420                 425                 430 aag agc agg tgg cag cag ggg aac gtc ttc tca tgc tcc gtg atg cat    1344
Lys Ser Arg Trp Gln Gln Gly Asn Val Phe Ser Cys Ser Val Met His
            435                 440                 445 gag gct ctg cac aac cac tac acg cag aag agc ctc tcc ctg tct ccg    1392
Glu Ala Leu His Asn His Tyr Thr Gln Lys Ser Leu Ser Leu Ser Pro
        450                 455                 460 ggt aaa tga                                                          1401
Gly Lys
465

<210> SEQ ID NO 51
<211> LENGTH: 466
<212> TYPE: PRT
<213> ORGANISM: Artificial Sequence
<220> FEATURE:
<223> OTHER INFORMATION: Synthetic Construct

<400> SEQUENCE: 51

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Asn Ser Tyr Ser Met Ser Trp Val Arg Gln Ala Pro Gly Lys Gly Leu
    50                  55                  60

Glu Trp Val Ser Tyr Ile Ser Ser Arg Ser Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Tyr Phe His Gly Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270
```

```
Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 52
<211> LENGTH: 702
<212> TYPE: DNA
<213> ORGANISM: Artificial Sequence
<220> FEATURE:
<223> OTHER INFORMATION: MOR07919 light chain
<220> FEATURE:
<221> NAME/KEY: CDS
<222> LOCATION: (1)..(702)

<400> SEQUENCE: 52 atg gcc tgg gct ctg ctg ctc ctc acc ctc ctc act cag ggc aca gga      48
Met Ala Trp Ala Leu Leu Leu Leu Thr Leu Leu Thr Gln Gly Thr Gly
1               5                   10                  15 tcc tgg gct gat atc gaa ctg acc cag ccg cct tca gtg agc gtt gca      96
Ser Trp Ala Asp Ile Glu Leu Thr Gln Pro Pro Ser Val Ser Val Ala
            20                  25                  30 cca ggt cag acc gcg cgt atc tcg tgt agc ggc gat tct ctt ggt tct     144
Pro Gly Gln Thr Ala Arg Ile Ser Cys Ser Gly Asp Ser Leu Gly Ser
        35                  40                  45 aag tat gtt cat tgg tac cag cag aaa ccc ggg cag gcg cca gtt ctt     192
Lys Tyr Val His Trp Tyr Gln Gln Lys Pro Gly Gln Ala Pro Val Leu
    50                  55                  60 gtg att tat cgt gat aat aag cgt ccc tca ggc atc ccg gaa cgc ttt     240
Val Ile Tyr Arg Asp Asn Lys Arg Pro Ser Gly Ile Pro Glu Arg Phe
65                  70                  75                  80 agc gga tcc aac agc ggc aac acc gcg acc ctg acc att agc ggc act     288
Ser Gly Ser Asn Ser Gly Asn Thr Ala Thr Leu Thr Ile Ser Gly Thr
                85                  90                  95 cag gcg gaa gac gaa gcg gat tat tat tgc cag tct tat gat gct act     336
Gln Ala Glu Asp Glu Ala Asp Tyr Tyr Cys Gln Ser Tyr Asp Ala Thr
```

| | | | | | | | | | | | | | | |
|---|---|---|---|---|---|---|---|---|---|---|---|---|---|---|
| | | 100 | | | | 105 | | | | 110 | | | | |
| gag | ttt | act | tat | gtg | ttt | ggc | ggc | acg | aag | tta | acc | gtc | cta | ggt | 384 |
| Glu | Phe | Thr | Tyr | Val | Phe | Gly | Gly | Thr | Lys | Leu | Thr | Val | Leu | Gly | |
| | | 115 | | | | 120 | | | | 125 | | | | | |
| cag | ccc | aag | gct | gcc | ccc | tcg | gtc | act | ctg | ttc | ccg | ccc | tcc | tct | gag | 432 |
| Gln | Pro | Lys | Ala | Ala | Pro | Ser | Val | Thr | Leu | Phe | Pro | Pro | Ser | Ser | Glu |
| | 130 | | | | 135 | | | | | 140 | | | | | |
| gag | ctt | caa | gcc | aac | aag | gcc | aca | ctg | gtg | tgt | ctc | ata | agt | gac | ttc | 480 |
| Glu | Leu | Gln | Ala | Asn | Lys | Ala | Thr | Leu | Val | Cys | Leu | Ile | Ser | Asp | Phe |
| 145 | | | | | 150 | | | | | 155 | | | | | 160 |
| tac | ccg | gga | gcc | gtg | aca | gtg | gcc | tgg | aag | gca | gat | agc | agc | ccc | gtc | 528 |
| Tyr | Pro | Gly | Ala | Val | Thr | Val | Ala | Trp | Lys | Ala | Asp | Ser | Ser | Pro | Val |
| | | | | 165 | | | | | 170 | | | | | 175 | |
| aag | gcg | gga | gtg | gag | acc | acc | aca | ccc | tcc | aaa | caa | agc | aac | aac | aag | 576 |
| Lys | Ala | Gly | Val | Glu | Thr | Thr | Thr | Pro | Ser | Lys | Gln | Ser | Asn | Asn | Lys |
| | | | | 180 | | | | | 185 | | | | | 190 | |
| tac | gcg | gcc | agc | agc | tat | ctg | agc | ctg | acg | cct | gag | cag | tgg | aag | tcc | 624 |
| Tyr | Ala | Ala | Ser | Ser | Tyr | Leu | Ser | Leu | Thr | Pro | Glu | Gln | Trp | Lys | Ser |
| | | 195 | | | | 200 | | | | 205 | | | | | |
| cac | aga | agc | tac | agc | tgc | cag | gtc | acg | cat | gaa | ggg | agc | acc | gtg | gag | 672 |
| His | Arg | Ser | Tyr | Ser | Cys | Gln | Val | Thr | His | Glu | Gly | Ser | Thr | Val | Glu |
| | 210 | | | | 215 | | | | | 220 | | | | | |
| aag | aca | gtg | gcc | cct | aca | gaa | tgt | tca | tag | | | | | | 702 |
| Lys | Thr | Val | Ala | Pro | Thr | Glu | Cys | Ser | | | | | | | |
| 225 | | | | 230 | | | | | | | | | | | |

<210> SEQ ID NO 53
<211> LENGTH: 233
<212> TYPE: PRT
<213> ORGANISM: Artificial Sequence
<220> FEATURE:
<223> OTHER INFORMATION: Synthetic Construct

<400> SEQUENCE: 53

Met Ala Trp Ala Leu Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
            20                  25                  30

Pro Gly Gln Thr Ala Arg Ile Ser Cys Ser Gly Asp Ser Leu Gly Ser
        35                  40                  45

Lys Tyr Val His Trp Tyr Gln Gln Lys Pro Gly Gln Ala Pro Val Leu
    50                  55                  60

Val Ile Tyr Arg Asp Asn Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Gln Ser Tyr Asp Ala Thr
            100                 105                 110

Glu Phe Thr Tyr Val Phe Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

```
Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
        210                 215                 220

Lys Thr Val Ala Pro Thr Glu Cys Ser
225                 230

<210> SEQ ID NO 54
<211> LENGTH: 708
<212> TYPE: DNA
<213> ORGANISM: Artificial Sequence
<220> FEATURE:
<223> OTHER INFORMATION: MOR07692 light chain
<220> FEATURE:
<221> NAME/KEY: CDS
<222> LOCATION: (1)..(708)

<400> SEQUENCE: 54
```

| | | | | | | | | | | | | | | | | |
|---|---|---|---|---|---|---|---|---|---|---|---|---|---|---|---|---|
| atg | gtg | ttg | cag | acc | cag | gtc | ttc | att | tct | ctg | ttg | ctc | tgg | atc | tct | 48 |
| Met | Val | Leu | Gln | Thr | Gln | Val | Phe | Ile | Ser | Leu | Leu | Leu | Trp | Ile | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggt | gcc | tac | ggg | gat | atc | gtg | ctg | acc | cag | agc | ccg | gcg | acc | ctg | agc | 96 |
| Gly | Ala | Tyr | Gly | Asp | Ile | Val | Leu | Thr | Gln | Ser | Pro | Ala | Thr | Leu | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| ctg | tct | ccg | ggc | gaa | cgt | gcg | acc | ctg | agc | tgc | aga | gcg | agc | cag | tct | 144 |
| Leu | Ser | Pro | Gly | Glu | Arg | Ala | Thr | Leu | Ser | Cys | Arg | Ala | Ser | Gln | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| gtt | tct | ttt | gat | tat | ctg | ggt | tgg | tac | cag | cag | aaa | cca | ggt | caa | gca | 192 |
| Val | Ser | Phe | Asp | Tyr | Leu | Gly | Trp | Tyr | Gln | Gln | Lys | Pro | Gly | Gln | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| ccg | cgt | cta | tta | att | tat | ggt | gct | tct | aat | cgt | gca | act | ggg | gtc | ccg | 240 |
| Pro | Arg | Leu | Leu | Ile | Tyr | Gly | Ala | Ser | Asn | Arg | Ala | Thr | Gly | Val | Pro | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gcg | cgt | ttt | agc | ggc | tct | gga | tcc | ggc | acg | gat | ttt | acc | ctg | acc | att | 288 |
| Ala | Arg | Phe | Ser | Gly | Ser | Gly | Ser | Gly | Thr | Asp | Phe | Thr | Leu | Thr | Ile | |
| | | | 85 | | | | | 90 | | | | | 95 | | | |

| | | | | | | | | | | | | | | | | |
|---|---|---|---|---|---|---|---|---|---|---|---|---|---|---|---|---|
| agc | agc | ctg | gaa | cct | gaa | gac | ttt | gcg | act | tat | tat | tgc | cag | cag | tat | 336 |
| Ser | Ser | Leu | Glu | Pro | Glu | Asp | Phe | Ala | Thr | Tyr | Tyr | Cys | Gln | Gln | Tyr | |
| | | | 100 | | | | | 105 | | | | | 110 | | | |

| | | | | | | | | | | | | | | | | |
|---|---|---|---|---|---|---|---|---|---|---|---|---|---|---|---|---|
| tat | aat | atg | cct | tat | acc | ttt | ggc | cag | ggt | acg | aaa | gtt | gaa | att | aaa | 384 |
| Tyr | Asn | Met | Pro | Tyr | Thr | Phe | Gly | Gln | Gly | Thr | Lys | Val | Glu | Ile | Lys | |
| | | 115 | | | | | 120 | | | | | 125 | | | | |

| | | | | | | | | | | | | | | | | |
|---|---|---|---|---|---|---|---|---|---|---|---|---|---|---|---|---|
| cgt | acg | gtg | gct | gca | cca | tct | gtc | ttc | atc | ttc | ccg | cca | tct | gat | gag | 432 |
| Arg | Thr | Val | Ala | Ala | Pro | Ser | Val | Phe | Ile | Phe | Pro | Pro | Ser | Asp | Glu | |
| | 130 | | | | | 135 | | | | | 140 | | | | | |

| | | | | | | | | | | | | | | | | |
|---|---|---|---|---|---|---|---|---|---|---|---|---|---|---|---|---|
| cag | ttg | aaa | tct | gga | act | gcc | tct | gtt | gtg | tgc | ctg | ctg | aat | aac | ttc | 480 |
| Gln | Leu | Lys | Ser | Gly | Thr | Ala | Ser | Val | Val | Cys | Leu | Leu | Asn | Asn | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tat | ccc | aga | gag | gcc | aaa | gta | cag | tgg | aag | gtg | gat | aac | gcc | ctc | caa | 528 |
| Tyr | Pro | Arg | Glu | Ala | Lys | Val | Gln | Trp | Lys | Val | Asp | Asn | Ala | Leu | Gln | |
| | | | | 165 | | | | | 170 | | | | | 175 | | |

| | | | | | | | | | | | | | | | | |
|---|---|---|---|---|---|---|---|---|---|---|---|---|---|---|---|---|
| tcg | ggt | aac | tcc | cag | gag | agt | gtc | aca | gag | cag | gac | agc | aag | gac | agc | 576 |
| Ser | Gly | Asn | Ser | Gln | Glu | Ser | Val | Thr | Glu | Gln | Asp | Ser | Lys | Asp | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| acc | tac | agc | ctc | agc | agc | acc | ctg | acg | ctg | agc | aaa | gca | gac | tac | gag | 624 |
| Thr | Tyr | Ser | Leu | Ser | Ser | Thr | Leu | Thr | Leu | Ser | Lys | Ala | Asp | Tyr | Glu | |
| | | | 195 | | | | | 200 | | | | | 205 | | | |

| | | | | | | | | | | | | | | | | |
|---|---|---|---|---|---|---|---|---|---|---|---|---|---|---|---|---|
| aaa | cac | aaa | gtc | tac | gcc | tgc | gaa | gtc | acc | cat | cag | ggc | ctg | agc | tcg | 672 |
| Lys | His | Lys | Val | Tyr | Ala | Cys | Glu | Val | Thr | His | Gln | Gly | Leu | Ser | Ser | |
| | 210 | | | | | 215 | | | | | 220 | | | | | |

```
ccc gtc aca aag agc ttc aac agg gga gag tgt tag                          708
Pro Val Thr Lys Ser Phe Asn Arg Gly Glu Cys
225                 230                 235

<210> SEQ ID NO 55
<211> LENGTH: 235
<212> TYPE: PRT
<213> ORGANISM: Artificial Sequence
<220> FEATURE:
<223> OTHER INFORMATION: Synthetic Construct

<400> SEQUENCE: 55

Met Val Leu Gln Thr Gln Val Phe Ile Ser Leu Leu Trp Ile Ser
1               5                   10                  15

Gly Ala Tyr Gly Asp Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Phe Asp Tyr Leu Gly Trp Tyr Gln Gln Lys Pro Gly Gln Ala
        50                  55                  60

Pro Arg Leu Leu Ile Tyr Gly Ala Ser Asn Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Thr Tyr Tyr Cys Gln Gln Tyr
            100                 105                 110

Tyr Asn Met Pro Tyr Thr Phe Gly Gln Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 56
<211> LENGTH: 708
<212> TYPE: DNA
<213> ORGANISM: Artificial Sequence
<220> FEATURE:
<223> OTHER INFORMATION: MOR07923 light chain
<220> FEATURE:
<221> NAME/KEY: CDS
<222> LOCATION: (1)..(708)

<400> SEQUENCE: 56 atg gtg ttg cag acc cag gtc ttc att tct ctg ttg ctc tgg atc tct    48
Met Val Leu Gln Thr Gln Val Phe Ile Ser Leu Leu Leu Trp Ile Ser
1               5                   10                  15 ggt gcc tac ggg gat atc gtg ctg acc cag agc ccg gcg acc ctg agc    96
Gly Ala Tyr Gly Asp Ile Val Leu Thr Gln Ser Pro Ala Thr Leu Ser
                20                  25                  30
```

```
ctg tct ccg ggc gaa cgt gcg acc ctg agc tgc aga gcg agc cag tct      144
Leu Ser Pro Gly Glu Arg Ala Thr Leu Ser Cys Arg Ala Ser Gln Ser
            35                  40                  45 gtt tct ttt gat tat ctg ggt tgg tac cag cag aaa cca ggt caa gca      192
Val Ser Phe Asp Tyr Leu Gly Trp Tyr Gln Gln Lys Pro Gly Gln Ala
    50                  55                  60 ccg cgt cta tta att tat ggt gct tct aat cgt gca act ggg gtc ccg      240
Pro Arg Leu Leu Ile Tyr Gly Ala Ser Asn Arg Ala Thr Gly Val Pro
65                  70                  75                  80 gcg cgt ttt agc ggc tct gga tcc ggc acg gat ttt acc ctg acc att      288
Ala Arg Phe Ser Gly Ser Gly Ser Gly Thr Asp Phe Thr Leu Thr Ile
                85                  90                  95 agc agc ctg gaa cct gaa gac ttt gcg acc tat tat tgc ttt cag tat      336
Ser Ser Leu Glu Pro Glu Asp Phe Ala Thr Tyr Tyr Cys Phe Gln Tyr
            100                 105                 110 ctt att gtt cct ttt acc ttt ggc cag ggt acg aaa gtt gaa att aaa      384
Leu Ile Val Pro Phe Thr Phe Gly Gln Gly Thr Lys Val Glu Ile Lys
        115                 120                 125 cgt acg gtg gct gca cca tct gtc ttc atc ttc ccg cca tct gat gag      432
Arg Thr Val Ala Ala Pro Ser Val Phe Ile Phe Pro Pro Ser Asp Glu
130                 135                 140 cag ttg aaa tct gga act gcc tct gtt gtg tgc ctg ctg aat aac ttc      480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa      528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc      576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag      624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg      672
Lys His Lys Val Tyr Ala Cys Glu Val Thr His Gln Gly Leu Ser Ser
    210                 215                 220 ccc gtc aca aag agc ttc aac agg gga gag tgt tag                      708
Pro Val Thr Lys Ser Phe Asn Arg Gly Glu Cys
225                 230                 235

<210> SEQ ID NO 57
<211> LENGTH: 235
<212> TYPE: PRT
<213> ORGANISM: Artificial Sequence
<220> FEATURE:
<223> OTHER INFORMATION: Synthetic Construct

<400> SEQUENCE: 57

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Phe Asp Tyr Leu Gly Trp Tyr Gln Gln Lys Pro Gly Gln Ala
    50                  55                  60

Pro Arg Leu Leu Ile Tyr Gly Ala Ser Asn Arg Ala Thr Gly Val Pro
65                  70                  75                  80

Ala Arg Phe Ser Gly Ser Gly Ser Gly Thr Asp Phe Thr Leu Thr Ile
```

```
                    85                  90                  95
Ser Ser Leu Glu Pro Glu Asp Phe Ala Thr Tyr Tyr Cys Phe Gln Tyr
            100                 105                 110

Leu Ile Val Pro Phe Thr Phe Gly Gln Gly Thr Lys Val Glu Ile Lys
            115                 120                 125

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys
225                 230                 235

<210> SEQ ID NO 58
<211> LENGTH: 708
<212> TYPE: DNA
<213> ORGANISM: Artificial Sequence
<220> FEATURE:
<223> OTHER INFORMATION: MOR07924 light chain
<220> FEATURE:
<221> NAME/KEY: CDS
<222> LOCATION: (1)..(708)

<400> SEQUENCE: 58 atg gtg ttg cag acc cag gtc ttc att tct ctg ttg ctc tgg atc tct      48
Met Val Leu Gln Thr Gln Val Phe Ile Ser Leu Leu Leu Trp Ile Ser
1               5                   10                  15 ggt gcc tac ggg gat atc gtg ctg acc cag agc ccg gcg acc ctg agc      96
Gly Ala Tyr Gly Asp Ile Val Leu Thr Gln Ser Pro Ala Thr Leu Ser
                20                  25                  30 ctg tct ccg ggc gaa cgt gcg acc ctg agc tgc aga gcg agc cag tct     144
Leu Ser Pro Gly Glu Arg Ala Thr Leu Ser Cys Arg Ala Ser Gln Ser
            35                  40                  45 gtt tct ttt gat tat ctg ggt tgg tac cag cag aaa cca ggt caa gca     192
Val Ser Phe Asp Tyr Leu Gly Trp Tyr Gln Gln Lys Pro Gly Gln Ala
        50                  55                  60 ccg cgt cta tta att tat ggt gct tct aat cgt gca act ggg gtc ccg     240
Pro Arg Leu Leu Ile Tyr Gly Ala Ser Asn Arg Ala Thr Gly Val Pro
65                  70                  75                  80 gcg cgt ttt agc ggc tct gga tcc ggc acg gat ttt acc ctg acc att     288
Ala Arg Phe Ser Gly Ser Gly Ser Gly Thr Asp Phe Thr Leu Thr Ile
                85                  90                  95 agc agc ctg gaa cct gaa gac ttt gcg acc tat tat tgc cag cag tat     336
Ser Ser Leu Glu Pro Glu Asp Phe Ala Thr Tyr Tyr Cys Gln Gln Tyr
            100                 105                 110 aat att aat cct ttt acc ttt ggc cag ggt acg aaa gtt gaa att aaa     384
Asn Ile Asn Pro Phe Thr Phe Gly Gln Gly Thr Lys Val Glu Ile Lys
        115                 120                 125 cgt acg gtg gct gca cca tct gtc ttc atc ttc ccg cca tct gat gag     432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc     480
```

```
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa    528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc    576
Ser Gly Asn Ser Gln Glu Ser Val Thr Glu Gln Asp Ser Lys Asp Ser
                180                 185                 190 acc tac agc ctc agc agc acc ctg acg ctg agc aaa gca gac tac gag    624
Thr Tyr Ser Leu Ser Ser Thr Leu Thr Leu Ser Lys Ala Asp Tyr Glu
                195                 200                 205 aaa cac aaa gtc tac gcc tgc gaa gtc acc cat cag ggc ctg agc tcg    672
Lys His Lys Val Tyr Ala Cys Glu Val Thr His Gln Gly Leu Ser Ser
210                 215                 220 ccc gtc aca aag agc ttc aac agg gga gag tgt tag                    708
Pro Val Thr Lys Ser Phe Asn Arg Gly Glu Cys
225                 230                 235

<210> SEQ ID NO 59
<211> LENGTH: 235
<212> TYPE: PRT
<213> ORGANISM: Artificial Sequence
<220> FEATURE:
<223> OTHER INFORMATION: Synthetic Construct

<400> SEQUENCE: 59

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Phe Asp Tyr Leu Gly Trp Tyr Gln Gln Lys Pro Gly Gln Ala
        50                  55                  60

Pro Arg Leu Leu Ile Tyr Gly Ala Ser Asn Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Thr Tyr Tyr Cys Gln Gln Tyr
            100                 105                 110

Asn Ile Asn Pro Phe Thr Phe Gly Gln Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235
```

<210> SEQ ID NO 60
<211> LENGTH: 708
<212> TYPE: DNA
<213> ORGANISM: Artificial Sequence
<220> FEATURE:
<223> OTHER INFORMATION: MOR07925 light chain
<220> FEATURE:
<221> NAME/KEY: CDS
<222> LOCATION: (1)..(708)

<400> SEQUENCE: 60

```
atg gtg ttg cag acc cag gtc ttc att tct ctg ttg ctc tgg atc tct      48
Met Val Leu Gln Thr Gln Val Phe Ile Ser Leu Leu Leu Trp Ile Ser
1               5                  10                  15 ggt gcc tac ggg gat atc gtg ctg acc cag agc ccg gcg acc ctg agc      96
Gly Ala Tyr Gly Asp Ile Val Leu Thr Gln Ser Pro Ala Thr Leu Ser
            20                  25                  30 ctg tct ccg ggc gaa cgt gcg acc ctg agc tgc aga gcg agc cag tct     144
Leu Ser Pro Gly Glu Arg Ala Thr Leu Ser Cys Arg Ala Ser Gln Ser
        35                  40                  45 gtt tct ttt gat tat ctg ggt tgg tac cag cag aaa cca ggt caa gca     192
Val Ser Phe Asp Tyr Leu Gly Trp Tyr Gln Gln Lys Pro Gly Gln Ala
    50                  55                  60 ccg cgt cta tta att tat ggt gct tct aat cgt gca act ggg gtc ccg     240
Pro Arg Leu Leu Ile Tyr Gly Ala Ser Asn Arg Ala Thr Gly Val Pro
65                  70                  75                  80 gcg cgt ttt agc ggc tct gga tcc ggc acg gat ttt acc ctg acc att     288
Ala Arg Phe Ser Gly Ser Gly Ser Gly Thr Asp Phe Thr Leu Thr Ile
                85                  90                  95 agc agc ctg gaa cct gaa gac ttt gcg acc tat tat tgc ctt cag tat     336
Ser Ser Leu Glu Pro Glu Asp Phe Ala Thr Tyr Tyr Cys Leu Gln Tyr
            100                 105                 110 ttt aat cct cct cat acc ttt ggc cag ggt acg aaa gtt gaa att aaa     384
Phe Asn Pro Pro His Thr Phe Gly Gln Gly Thr Lys Val Glu Ile Lys
        115                 120                 125 cgt acg gtg gct gca cca tct gtc ttc atc ttc ccg cca tct gat gag     432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc     480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa     528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc     576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag     624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg     672
Lys His Lys Val Tyr Ala Cys Glu Val Thr His Gln Gly Leu Ser Ser
    210                 215                 220 ccc gtc aca aag agc ttc aac agg gga gag tgt tag                     708
Pro Val Thr Lys Ser Phe Asn Arg Gly Glu Cys
225                 230                 235
```

<210> SEQ ID NO 61
<211> LENGTH: 235
<212> TYPE: PRT
<213> ORGANISM: Artificial Sequence
<220> FEATURE:
<223> OTHER INFORMATION: Synthetic Construct

<400> SEQUENCE: 61

Met Val Leu Gln Thr Gln Val Phe Ile Ser Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Phe Asp Tyr Leu Gly Trp Tyr Gln Gln Lys Pro Gly Gln Ala
    50                  55                  60

Pro Arg Leu Leu Ile Tyr Gly Ala Ser Asn Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Thr Tyr Tyr Cys Leu Gln Tyr
            100                 105                 110

Phe Asn Pro Pro His Thr Phe Gly Gln Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 62
<211> LENGTH: 708
<212> TYPE: DNA
<213> ORGANISM: Artificial Sequence
<220> FEATURE:
<223> OTHER INFORMATION: MOR07926 light chain
<220> FEATURE:
<221> NAME/KEY: CDS
<222> LOCATION: (1)..(708)

<400> SEQUENCE: 62 atg gtg ttg cag acc cag gtc ttc att tct ctg ttg ctc tgg atc tct    48
Met Val Leu Gln Thr Gln Val Phe Ile Ser Leu Leu Trp Ile Ser
1               5                   10                  15 ggt gcc tac ggg gat atc gtg ctg acc cag agc ccg gcg acc ctg agc    96
Gly Ala Tyr Gly Asp Ile Val Leu Thr Gln Ser Pro Ala Thr Leu Ser
            20                  25                  30 ctg tct ccg ggc gaa cgt gcg acc ctg agc tgc aga gcg agc cag tct   144
Leu Ser Pro Gly Glu Arg Ala Thr Leu Ser Cys Arg Ala Ser Gln Ser
        35                  40                  45 gtt tct ttt gat tat ctg ggt tgg tac cag cag aaa cca ggt caa gca   192
Val Ser Phe Asp Tyr Leu Gly Trp Tyr Gln Gln Lys Pro Gly Gln Ala
    50                  55                  60 ccg cgt cta tta att tat ggt gct tct aat cgt gca act ggg gtc ccg   240
Pro Arg Leu Leu Ile Tyr Gly Ala Ser Asn Arg Ala Thr Gly Val Pro
65                  70                  75                  80

```
                    65                  70                  75                  80
gcg cgt ttt agc ggc tct gga tcc ggc acg gat ttt acc ctg acc att         288
Ala Arg Phe Ser Gly Ser Gly Ser Gly Thr Asp Phe Thr Leu Thr Ile
                85                  90                  95 agc agc ctg gaa cct gaa gac ttt gcg acc tat tat tgc ttt cag gct         336
Ser Ser Leu Glu Pro Glu Asp Phe Ala Thr Tyr Tyr Cys Phe Gln Ala
            100                 105                 110 ctt att atg cct ttt acc ttt ggc cag ggt acg aaa gtt gaa att aaa         384
Leu Ile Met Pro Phe Thr Phe Gly Gln Gly Thr Lys Val Glu Ile Lys
        115                 120                 125 cgt acg gtg gct gca cca tct gtc ttc atc ttc ccg cca tct gat gag         432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc         480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa         528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc         576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag         624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg         672
Lys His Lys Val Tyr Ala Cys Glu Val Thr His Gln Gly Leu Ser Ser
    210                 215                 220 ccc gtc aca aag agc ttc aac agg gga gag tgt tag                         708
Pro Val Thr Lys Ser Phe Asn Arg Gly Glu Cys
225                 230                 235

<210> SEQ ID NO 63
<211> LENGTH: 235
<212> TYPE: PRT
<213> ORGANISM: Artificial Sequence
<220> FEATURE:
<223> OTHER INFORMATION: Synthetic Construct

<400> SEQUENCE: 63

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Phe Asp Tyr Leu Gly Trp Tyr Gln Gln Lys Pro Gly Gln Ala
    50                  55                  60

Pro Arg Leu Leu Ile Tyr Gly Ala Ser Asn Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Thr Tyr Tyr Cys Phe Gln Ala
            100                 105                 110

Leu Ile Met Pro Phe Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140
```

```
Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
        180                 185                 190

Thr Tyr Ser Leu Ser Ser Thr Leu Thr Leu Ser Lys Ala Asp Tyr Glu
    195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 64
<211> LENGTH: 1551
<212> TYPE: DNA
<213> ORGANISM: Artificial Sequence
<220> FEATURE:
<223> OTHER INFORMATION: MOR7919 heavy chain
<220> FEATURE:
<221> NAME/KEY: CDS
<222> LOCATION: (45)..(1457)

<400> SEQUENCE: 64
taatacgact cactataggg agacccaagc tggctagcgc cacc atg aaa cac ctg      56
                                              Met Lys His Leu
                                                1 tgg ttc ttc ctc ctg ctg gtg gca gct ccc aga tgg gtc ctg tcc cag    104
Trp Phe Phe Leu Leu Leu Val Ala Ala Pro Arg Trp Val Leu Ser Gln
  5              10                  15                  20 gtg caa ttg gtt cag agc ggc gcg gaa gtg aaa aaa ccg ggc gaa agc    152
Val Gln Leu Val Gln Ser Gly Ala Glu Val Lys Lys Pro Gly Glu Ser
             25                  30                  35 ctg aaa att agc tgc aaa ggt tcc gga tat tcc ttt act aat tat tgg    200
Leu Lys Ile Ser Cys Lys Gly Ser Gly Tyr Ser Phe Thr Asn Tyr Trp
         40                  45                  50 att tct tgg gtg cgc cag atg cct ggg aag ggt ctc gag tgg atg ggc    248
Ile Ser Trp Val Arg Gln Met Pro Gly Lys Gly Leu Glu Trp Met Gly
     55                  60                  65 ttt atc tat ccg gat gat agc tat acc cgt tat tct ccg agc ttt cag    296
Phe Ile Tyr Pro Asp Asp Ser Tyr Thr Arg Tyr Ser Pro Ser Phe Gln
 70                  75                  80 ggc cag gtg acc att agc gcg gat aaa agc att agc acc gcg tat ctt    344
Gly Gln Val Thr Ile Ser Ala Asp Lys Ser Ile Ser Thr Ala Tyr Leu
85                  90                  95                 100 caa tgg agc agc ctg aaa gcg agc gat acg gcc atg tat tat tgc gcg    392
Gln Trp Ser Ser Leu Lys Ala Ser Asp Thr Ala Met Tyr Tyr Cys Ala
                105                 110                 115 cgt ttt tct tat cgt cat tat ctt gat atg gat gat cat tgg ggc caa    440
Arg Phe Ser Tyr Arg His Tyr Leu Asp Met Asp Asp His Trp Gly Gln
            120                 125                 130 ggc acc ctg gtg acg gtt agc tca gcc tcc acc aag ggt cca tcg gtc    488
Gly Thr Leu Val Thr Val Ser Ser Ala Ser Thr Lys Gly Pro Ser Val
        135                 140                 145 ttc ccc ctg gca ccc tcc tcc aag agc acc tct ggg ggc aca gcg gcc    536
Phe Pro Leu Ala Pro Ser Ser Lys Ser Thr Ser Gly Gly Thr Ala Ala
    150                 155                 160 ctg ggc tgc ctg gtc aag gac tac ttc ccc gaa ccg gtg acg gtg tcg    584
Leu Gly Cys Leu Val Lys Asp Tyr Phe Pro Glu Pro Val Thr Val Ser
165                 170                 175                 180
```

-continued

| | | |
|---|---|---|
| tgg aac tca ggc gcc ctg acc agc ggc gtg cac acc ttc ccg gct gtc<br>Trp Asn Ser Gly Ala Leu Thr Ser Gly Val His Thr Phe Pro Ala Val<br>185 190 195 | 632 | |
| cta cag tcc tca gga ctc tac tcc ctc agc agc gtg gtg acc gtg ccc<br>Leu Gln Ser Ser Gly Leu Tyr Ser Leu Ser Ser Val Val Thr Val Pro<br>200 205 210 | 680 | |
| tcc agc agc ttg ggc acc cag acc tac atc tgc aac gta aat cac aag<br>Ser Ser Ser Leu Gly Thr Gln Thr Tyr Ile Cys Asn Val Asn His Lys<br>215 220 225 | 728 | |
| ccc agc aac acc aag gtg gac aag aga gtt gag ccc aaa tct tgt gac<br>Pro Ser Asn Thr Lys Val Asp Lys Arg Val Glu Pro Lys Ser Cys Asp<br>230 235 240 | 776 | |
| aaa act cac aca tgc cca ccg tgc cca gca cct gaa ctc ctg ggg gga<br>Lys Thr His Thr Cys Pro Pro Cys Pro Ala Pro Glu Leu Leu Gly Gly<br>245 250 255 260 | 824 | |
| ccg tca gtc ttc ctc ttc ccc cca aaa ccc aag gac acc ctc atg atc<br>Pro Ser Val Phe Leu Phe Pro Pro Lys Pro Lys Asp Thr Leu Met Ile<br>265 270 275 | 872 | |
| tcc cgg acc cct gag gtc aca tgc gtg gtg gtg gac gtg agc cac gaa<br>Ser Arg Thr Pro Glu Val Thr Cys Val Val Val Asp Val Ser His Glu<br>280 285 290 | 920 | |
| gac cct gag gtc aag ttc aac tgg tac gtg gac ggc gtg gag gtg cat<br>Asp Pro Glu Val Lys Phe Asn Trp Tyr Val Asp Gly Val Glu Val His<br>295 300 305 | 968 | |
| aat gcc aag aca aag ccg cgg gag gag cag tac aac agc acg tac cgg<br>Asn Ala Lys Thr Lys Pro Arg Glu Glu Gln Tyr Asn Ser Thr Tyr Arg<br>310 315 320 | 1016 | |
| gtg gtc agc gtc ctc acc gtc ctg cac cag gac tgg ctg aat ggc aag<br>Val Val Ser Val Leu Thr Val Leu His Gln Asp Trp Leu Asn Gly Lys<br>325 330 335 340 | 1064 | |
| gag tac aag tgc aag gtc tcc aac aaa gcc ctc cca gcc ccc atc gag<br>Glu Tyr Lys Cys Lys Val Ser Asn Lys Ala Leu Pro Ala Pro Ile Glu<br>345 350 355 | 1112 | |
| aaa acc atc tcc aaa gcc aaa ggg cag ccc cga gaa cca cag gtg tac<br>Lys Thr Ile Ser Lys Ala Lys Gly Gln Pro Arg Glu Pro Gln Val Tyr<br>360 365 370 | 1160 | |
| acc ctg ccc cca tcc cgg gag gag atg acc aag aac cag gtc agc ctg<br>Thr Leu Pro Pro Ser Arg Glu Glu Met Thr Lys Asn Gln Val Ser Leu<br>375 380 385 | 1208 | |
| acc tgc ctg gtc aaa ggc ttc tat ccc agc gac atc gcc gtg gag tgg<br>Thr Cys Leu Val Lys Gly Phe Tyr Pro Ser Asp Ile Ala Val Glu Trp<br>390 395 400 | 1256 | |
| gag agc aat ggg cag ccg gag aac aac tac aag acc acg cct ccc gtg<br>Glu Ser Asn Gly Gln Pro Glu Asn Asn Tyr Lys Thr Thr Pro Pro Val<br>405 410 415 420 | 1304 | |
| ctg gac tcc gac ggc tcc ttc ttc ctc tac agc aag ctc acc gtg gac<br>Leu Asp Ser Asp Gly Ser Phe Phe Leu Tyr Ser Lys Leu Thr Val Asp<br>425 430 435 | 1352 | |
| aag agc agg tgg cag cag ggg aac gtc ttc tca tgc tcc gtg atg cat<br>Lys Ser Arg Trp Gln Gln Gly Asn Val Phe Ser Cys Ser Val Met His<br>440 445 450 | 1400 | |
| gag gct ctg cac aac cac tac acg cag aag agc ctc tcc ctg tct ccg<br>Glu Ala Leu His Asn His Tyr Thr Gln Lys Ser Leu Ser Leu Ser Pro<br>455 460 465 | 1448 | |
| ggt aaa tga gggcccgttt aaacgggtgg catccctgtg acccctcccc<br>Gly Lys<br>470 | 1497 | |
| agtgcctctc ctggccctgg aagttgccac tccagtgccc accagccttg tcct | 1551 | |

```
<210> SEQ ID NO 65
<211> LENGTH: 470
<212> TYPE: PRT
<213> ORGANISM: Artificial Sequence
<220> FEATURE:
<223> OTHER INFORMATION: Synthetic Construct

<400> SEQUENCE: 65

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Asn Tyr Trp Ile Ser Trp Val Arg Gln Met Pro Gly Lys Gly Leu
    50                  55                  60

Glu Trp Met Gly Phe Ile Tyr Pro Asp Asp Ser Tyr Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Phe Ser Tyr Arg His Tyr Leu Asp Met Asp Asp
        115                 120                 125

His Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
```

```
                 370                375                380
Gln Val Ser Leu Thr Cys Leu Val Lys Gly Phe Tyr Pro Ser Asp Ile
385                390                395                400

Ala Val Glu Trp Glu Ser Asn Gly Gln Pro Glu Asn Asn Tyr Lys Thr
                405                410                415

Thr Pro Pro Val Leu Asp Ser Asp Gly Ser Phe Phe Leu Tyr Ser Lys
                420                425                430

Leu Thr Val Asp Lys Ser Arg Trp Gln Gln Gly Asn Val Phe Ser Cys
                435                440                445

Ser Val Met His Glu Ala Leu His Asn His Tyr Thr Gln Lys Ser Leu
    450                455                460

Ser Leu Ser Pro Gly Lys
465                470

<210> SEQ ID NO 66
<211> LENGTH: 1539
<212> TYPE: DNA
<213> ORGANISM: Artificial Sequence
<220> FEATURE:
<223> OTHER INFORMATION: MOR7692, MOR7923, MOR7924, MOR7925 and MOR7926
      heavy chain
<220> FEATURE:
<221> NAME/KEY: CDS
<222> LOCATION: (45)..(1445)

<400> SEQUENCE: 66
taatacgact cactataggg agacccaagc tggctagcgc cacc atg aaa cac ctg      56
                                                 Met Lys His Leu
                                                   1 tgg ttc ttc ctc ctg ctg gtg gca gct ccc aga tgg gtc ctg tcc cag     104
Trp Phe Phe Leu Leu Leu Val Ala Ala Pro Arg Trp Val Leu Ser Gln
  5              10                 15                 20 gtg caa ttg gtg gaa agc ggc ggc ggc ctg gtg caa ccg ggc ggc agc     152
Val Gln Leu Val Glu Ser Gly Gly Gly Leu Val Gln Pro Gly Gly Ser
             25                 30                 35 ctg cgt ctg agc tgc gcg gcc tcc gga ttt acc ttt aat tct tat tct     200
Leu Arg Leu Ser Cys Ala Ala Ser Gly Phe Thr Phe Asn Ser Tyr Ser
         40                 45                 50 atg tct tgg gtg cgc caa gcc cct ggg aag ggt ctc gag tgg gtg agc     248
Met Ser Trp Val Arg Gln Ala Pro Gly Lys Gly Leu Glu Trp Val Ser
     55                 60                 65 tat atc tct tct cgt tct agc act acc tat tat gcg gat agc gtg aaa     296
Tyr Ile Ser Ser Arg Ser Ser Thr Thr Tyr Tyr Ala Asp Ser Val Lys
 70                 75                 80 ggc cgt ttt acc att tca cgt gat aat tcg aaa aac acc ctg tat ctg     344
Gly Arg Phe Thr Ile Ser Arg Asp Asn Ser Lys Asn Thr Leu Tyr Leu
85                  90                 95                100 caa atg aac agc ctg cgt gcg gaa gat acg gcc gtg tat tat tgc gcg     392
Gln Met Asn Ser Leu Arg Ala Glu Asp Thr Ala Val Tyr Tyr Cys Ala
                105                110                115 cgt ggt tat ttt cat ggt atg gat tat tgg ggc caa ggc acc ctg gtg     440
Arg Gly Tyr Phe His Gly Met Asp Tyr Trp Gly Gln Gly Thr Leu Val
            120                125                130 acg gtt agc tca gcc tcc acc aag ggt cca tcg gtc ttc ccc ctg gca     488
Thr Val Ser Ser Ala Ser Thr Lys Gly Pro Ser Val Phe Pro Leu Ala
        135                140                145 ccc tcc tcc aag agc acc tct ggg ggc aca gcg gcc ctg ggc tgc ctg     536
Pro Ser Ser Lys Ser Thr Ser Gly Gly Thr Ala Ala Leu Gly Cys Leu
    150                155                160 gtc aag gac tac ttc ccc gaa ccg gtg acg gtg tcg tgg aac tca ggc     584
```

```

Val Lys Asp Tyr Phe Pro Glu Pro Val Thr Val Ser Trp Asn Ser Gly
165                 170                 175                 180 gcc ctg acc agc ggc gtg cac acc ttc ccg gct gtc cta cag tcc tca       632
Ala Leu Thr Ser Gly Val His Thr Phe Pro Ala Val Leu Gln Ser Ser
                185                 190                 195 gga ctc tac tcc ctc agc agc gtg gtg acc gtg ccc tcc agc agc ttg       680
Gly Leu Tyr Ser Leu Ser Ser Val Val Thr Val Pro Ser Ser Ser Leu
                200                 205                 210 ggc acc cag acc tac atc tgc aac gtg aat cac aag ccc agc aac acc       728
Gly Thr Gln Thr Tyr Ile Cys Asn Val Asn His Lys Pro Ser Asn Thr
                215                 220                 225 aag gtg gac aag aga gtt gag ccc aaa tct tgt gac aaa act cac aca       776
Lys Val Asp Lys Arg Val Glu Pro Lys Ser Cys Asp Lys Thr His Thr
        230                 235                 240 tgc cca ccg tgc cca gca cct gaa ctc ctg ggg gga ccg tca gtc ttc       824
Cys Pro Pro Cys Pro Ala Pro Glu Leu Leu Gly Gly Pro Ser Val Phe
245                 250                 255                 260 ctc ttc ccc cca aaa ccc aag gac acc ctc atg atc tcc cgg acc cct       872
Leu Phe Pro Pro Lys Pro Lys Asp Thr Leu Met Ile Ser Arg Thr Pro
                265                 270                 275 gag gtc aca tgc gtg gtg gtg gac gtg agc cac gaa gac cct gag gtc       920
Glu Val Thr Cys Val Val Val Asp Val Ser His Glu Asp Pro Glu Val
                280                 285                 290 aag ttc aac tgg tac gtg gac ggc gtg gag gtg cat aat gcc aag aca       968
Lys Phe Asn Trp Tyr Val Asp Gly Val Glu Val His Asn Ala Lys Thr
                295                 300                 305 aag ccg cgg gag gag cag tac aac agc acg tac cgg gtg gtc agc gtc      1016
Lys Pro Arg Glu Glu Gln Tyr Asn Ser Thr Tyr Arg Val Val Ser Val
        310                 315                 320 ctc acc gtc ctg cac cag gac tgg ctg aat ggc aag gag tac aag tgc      1064
Leu Thr Val Leu His Gln Asp Trp Leu Asn Gly Lys Glu Tyr Lys Cys
325                 330                 335                 340 aag gtc tcc aac aaa gcc ctc cca gcc ccc atc gag aaa acc atc tcc      1112
Lys Val Ser Asn Lys Ala Leu Pro Ala Pro Ile Glu Lys Thr Ile Ser
                345                 350                 355 aaa gcc aaa ggg cag ccc cga gaa cca cag gtg tac acc ctg ccc cca      1160
Lys Ala Lys Gly Gln Pro Arg Glu Pro Gln Val Tyr Thr Leu Pro Pro
                360                 365                 370 tcc cgg gag gag atg acc aag aac cag gtc agc ctg acc tgc ctg gtc      1208
Ser Arg Glu Glu Met Thr Lys Asn Gln Val Ser Leu Thr Cys Leu Val
        375                 380                 385 aaa ggc ttc tat ccc agc gac atc gcc gtg gag tgg gag agc aat ggg      1256
Lys Gly Phe Tyr Pro Ser Asp Ile Ala Val Glu Trp Glu Ser Asn Gly
390                 395                 400 cag ccg gag aac aac tac aag acc acg cct ccc gtg ctg gac tcc gac      1304
Gln Pro Glu Asn Asn Tyr Lys Thr Thr Pro Pro Val Leu Asp Ser Asp
405                 410                 415                 420 ggc tcc ttc ttc ctc tac agc aag ctc acc gtg gac aag agc agg tgg      1352
Gly Ser Phe Phe Leu Tyr Ser Lys Leu Thr Val Asp Lys Ser Arg Trp
                425                 430                 435 cag cag ggg aac gtc ttc tca tgc tcc gtg atg cat gag gct ctg cac      1400
Gln Gln Gly Asn Val Phe Ser Cys Ser Val Met His Glu Ala Leu His
                440                 445                 450 aac cac tac acg cag aag agc ctc tcc ctg tct ccg ggt aaa tga          1445
Asn His Tyr Thr Gln Lys Ser Leu Ser Leu Ser Pro Gly Lys
                455                 460                 465 gggcccgttt aaacgggtgg catccctgtg acccctcccc agtgcctctc ctggccctgg    1505
aagttgccac tccagtgccc accagccttg tcct                                1539
```

<210> SEQ ID NO 67
<211> LENGTH: 466
<212> TYPE: PRT
<213> ORGANISM: Artificial Sequence
<220> FEATURE:
<223> OTHER INFORMATION: Synthetic Construct

<400> SEQUENCE: 67

```
Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Asn Ser Tyr Ser Met Ser Trp Val Arg Gln Ala Pro Gly Lys Gly Leu
    50                  55                  60

Glu Trp Val Ser Tyr Ile Ser Ser Arg Ser Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Tyr Phe His Gly Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365
```

```
Thr Leu Pro Pro Ser Arg Glu Glu Met Thr Lys Asn Gln Val Ser Leu
    370             375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 68
<211> LENGTH: 840
<212> TYPE: DNA
<213> ORGANISM: Artificial Sequence
<220> FEATURE:
<223> OTHER INFORMATION: MOR07919 lambda light chain
<220> FEATURE:
<221> NAME/KEY: CDS
<222> LOCATION: (45)..(746)

<400> SEQUENCE: 68
taatacgact cactataggg agacccaagc tggctagcgc cacc atg gcc tgg gct      56
                                                 Met Ala Trp Ala
                                                   1 ctg ctg ctc ctc acc ctc ctc act cag ggc aca gga tcc tgg gct gat     104
Leu Leu Leu Leu Thr Leu Leu Thr Gln Gly Thr Gly Ser Trp Ala Asp
  5              10                  15                  20 atc gaa ctg acc cag ccg cct tca gtg agc gtt gca cca ggt cag acc     152
Ile Glu Leu Thr Gln Pro Pro Ser Val Ser Val Ala Pro Gly Gln Thr
             25                  30                  35 gcg cgt atc tcg tgt agc ggc gat tct ctt ggt tct aag tat gtt cat     200
Ala Arg Ile Ser Cys Ser Gly Asp Ser Leu Gly Ser Lys Tyr Val His
         40                  45                  50 tgg tac cag cag aaa ccc ggg cag gcg cca gtt ctt gtg att tat cgt     248
Trp Tyr Gln Gln Lys Pro Gly Gln Ala Pro Val Leu Val Ile Tyr Arg
     55                  60                  65 gat aat aag cgt ccc tca ggc atc ccg gaa cgc ttt agc gga tcc aac     296
Asp Asn Lys Arg Pro Ser Gly Ile Pro Glu Arg Phe Ser Gly Ser Asn
 70                  75                  80 agc ggc aac acc gcg acc ctg acc att agc ggc act cag gcg gaa gac     344
Ser Gly Asn Thr Ala Thr Leu Thr Ile Ser Gly Thr Gln Ala Glu Asp
 85                  90                  95                 100 gaa gcg gat tat tat tgc cag tct tat gat gct act gag ttt act tat     392
Glu Ala Asp Tyr Tyr Cys Gln Ser Tyr Asp Ala Thr Glu Phe Thr Tyr
                105                 110                 115 gtg ttt ggc ggc ggc acg aag tta acc gtc cta ggt cag ccc aag gct     440
Val Phe Gly Gly Gly Thr Lys Leu Thr Val Leu Gly Gln Pro Lys Ala
            120                 125                 130 gcc ccc tcg gtc act ctg ttc ccg ccc tcc tct gag gag ctt caa gcc     488
Ala Pro Ser Val Thr Leu Phe Pro Pro Ser Ser Glu Glu Leu Gln Ala
        135                 140                 145 aac aag gcc aca ctg gtg tgt ctc ata agt gac ttc tac ccg gga gcc     536
Asn Lys Ala Thr Leu Val Cys Leu Ile Ser Asp Phe Tyr Pro Gly Ala
    150                 155                 160 gtg aca gtg gcc tgg aag gca gat agc agc ccc gtc aag gcg gga gtg     584
```

```
Val Thr Val Ala Trp Lys Ala Asp Ser Ser Pro Val Lys Ala Gly Val
165                 170                 175                 180 gag acc acc aca ccc tcc aaa caa agc aac aac aag tac gcg gcc agc        632
Glu Thr Thr Thr Pro Ser Lys Gln Ser Asn Asn Lys Tyr Ala Ala Ser
                185                 190                 195 agc tat ctg agc ctg acg cct gag cag tgg aag tcc cac aga agc tac        680
Ser Tyr Leu Ser Leu Thr Pro Glu Gln Trp Lys Ser His Arg Ser Tyr
            200                 205                 210 agc tgc cag gtc acg cat gaa ggg agc acc gtg gag aag aca gtg gcc        728
Ser Cys Gln Val Thr His Glu Gly Ser Thr Val Glu Lys Thr Val Ala
        215                 220                 225 cct aca gaa tgt tca tag gggcccgttt aaacgggtgg catccctgtg               776
Pro Thr Glu Cys Ser
    230 acccctcccc agtgcctctc ctggccctgg aagttgccac tccagtgccc accagccttg      836 tcct                                                                    840

<210> SEQ ID NO 69
<211> LENGTH: 233
<212> TYPE: PRT
<213> ORGANISM: Artificial Sequence
<220> FEATURE:
<223> OTHER INFORMATION: Synthetic Construct

<400> SEQUENCE: 69

Met Ala Trp Ala Leu Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
            20                  25                  30

Pro Gly Gln Thr Ala Arg Ile Ser Cys Ser Gly Asp Ser Leu Gly Ser
        35                  40                  45

Lys Tyr Val His Trp Tyr Gln Gln Lys Pro Gly Gln Ala Pro Val Leu
    50                  55                  60

Val Ile Tyr Arg Asp Asn Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Gln Ser Tyr Asp Ala Thr
            100                 105                 110

Glu Phe Thr Tyr Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 70
<211> LENGTH: 846
<212> TYPE: DNA
<213> ORGANISM: Artificial Sequence
<220> FEATURE:
<223> OTHER INFORMATION: MOR07692 kappa light chain
<220> FEATURE:
<221> NAME/KEY: CDS
<222> LOCATION: (45)..(752)

<400> SEQUENCE: 70

```
taatacgact cactataggg agacccaagc tggctagcgc cacc atg gtg ttg cag        56
                                                Met Val Leu Gln
                                                 1 acc cag gtc ttc att tct ctg ttg ctc tgg atc tct ggt gcc tac ggg       104
Thr Gln Val Phe Ile Ser Leu Leu Leu Trp Ile Ser Gly Ala Tyr Gly
 5                  10                  15                  20 gat atc gtg ctg acc cag agc ccg gcg acc ctg agc ctg tct ccg ggc       152
Asp Ile Val Leu Thr Gln Ser Pro Ala Thr Leu Ser Leu Ser Pro Gly
                 25                  30                  35 gaa cgt gcg acc ctg agc tgc aga gcg agc cag tct gtt tct ttt gat       200
Glu Arg Ala Thr Leu Ser Cys Arg Ala Ser Gln Ser Val Ser Phe Asp
             40                  45                  50 tat ctg ggt tgg tac cag cag aaa cca ggt caa gca ccg cgt cta tta       248
Tyr Leu Gly Trp Tyr Gln Gln Lys Pro Gly Gln Ala Pro Arg Leu Leu
         55                  60                  65 att tat ggt gct tct aat cgt gca act ggg gtc ccg gcg cgt ttt agc       296
Ile Tyr Gly Ala Ser Asn Arg Ala Thr Gly Val Pro Ala Arg Phe Ser
     70                  75                  80 ggc tct gga tcc ggc acg gat ttt acc ctg acc att agc agc ctg gaa       344
Gly Ser Gly Ser Gly Thr Asp Phe Thr Leu Thr Ile Ser Ser Leu Glu
 85                  90                  95                 100 cct gaa gac ttt gcg act tat tat tgc cag cag tat tat aat atg cct       392
Pro Glu Asp Phe Ala Thr Tyr Tyr Cys Gln Gln Tyr Tyr Asn Met Pro
                105                 110                 115 tat acc ttt ggc cag ggt acg aaa gtt gaa att aaa cgt acg gtg gct       440
Tyr Thr Phe Gly Gln Gly Thr Lys Val Glu Ile Lys Arg Thr Val Ala
            120                 125                 130 gca cca tct gtc ttc atc ttc ccg cca tct gat gag cag ttg aaa tct       488
Ala Pro Ser Val Phe Ile Phe Pro Pro Ser Asp Glu Gln Leu Lys Ser
        135                 140                 145 gga act gcc tct gtt gtg tgc ctg ctg aat aac ttc tat ccc aga gag       536
Gly Thr Ala Ser Val Val Cys Leu Leu Asn Asn Phe Tyr Pro Arg Glu
    150                 155                 160 gcc aaa gta cag tgg aag gtg gat aac gcc ctc caa tcg ggt aac tcc       584
Ala Lys Val Gln Trp Lys Val Asp Asn Ala Leu Gln Ser Gly Asn Ser
165                 170                 175                 180 cag gag agt gtc aca gag cag gac agc aag gac agc acc tac agc ctc       632
Gln Glu Ser Val Thr Glu Gln Asp Ser Lys Asp Ser Thr Tyr Ser Leu
                185                 190                 195 agc agc acc ctg acg ctg agc aaa gca gac tac gag aaa cac aaa gtc       680
Ser Ser Thr Leu Thr Leu Ser Lys Ala Asp Tyr Glu Lys His Lys Val
            200                 205                 210 tac gcc tgc gaa gtc acc cat cag ggc ctg agc tcg ccc gtc aca aag       728
Tyr Ala Cys Glu Val Thr His Gln Gly Leu Ser Ser Pro Val Thr Lys
        215                 220                 225 agc ttc aac agg gga gag tgt tag gggcccgttt aaacgggtgg catccctgtg      782
Ser Phe Asn Arg Gly Glu Cys
    230                 235 acccctcccc agtgcctctc ctggccctgg aagttgccac tccagtgccc accagccttg     842
tcct                                                                  846
```

<210> SEQ ID NO 71
<211> LENGTH: 235
<212> TYPE: PRT
<213> ORGANISM: Artificial Sequence
<220> FEATURE:
<223> OTHER INFORMATION: Synthetic Construct

<400> SEQUENCE: 71

```
Met Val Leu Gln Thr Gln Val Phe Ile Ser Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Phe Asp Tyr Leu Gly Trp Tyr Gln Gln Lys Pro Gly Gln Ala
    50                  55                  60

Pro Arg Leu Leu Ile Tyr Gly Ala Ser Asn Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Thr Tyr Tyr Cys Gln Gln Tyr
            100                 105                 110

Tyr Asn Met Pro Tyr Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 72
<211> LENGTH: 846
<212> TYPE: DNA
<213> ORGANISM: Artificial Sequence
<220> FEATURE:
<223> OTHER INFORMATION: MOR07923 kappa light chain
<220> FEATURE:
<221> NAME/KEY: CDS
<222> LOCATION: (45)..(752)

<400> SEQUENCE: 72

```
taatacgact cactataggg agacccaagc tggctagcgc cacc atg gtg ttg cag        56
                                                Met Val Leu Gln
                                                1 acc cag gtc ttc att tct ctg ttg ctc tgg atc tct ggt gcc tac ggg       104
Thr Gln Val Phe Ile Ser Leu Leu Leu Trp Ile Ser Gly Ala Tyr Gly
5                   10                  15                  20 gat atc gtg ctg acc cag agc ccg gcg acc ctg agc ctg tct ccg ggc       152
Asp Ile Val Leu Thr Gln Ser Pro Ala Thr Leu Ser Leu Ser Pro Gly
```

-continued

```
            25                  30                  35
gaa cgt gcg acc ctg agc tgc aga gcg agc cag tct gtt tct ttt gat    200
Glu Arg Ala Thr Leu Ser Cys Arg Ala Ser Gln Ser Val Ser Phe Asp
            40                  45                  50 tat ctg ggt tgg tac cag cag aaa cca ggt caa gca ccg cgt cta tta    248
Tyr Leu Gly Trp Tyr Gln Gln Lys Pro Gly Gln Ala Pro Arg Leu Leu
        55                  60                  65 att tat ggt gct tct aat cgt gca act ggg gtc ccg gcg cgt ttt agc    296
Ile Tyr Gly Ala Ser Asn Arg Ala Thr Gly Val Pro Ala Arg Phe Ser
    70                  75                  80 ggc tct gga tcc ggc acg gat ttt acc ctg acc att agc agc ctg gaa    344
Gly Ser Gly Ser Gly Thr Asp Phe Thr Leu Thr Ile Ser Ser Leu Glu
85                  90                  95                 100 cct gaa gac ttt gcg acc tat tat tgc ttt cag tat ctt att gtt cct    392
Pro Glu Asp Phe Ala Thr Tyr Tyr Cys Phe Gln Tyr Leu Ile Val Pro
                105                 110                 115 ttt acc ttt ggc cag ggt acg aaa gtt gaa att aaa cgt acg gtg gct    440
Phe Thr Phe Gly Gln Gly Thr Lys Val Glu Ile Lys Arg Thr Val Ala
            120                 125                 130 gca cca tct gtc ttc atc ttc ccg cca tct gat gag cag ttg aaa tct    488
Ala Pro Ser Val Phe Ile Phe Pro Pro Ser Asp Glu Gln Leu Lys Ser
        135                 140                 145 gga act gcc tct gtt gtg tgc ctg ctg aat aac ttc tat ccc aga gag    536
Gly Thr Ala Ser Val Val Cys Leu Leu Asn Asn Phe Tyr Pro Arg Glu
    150                 155                 160 gcc aaa gta cag tgg aag gtg gat aac gcc ctc caa tcg ggt aac tcc    584
Ala Lys Val Gln Trp Lys Val Asp Asn Ala Leu Gln Ser Gly Asn Ser
165                 170                 175                 180 cag gag agt gtc aca gag cag gac agc aag gac agc acc tac agc ctc    632
Gln Glu Ser Val Thr Glu Gln Asp Ser Lys Asp Ser Thr Tyr Ser Leu
                185                 190                 195 agc agc acc ctg acg ctg agc aaa gca gac tac gag aaa cac aaa gtc    680
Ser Ser Thr Leu Thr Leu Ser Lys Ala Asp Tyr Glu Lys His Lys Val
            200                 205                 210 tac gcc tgc gaa gtc acc cat cag ggc ctg agc tcg ccc gtc aca aag    728
Tyr Ala Cys Glu Val Thr His Gln Gly Leu Ser Ser Pro Val Thr Lys
        215                 220                 225 agc ttc aac agg gga gag tgt tag gggcccgttt aaacgggtgg catccctgtg    782
Ser Phe Asn Arg Gly Glu Cys
    230                 235 acccctcccc agtgcctctc ctggccctgg aagttgccac tccagtgccc accagccttg    842
tcct                                                                 846

<210> SEQ ID NO 73
<211> LENGTH: 235
<212> TYPE: PRT
<213> ORGANISM: Artificial Sequence
<220> FEATURE:
<223> OTHER INFORMATION: Synthetic Construct

<400> SEQUENCE: 73

Met Val Leu Gln Thr Gln Val Phe Ile Ser Leu Leu Trp Ile Ser
1               5                  10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Phe Asp Tyr Leu Gly Trp Tyr Gln Gln Lys Pro Gly Gln Ala
    50                  55                  60
```

```
Pro Arg Leu Leu Ile Tyr Gly Ala Ser Asn Arg Ala Thr Gly Val Pro
65                  70                  75                  80

Ala Arg Phe Ser Gly Ser Gly Ser Gly Thr Asp Phe Thr Leu Thr Ile
            85                  90                  95

Ser Ser Leu Glu Pro Glu Asp Phe Ala Thr Tyr Tyr Cys Phe Gln Tyr
            100                 105                 110

Leu Ile Val Pro Phe Thr Phe Gly Gln Gly Thr Lys Val Glu Ile Lys
            115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 74
<211> LENGTH: 846
<212> TYPE: DNA
<213> ORGANISM: Artificial Sequence
<220> FEATURE:
<223> OTHER INFORMATION: MOR07924 kappa light chain
<220> FEATURE:
<221> NAME/KEY: CDS
<222> LOCATION: (45)..(752)

<400> SEQUENCE: 74
taatacgact cactataggg agacccaagc tggctagcgc cacc atg gtg ttg cag       56
                                                Met Val Leu Gln
                                                1 acc cag gtc ttc att tct ctg ttg ctc tgg atc tct ggt gcc tac ggg      104
Thr Gln Val Phe Ile Ser Leu Leu Leu Trp Ile Ser Gly Ala Tyr Gly
5                   10                  15                  20 gat atc gtg ctg acc cag agc ccg gcg acc ctg agc ctg tct ccg ggc      152
Asp Ile Val Leu Thr Gln Ser Pro Ala Thr Leu Ser Leu Ser Pro Gly
                25                  30                  35 gaa cgt gcg acc ctg agc tgc aga gcg agc cag tct gtt tct ttt gat      200
Glu Arg Ala Thr Leu Ser Cys Arg Ala Ser Gln Ser Val Ser Phe Asp
            40                  45                  50 tat ctg ggt tgg tac cag cag aaa cca ggt caa gca ccg cgt cta tta      248
Tyr Leu Gly Trp Tyr Gln Gln Lys Pro Gly Gln Ala Pro Arg Leu Leu
        55                  60                  65 att tat ggt gct tct aat cgt gca act ggg gtc ccg gcg cgt ttt agc      296
Ile Tyr Gly Ala Ser Asn Arg Ala Thr Gly Val Pro Ala Arg Phe Ser
    70                  75                  80 ggc tct gga tcc ggc acg gat ttt acc ctg acc att agc agc ctg gaa      344
Gly Ser Gly Ser Gly Thr Asp Phe Thr Leu Thr Ile Ser Ser Leu Glu
85                  90                  95                  100 cct gaa gac ttt gcg acc tat tat tgc cag cag tat aat att aat cct      392
Pro Glu Asp Phe Ala Thr Tyr Tyr Cys Gln Gln Tyr Asn Ile Asn Pro
            105                 110                 115
```

```
ttt acc ttt ggc cag ggt acg aaa gtt gaa att aaa cgt acg gtg gct    440
Phe Thr Phe Gly Gln Gly Thr Lys Val Glu Ile Lys Arg Thr Val Ala
            120                 125                 130 gca cca tct gtc ttc atc ttc ccg cca tct gat gag cag ttg aaa tct    488
Ala Pro Ser Val Phe Ile Phe Pro Pro Ser Asp Glu Gln Leu Lys Ser
        135                 140                 145 gga act gcc tct gtt gtg tgc ctg ctg aat aac ttc tat ccc aga gag    536
Gly Thr Ala Ser Val Val Cys Leu Leu Asn Asn Phe Tyr Pro Arg Glu
    150                 155                 160 gcc aaa gta cag tgg aag gtg gat aac gcc ctc caa tcg ggt aac tcc    584
Ala Lys Val Gln Trp Lys Val Asp Asn Ala Leu Gln Ser Gly Asn Ser
165                 170                 175                 180 cag gag agt gtc aca gag cag gac agc aag gac agc acc tac agc ctc    632
Gln Glu Ser Val Thr Glu Gln Asp Ser Lys Asp Ser Thr Tyr Ser Leu
            185                 190                 195 agc agc acc ctg acg ctg agc aaa gca gac tac gag aaa cac aaa gtc    680
Ser Ser Thr Leu Thr Leu Ser Lys Ala Asp Tyr Glu Lys His Lys Val
        200                 205                 210 tac gcc tgc gaa gtc acc cat cag ggc ctg agc tcg ccc gtc aca aag    728
Tyr Ala Cys Glu Val Thr His Gln Gly Leu Ser Ser Pro Val Thr Lys
    215                 220                 225 agc ttc aac agg gga gag tgt tag gggcccgttt aaacgggtgg catccctgtg   782
Ser Phe Asn Arg Gly Glu Cys
230                 235 accccctcccc agtgcctctc ctggccctgg aagttgccac tccagtgccc accagccttg   842
tcct                                                                846

<210> SEQ ID NO 75
<211> LENGTH: 235
<212> TYPE: PRT
<213> ORGANISM: Artificial Sequence
<220> FEATURE:
<223> OTHER INFORMATION: Synthetic Construct

<400> SEQUENCE: 75

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Phe Asp Tyr Leu Gly Trp Tyr Gln Gln Lys Pro Gly Gln Ala
    50                  55                  60

Pro Arg Leu Leu Ile Tyr Gly Ala Ser Asn Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Thr Tyr Tyr Cys Gln Gln Tyr
            100                 105                 110

Asn Ile Asn Pro Phe Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175
```

```
Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 76
<211> LENGTH: 846
<212> TYPE: DNA
<213> ORGANISM: Artificial Sequence
<220> FEATURE:
<223> OTHER INFORMATION: MOR07925 kappa light chain
<220> FEATURE:
<221> NAME/KEY: CDS
<222> LOCATION: (45)..(752)

<400> SEQUENCE: 76
taatacgact cactataggg agacccaagc tggctagcgc cacc atg gtg ttg cag       56
                                                Met Val Leu Gln
                                                1 acc cag gtc ttc att tct ctg ttg ctc tgg atc tct ggt gcc tac ggg      104
Thr Gln Val Phe Ile Ser Leu Leu Leu Trp Ile Ser Gly Ala Tyr Gly
5                  10                  15                  20 gat atc gtg ctg acc cag agc ccg gcg acc ctg agc ctg tct ccg ggc      152
Asp Ile Val Leu Thr Gln Ser Pro Ala Thr Leu Ser Leu Ser Pro Gly
                25                  30                  35 gaa cgt gcg acc ctg agc tgc aga gcg agc cag tct gtt tct ttt gat      200
Glu Arg Ala Thr Leu Ser Cys Arg Ala Ser Gln Ser Val Ser Phe Asp
            40                  45                  50 tat ctg ggt tgg tac cag cag aaa cca ggt caa gca ccg cgt cta tta      248
Tyr Leu Gly Trp Tyr Gln Gln Lys Pro Gly Gln Ala Pro Arg Leu Leu
        55                  60                  65 att tat ggt gct tct aat cgt gca act ggg gtc ccg gcg cgt ttt agc      296
Ile Tyr Gly Ala Ser Asn Arg Ala Thr Gly Val Pro Ala Arg Phe Ser
    70                  75                  80 ggc tct gga tcc ggc acg gat ttt acc ctg acc att agc agc ctg gaa      344
Gly Ser Gly Ser Gly Thr Asp Phe Thr Leu Thr Ile Ser Ser Leu Glu
85                  90                  95                  100 cct gaa gac ttt gcg acc tat tat tgc ctt cag tat ttt aat cct cct      392
Pro Glu Asp Phe Ala Thr Tyr Tyr Cys Leu Gln Tyr Phe Asn Pro Pro
                105                 110                 115 cat acc ttt ggc cag ggt acg aaa gtt gaa att aaa cgt acg gtg gct      440
His Thr Phe Gly Gln Gly Thr Lys Val Glu Ile Lys Arg Thr Val Ala
            120                 125                 130 gca cca tct gtc ttc atc ttc ccg cca tct gat gag cag ttg aaa tct      488
Ala Pro Ser Val Phe Ile Phe Pro Pro Ser Asp Glu Gln Leu Lys Ser
        135                 140                 145 gga act gcc tct gtt gtg tgc ctg ctg aat aac ttc tat ccc aga gag      536
Gly Thr Ala Ser Val Val Cys Leu Leu Asn Asn Phe Tyr Pro Arg Glu
    150                 155                 160 gcc aaa gta cag tgg aag gtg gat aac gcc ctc caa tcg ggt aac tcc      584
Ala Lys Val Gln Trp Lys Val Asp Asn Ala Leu Gln Ser Gly Asn Ser
165                 170                 175                 180 cag gag agt gtc aca gag cag gac agc aag gac agc acc tac agc ctc      632
Gln Glu Ser Val Thr Glu Gln Asp Ser Lys Asp Ser Thr Tyr Ser Leu
                185                 190                 195 agc agc acc ctg acg ctg agc aaa gca gac tac gag aaa cac aaa gtc      680
Ser Ser Thr Leu Thr Leu Ser Lys Ala Asp Tyr Glu Lys His Lys Val
```

```
                         200                 205                 210
tac gcc tgc gaa gtc acc cat cag ggc ctg agc tcg ccc gtc aca aag      728
Tyr Ala Cys Glu Val Thr His Gln Gly Leu Ser Ser Pro Val Thr Lys
        215                 220                 225 agc ttc aac agg gga gag tgt tag gggcccgttt aaacgggtgg catccctgtg      782
Ser Phe Asn Arg Gly Glu Cys
        230             235 acccctcccc agtgcctctc ctggccctgg aagttgccac tccagtgccc accagccttg    842
tcct                                                                  846
```

<210> SEQ ID NO 77
<211> LENGTH: 235
<212> TYPE: PRT
<213> ORGANISM: Artificial Sequence
<220> FEATURE:
<223> OTHER INFORMATION: Synthetic Construct

<400> SEQUENCE: 77

```
Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Phe Asp Tyr Leu Gly Trp Tyr Gln Gln Lys Pro Gly Gln Ala
    50                  55                  60

Pro Arg Leu Leu Ile Tyr Gly Ala Ser Asn Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Thr Tyr Tyr Cys Leu Gln Tyr
            100                 105                 110

Phe Asn Pro Pro His Thr Phe Gly Gln Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 78
<211> LENGTH: 846
<212> TYPE: DNA
<213> ORGANISM: Artificial Sequence
<220> FEATURE:
<223> OTHER INFORMATION: MOR07926 kappa light chain
<220> FEATURE:
<221> NAME/KEY: CDS
<222> LOCATION: (45)..(752)

<400> SEQUENCE: 78

```
taatacgact cactataggg agacccaagc tggctagcgc cacc atg gtg ttg cag        56
                                                Met Val Leu Gln
                                                1
acc cag gtc ttc att tct ctg ttg ctc tgg atc tct ggt gcc tac ggg        104
Thr Gln Val Phe Ile Ser Leu Leu Leu Trp Ile Ser Gly Ala Tyr Gly
5                   10                  15                  20
gat atc gtg ctg acc cag agc ccg gcg acc ctg agc ctg tct ccg ggc        152
Asp Ile Val Leu Thr Gln Ser Pro Ala Thr Leu Ser Leu Ser Pro Gly
                25                  30                  35
gaa cgt gcg acc ctg agc tgc aga gcg agc cag tct gtt tct ttt gat        200
Glu Arg Ala Thr Leu Ser Cys Arg Ala Ser Gln Ser Val Ser Phe Asp
            40                  45                  50
tat ctg ggt tgg tac cag cag aaa cca ggt caa gca ccg cgt cta tta        248
Tyr Leu Gly Trp Tyr Gln Gln Lys Pro Gly Gln Ala Pro Arg Leu Leu
        55                  60                  65
att tat ggt gct tct aat cgt gca act ggg gtc ccg gcg cgt ttt agc        296
Ile Tyr Gly Ala Ser Asn Arg Ala Thr Gly Val Pro Ala Arg Phe Ser
    70                  75                  80
ggc tct gga tcc ggc acg gat ttt acc ctg acc att agc agc ctg gaa        344
Gly Ser Gly Ser Gly Thr Asp Phe Thr Leu Thr Ile Ser Ser Leu Glu
85                  90                  95                  100
cct gaa gac ttt gcg acc tat tat tgc ttt cag gct ctt att atg cct        392
Pro Glu Asp Phe Ala Thr Tyr Tyr Cys Phe Gln Ala Leu Ile Met Pro
                105                 110                 115
ttt acc ttt ggc cag ggt acg aaa gtt gaa att aaa cgt acg gtg gct        440
Phe Thr Phe Gly Gln Gly Thr Lys Val Glu Ile Lys Arg Thr Val Ala
            120                 125                 130
gca cca tct gtc ttc atc ttc ccg cca tct gat gag cag ttg aaa tct        488
Ala Pro Ser Val Phe Ile Phe Pro Pro Ser Asp Glu Gln Leu Lys Ser
        135                 140                 145
gga act gcc tct gtt gtg tgc ctg ctg aat aac ttc tat ccc aga gag        536
Gly Thr Ala Ser Val Val Cys Leu Leu Asn Asn Phe Tyr Pro Arg Glu
    150                 155                 160
gcc aaa gta cag tgg aag gtg gat aac gcc ctc caa tcg ggt aac tcc        584
Ala Lys Val Gln Trp Lys Val Asp Asn Ala Leu Gln Ser Gly Asn Ser
165                 170                 175                 180
cag gag agt gtc aca gag cag gac agc aag gac agc acc tac agc ctc        632
Gln Glu Ser Val Thr Glu Gln Asp Ser Lys Asp Ser Thr Tyr Ser Leu
                185                 190                 195
agc agc acc ctg acg ctg agc aaa gca gac tac gag aaa cac aaa gtc        680
Ser Ser Thr Leu Thr Leu Ser Lys Ala Asp Tyr Glu Lys His Lys Val
            200                 205                 210
tac gcc tgc gaa gtc acc cat cag ggc ctg agc tcg ccc gtc aca aag        728
Tyr Ala Cys Glu Val Thr His Gln Gly Leu Ser Ser Pro Val Thr Lys
        215                 220                 225
agc ttc aac agg gga gag tgt tag gggcccgttt aaacgggtgg catccctgtg       782
Ser Phe Asn Arg Gly Glu Cys
        230                 235 acccctcccc agtgcctctc ctggccctgg aagttgccac tccagtgccc accagccttg      842
tcct                                                                    846
```

<210> SEQ ID NO 79
<211> LENGTH: 235
<212> TYPE: PRT
<213> ORGANISM: Artificial Sequence
<220> FEATURE:
<223> OTHER INFORMATION: Synthetic Construct

```
<400> SEQUENCE: 79

Met Val Leu Gln Thr Gln Val Phe Ile Ser Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Phe Asp Tyr Leu Gly Trp Tyr Gln Gln Lys Pro Gly Gln Ala
    50                  55                  60

Pro Arg Leu Leu Ile Tyr Gly Ala Ser Asn Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Thr Tyr Tyr Cys Phe Gln Ala
            100                 105                 110

Leu Ile Met Pro Phe Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 80
<211> LENGTH: 127
<212> TYPE: PRT
<213> ORGANISM: Artificial Sequence
<220> FEATURE:
<223> OTHER INFORMATION: Variable heavy chain 3
<220> FEATURE:
<221> NAME/KEY: misc_feature
<222> LOCATION: (30)..(35)
<223> OTHER INFORMATION: Xaa can be any naturally occurring amino acid
<220> FEATURE:
<221> NAME/KEY: misc_feature
<222> LOCATION: (50)..(66)
<223> OTHER INFORMATION: Xaa can be any naturally occurring amino acid
<220> FEATURE:
<221> NAME/KEY: misc_feature
<222> LOCATION: (99)..(116)
<223> OTHER INFORMATION: Xaa can be any naturally occurring amino acid

<400> SEQUENCE: 80

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
            20                  25                  30

Xaa Xaa Xaa Trp Val Arg Gln Ala Pro Gly Lys Gly Leu Glu Trp Val
        35                  40                  45

Ser Xaa Xaa Xaa Xaa Xaa Xaa Xaa Xaa Xaa Xaa Xaa Xaa Xaa Xaa Xaa
```

```
                 50                  55                  60
Xaa Xaa Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Xaa Xaa Xaa Xaa Xaa Xaa Xaa Xaa Xaa Xaa Xaa Xaa Xaa Xaa
            100                 105                 110

Xaa Xaa Xaa Xaa Trp Gly Gln Gly Thr Leu Val Thr Val Ser Ser
        115                 120                 125

<210> SEQ ID NO 81
<211> LENGTH: 127
<212> TYPE: PRT
<213> ORGANISM: Artificial Sequence
<220> FEATURE:
<223> OTHER INFORMATION: Variable heavy chain 5
<220> FEATURE:
<221> NAME/KEY: misc_feature
<222> LOCATION: (30)..(35)
<223> OTHER INFORMATION: Xaa can be any naturally occurring amino acid
<220> FEATURE:
<221> NAME/KEY: misc_feature
<222> LOCATION: (50)..(66)
<223> OTHER INFORMATION: Xaa can be any naturally occurring amino acid
<220> FEATURE:
<221> NAME/KEY: misc_feature
<222> LOCATION: (99)..(116)
<223> OTHER INFORMATION: Xaa can be any naturally occurring amino acid

<400> SEQUENCE: 81

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Xaa Xaa Xaa
                20                  25                  30

Xaa Xaa Xaa Trp Val Arg Gln Met Pro Gly Lys Gly Leu Glu Trp Met
         35                  40                  45

Gly Xaa Xaa Xaa Xaa Xaa Xaa Xaa Xaa Xaa Xaa Xaa Xaa Xaa Xaa Xaa
     50                  55                  60

Xaa Xaa Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Xaa Xaa Xaa Xaa Xaa Xaa Xaa Xaa Xaa Xaa Xaa Xaa Xaa Xaa
            100                 105                 110

Xaa Xaa Xaa Xaa Trp Gly Gln Gly Thr Leu Val Thr Val Ser Ser
        115                 120                 125

<210> SEQ ID NO 82
<211> LENGTH: 110
<212> TYPE: PRT
<213> ORGANISM: Artificial Sequence
<220> FEATURE:
<223> OTHER INFORMATION: Variable light chain keppa 3
<220> FEATURE:
<221> NAME/KEY: misc_feature
<222> LOCATION: (24)..(35)
<223> OTHER INFORMATION: Xaa can be any naturally occurring amino acid
<220> FEATURE:
<221> NAME/KEY: misc_feature
<222> LOCATION: (50)..(57)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be Thr or Val
```

```
<220> FEATURE:
<221> NAME/KEY: misc_feature
<222> LOCATION: (90)..(98)
<223> OTHER INFORMATION: Xaa can be any naturally occurring amino acid

<400> SEQUENCE: 82

Asp Ile Val Leu Thr Gln Ser Pro Ala Thr Leu Ser Leu Ser Pro Gly
1               5                   10                  15

Glu Arg Ala Thr Leu Ser Cys Xaa Xaa Xaa Xaa Xaa Xaa Xaa Xaa Xaa
            20                  25                  30

Xaa Xaa Xaa Trp Tyr Gln Gln Lys Pro Gly Gln Ala Pro Arg Leu Leu
        35                  40                  45

Ile Xaa Xaa Xaa Xaa Xaa Xaa Xaa Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Xaa Tyr Tyr Cys Xaa Xaa Xaa Xaa Xaa Xaa
                85                  90                  95

Xaa Xaa Phe Gly Gln Gly Thr Lys Val Glu Ile Lys Arg Thr
            100                 105                 110

<210> SEQ ID NO 83
<211> LENGTH: 110
<212> TYPE: PRT
<213> ORGANISM: Artificial Sequence
<220> FEATURE:
<223> OTHER INFORMATION: Variable light chain lambda
<220> FEATURE:
<221> NAME/KEY: misc_feature
<222> LOCATION: (23)..(33)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (48)..(55)
<223> OTHER INFORMATION: Xaa can be any naturally occurring amino acid
<220> FEATURE:
<221> NAME/KEY: misc_feature
<222> LOCATION: (88)..(98)
<223> OTHER INFORMATION: Xaa can be any naturally occurring amino acid

<400> SEQUENCE: 83

Asp Ile Glu Leu Thr Gln Pro Pro Ser Val Ser Val Ala Pro Gly Gln
1               5                   10                  15

Thr Ala Arg Ile Ser Cys Xaa Xaa Xaa Xaa Xaa Xaa Xaa Xaa Xaa Xaa
            20                  25                  30

Xaa Trp Tyr Gln Gln Lys Pro Gly Gln Ala Pro Val Xaa Val Ile Xaa
        35                  40                  45

Xaa Xaa Xaa Xaa Xaa Xaa Xaa Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Xaa Xaa Xaa Xaa Xaa Xaa Xaa Xaa
                85                  90                  95

Xaa Xaa Phe Gly Gly Gly Thr Lys Leu Thr Val Leu Gly Gln
            100                 105                 110
```

ANTI-MST1R ANTIBODIES AND USES THEREOF

This application is a continuation of International Application No. PCT/JP2010/052479, filed on Feb. 10, 2010, entitled "ANTI-MST1R ANTIBODIES AND USES THEREOF", which claims the benefit of U.S. Provisional Patent Application No. 61/151,411, filed on Feb. 10, 2009, all of which are hereby incorporated by reference.

BACKGROUND OF THE INVENTION

MST1R (macrophage stimulating 1 receptor; human MST1R is shown in GenBank® accession No; NM_002447.2), also described as RON or CDw136, is a c-Met related tyrosine kinase found on cells of epithelial origin. The 1400 amino acid single chain precursor is cleaved into a disulfide-linked heterodimer consisting of an extracellular 40kDa α-chain and a 150kDa β-chain, which includes the intracellular tyrosine kinase domain. Similar to c-Met, MST1R induces invasive cell growth, migration, cell dissociation and matrix invasion. [Wang, et al., *Carcinogenesis* 24, 1291-1300, 2003; Lee, et al., *Clin Cancer Res* 11, 2222-2228, 2005]. Both tyrosine kinases are overexpressed on a variety of malignant tumors, such as breast, lung or prostate cancer [O'Toole, et al., *Cancer Res* 66, 9162-9170, 2006]. MSP, macrophage stimulatory protein, is the only ligand to MST1R known so far. MSP binding triggers autophosphorylation of the MST1R tyrosine kinase domain. Thereby activated MST1R transduces a variety of different pathway cascades. [Wang, et al., *Carcinogenesis* 24, 1291-1300, 2003; O'Toole, et al., *Cancer Res* 66, 9162-9170, 2006]. Generation of biologically active, truncated MST1 R variants through mRNA splicing has also been reported [Wang, et al., *Carcinogenesis* 24, 1291-1300, 2003]. For example, MST1R$_\Delta$160 variant was found in some of colorectal carcinoma samples, and its overexpression without ligand mediated tumor formation in nude mice [Zhou et al., *Oncogene* 22, 186-197, 2003]. Anti-MST1R antibodies like IMC-41A10 block the ligand-receptor interaction and are potent inhibitors of receptor and downstream signaling, cell migration and tumorigenesis [O'Toole, et al., *Cancer Res* 66, 9162-9170, 2006].

In conclusion, antibodies blocking MST1R activity are of potential therapeutic relevance in human cancer.

SUMMARY OF INVENTION

It is an object to provide human and humanized antibodies against MST1R.

It is another object to provide antibodies that are safe for human administration.

It is also an object to provide methods for treating disease or and/or conditions associated with MST1R up-regulation by using one or more antibodies of the invention. These and other objects are more fully described herein.

In one embodiment, an isolated antibody or functional fragment that contains an antigen-binding region is specific for MST1R.

Such an antibody or functional fragment thereof may contain an antigen-binding region that contains an H-CDR3 (heavy chain CDR3) region having the amino acid sequence of SEQ ID NO: 1 or 4; the antigen-binding region may further include an H-CDR2 (heavy chain CDR2) region having the amino acid sequence of SEQ ID NO: 2 or 5; and the antigen-binding region also may contain an H-CDR1 (heavy chain CDR1) region having the amino acid sequence of SEQ ID NO: 3 or 6. Such an antibody or functional fragment thereof may contain an antigen-binding region that contains an L-CDR3 (light chain CDR3) region having the amino acid sequence of SEQ ID NO: 7, 8, 9, 10, 11 or 12; the antigen-binding region may further include an L-CDR1 (light chain CDR1) region having the amino acid sequence of SEQ ID NO: 13 or 15; and the antigen-binding region also may contain an L-CDR2 (light chain CDR2) region having the amino acid sequence of SEQ ID NO: 14 or 16.

Antibodies (and functional fragments thereof) described herein may contain an antigen-binding region that is specific for an epitope of MST1R, which epitope contains one or more amino acid residues of amino acid having the amino acid sequence of SEQ ID NO: 17. For certain antibodies, the epitope may be linear, whereas for others, it may be conformational (i.e., discontinuous). An antibody or functional fragment thereof having one or more of these properties may contain an antigen-binding region that contains an H-CDR3 region having the amino acid sequence of SEQ ID NO: 1 or 4; the antigen-binding region may further include an H-CDR2 region having the amino acid sequence of SEQ ID NO: 2 or 5; and the antigen-binding region also may contain an H-CDR1 region having the amino acid sequence of SEQ ID NO: 3 or 6. Such a MST1R-specific antibody of the invention may contain an antigen-binding region that contains an L-CDR3 region having the amino acid sequence of SEQ ID NO: 7, 8, 9, 10, 11 or 12; the antigen-binding region may further include an L-CDR1 region shown in SEQ ID NO: 13 or 15; and the antigen-binding region also may contain an L-CDR2 region having the amino acid sequence of SEQ ID NO: 14 or 16.

Peptide variants of the sequences disclosed herein are also embraced by various embodiments of the disclosure. Accordingly, the embodiments include anti-MST1R antibodies having a heavy chain amino acid sequence with: at least 60 percent sequence identity in the CDR regions with the CDR regions having the amino acid sequence of SEQ ID NO: 1, 2, 3, 4, 5 or 6; and/or at least 80 percent sequence homology in the CDR regions with the CDR regions having the amino acid sequence of SEQ ID NO: 1, 2, 3, 4, 5 or 6. Further included are anti-MST1R antibodies having a light chain amino acid sequence with: at least 60 percent sequence identity in the CDR regions with the CDR regions having the amino acid sequence of SEQ ID NO: 7, 8, 9, 10, 11, 12, 13, 14, or 16; and/or at least 80 percent sequence homology in the CDR regions with the CDR regions having the amino acid sequence of SEQ ID NO: 7, 8, 9, 10, 11, 12, 13, 14, 15 or 16.

An antibody disclosed herein may be an IgG (e.g., IgG$_1$), while an antibody fragment may be a Fab or scFv, for example. An inventive antibody fragment, accordingly, may be, or may contain, an antigen-binding region that behaves in one or more ways as described herein.

Another embodiment also relates to isolated nucleic acid sequences, each of which can encode an antigen-binding region of a human antibody or functional fragment thereof that is specific for an epitope of MST1R. Such a nucleic acid sequence may encode a variable heavy chain of an antibody and include a sequence selected from the group consisting of SEQ ID NOS: 18, 20 or a nucleic acid sequence that hybridizes under high stringency conditions to the complementary strand of SEQ ID NO: 18 or 20. The nucleic acid might encode a variable light chain of an isolated antibody or functional fragment thereof, and may contain a sequence selected from the group consisting of SEQ ID NOS: 22, 24, 26, 28, 30, 32, or a nucleic acid sequence that hybridizes under high stringency conditions to the complementary strand of SEQ ID NO: 22, 24, 26, 28, 30 or 32.

Nucleic acids described herein are suitable for recombinant production. Thus, vectors and host cells containing a nucleic acid sequence disclosed herein are also further embodiments.

Compositions described herein may be used for therapeutic or prophylactic applications. These embodiments, therefore, include a pharmaceutical composition containing an inventive antibody (or functional antibody fragment) and a pharmaceutically acceptable carrier or excipient thereof. In a related aspect, another embodiment includes methods for treating a disorder or condition associated with the undesired presence of MST1R or MST1R expressing cells. Such method contains the steps of administering to a subject in need thereof an effective amount of the pharmaceutical composition that contains an inventive antibody as described or contemplated herein.

Yet other embodiments relate to isolated epitopes of MST1R, either in linear or conformational form, and their use for the isolation of an antibody or functional fragment thereof, which antibody of antibody fragment comprises an antigen-binding region that is specific for said epitope. In this regard, a conformational epitope may contain one or more amino acid residues in SEQ ID NO: 17. An epitope of MST1R can be used, for example, for the isolation of antibodies or functional fragments thereof (each of which antibodies or antibody fragments comprises an antigen-binding region that is specific for such epitope), comprising the steps of contacting said epitope of MST1R with an antibody library and isolating the antibody(ies) or functional fragment(s) thereof.

In another embodiment, the disclosure provides an isolated epitope of MST1R, which consists essentially of an amino acid sequence in SEQ ID NO: 17. As used herein, such an epitope "consists essentially of" one of the immediately preceding amino acid sequences plus additional features, provided that the additional features do not materially affect the basic and novel characteristics of the epitope.

The disclosure is also directed to a kit having (i) an isolated epitope of MST1R comprising one or more amino acid residues of the amino acid sequence in SEQ ID NO: 17; (ii) an antibody library; and (iii) instructions for using the antibody library to isolate one or more members of such library that binds specifically to such epitope.

BRIEF DESCRIPTION OF DRAWINGS

FIG. 2.

FIG. 3: FIG. 3A (MOR07692, MOR07923, MOR07924, MOR07925, MOR07926; SEQ ID NO: 18) and FIG. 3B (MOR07919; SEQ ID NO: 20) provide nucleic acid sequences of various novel antibody variable heavy regions. FIG. 3C (MOR07692, MOR07923, MOR07924, MOR07925, MOR07926; SEQ ID NO: 19) and FIG. 3D (MOR07919; SEQ ID NO: 21) provide amino acid sequences of various novel antibody variable heavy regions. CDR regions H-CDR1, H-CDR2 and H-CDR3 are designated from N- to C-terminus in boldface and underlined.

FIG. 5 provides amino acid sequences of variable heavy regions of various consensus-based Human Combinatorial Antibody Library (HuCAL®) antibody master gene sequences. CDR regions H-CDR1, H-CDR2 and H-CDR3 are underlined as designated from N- to C-terminus. The upper line is MOR07919 (SEQ ID NO: 21) while the lower line is MOR07692/7923/7924/7925/7926 (SEQ ID NO: 19).

Figure 6:
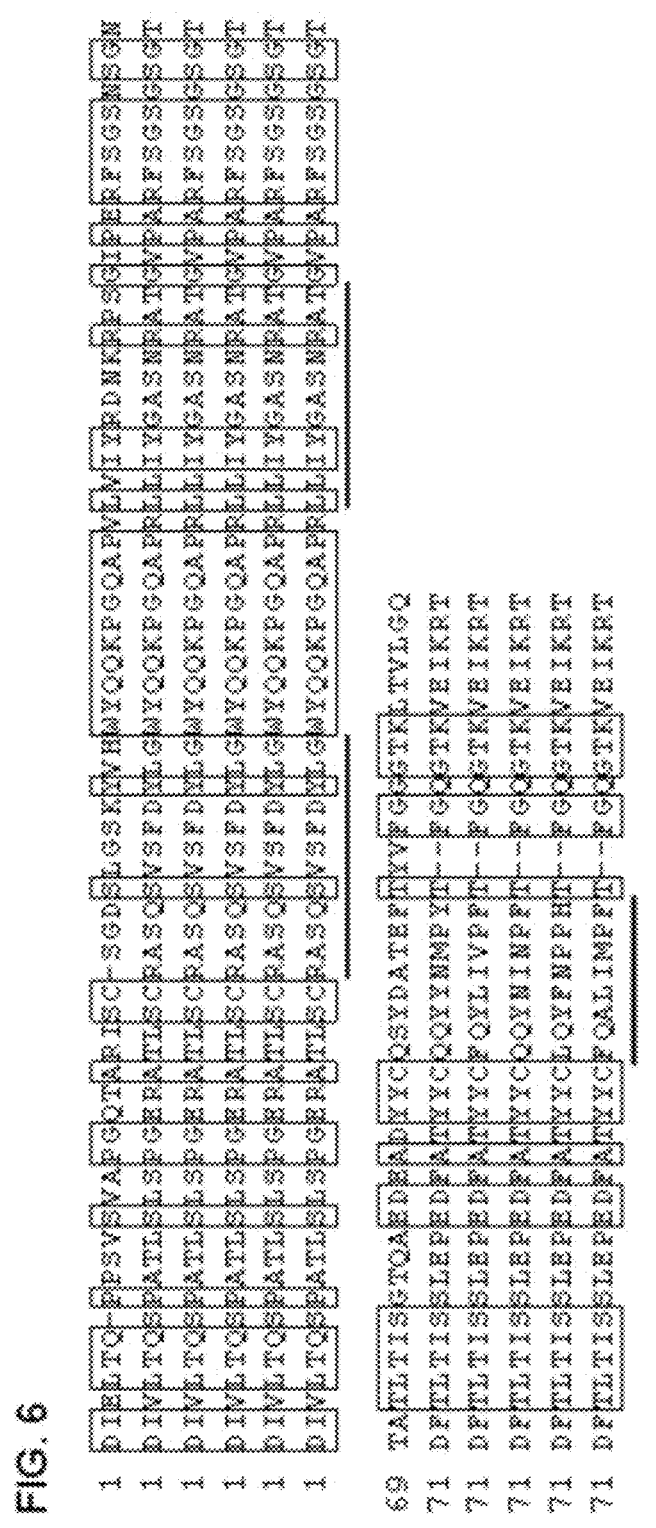

FIG. 6 provides amino acid sequences of variable light regions of various consensus-based HuCAL antibody master gene sequences. CDR regions L-CDR1, L-CDR2 and L-CDR3 are underlined as designated from N- to C-terminus. The two sets of lines from top to bottom are as follows: MOR07919 (SEQ ID NO: 25); MOR07692 (SEQ ID NO: 23); MOR07923 (SEQ ID NO: 27); MOR07924 (SEQ ID NO: 29); MOR07925 (SEQ ID NO: 31); MOR07926 (SEQ ID NO: 33), respectively.

Figure 7A:
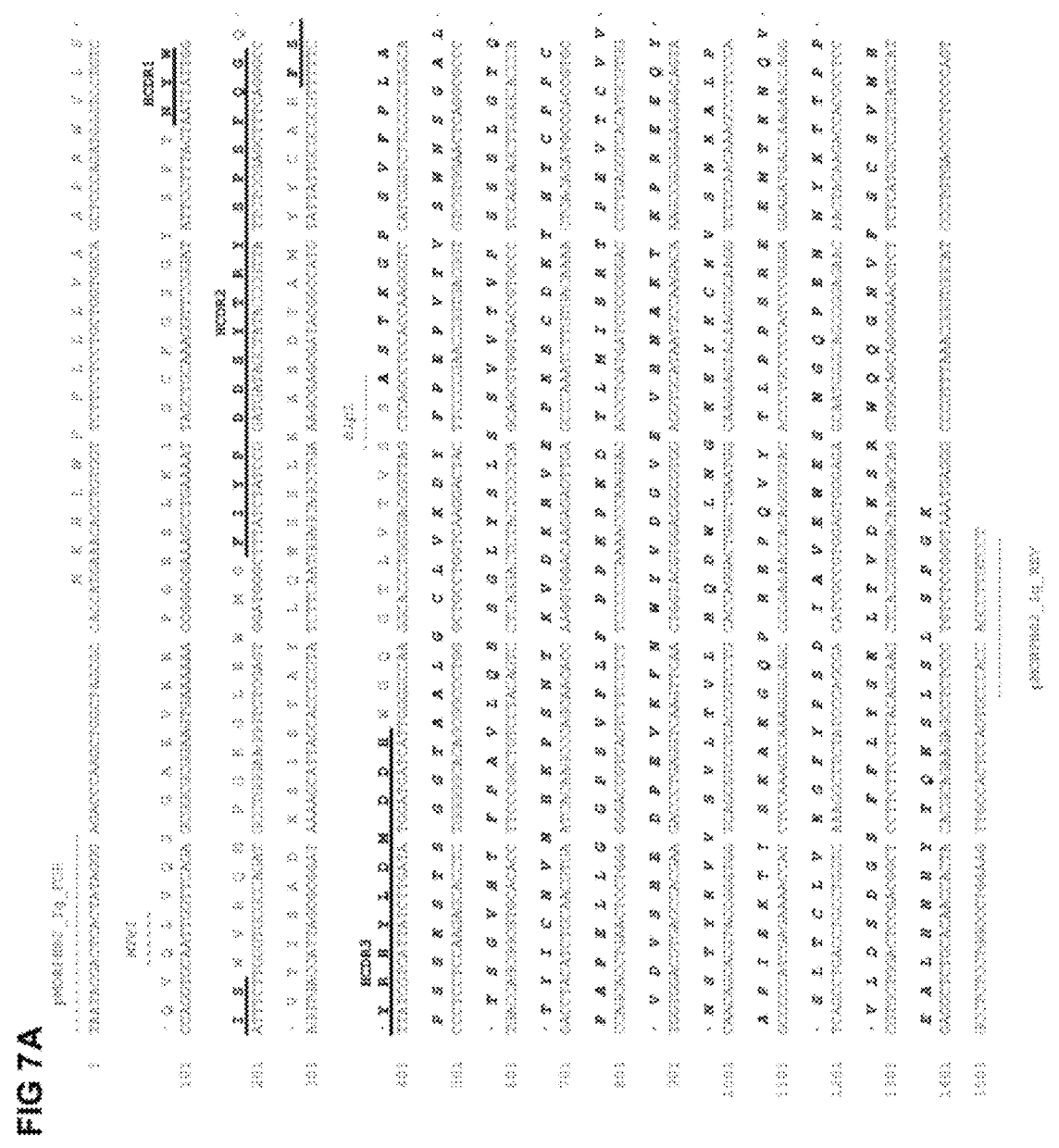
Figure 7B:
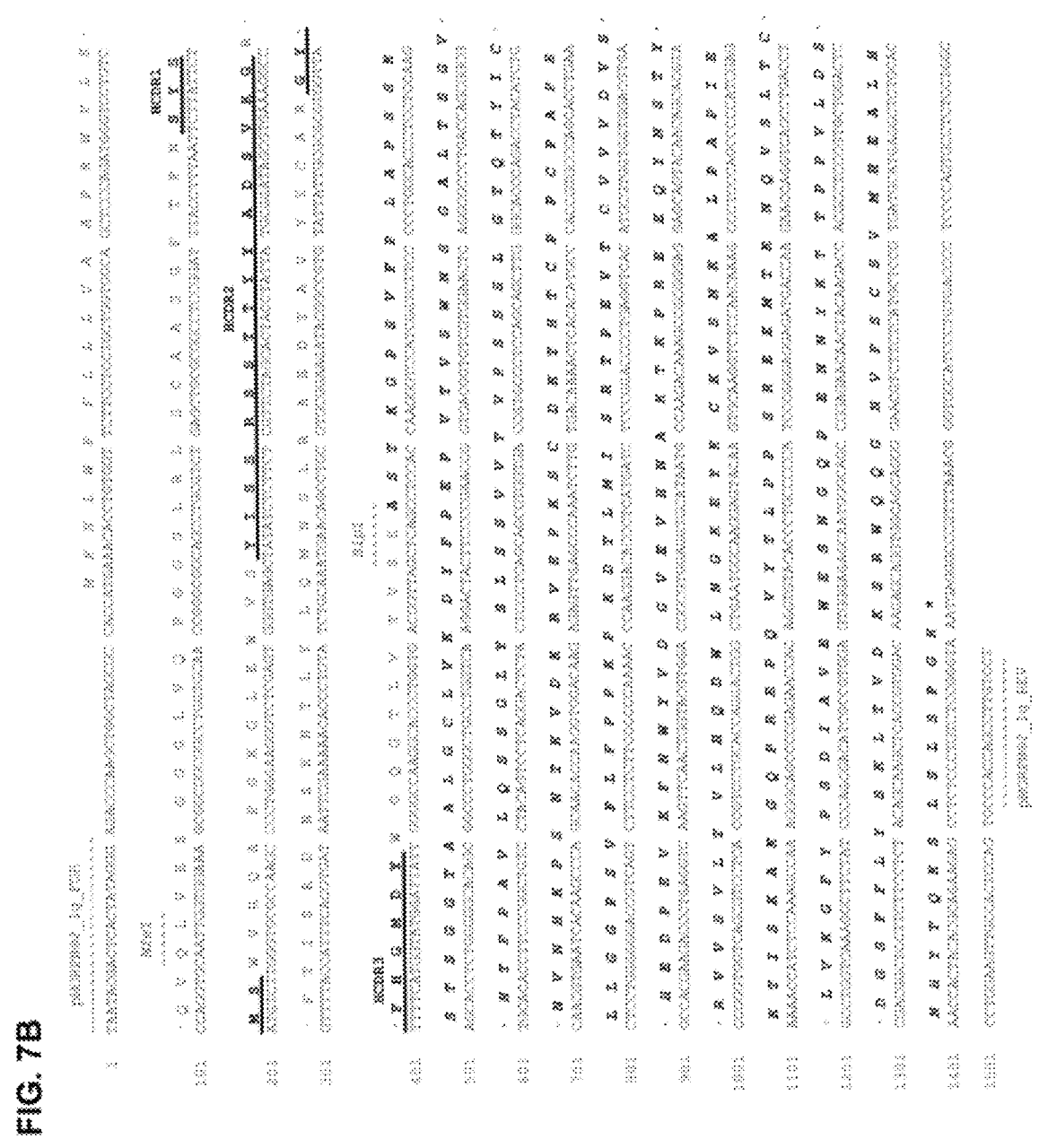

FIG. 7: FIG. 7A and FIG. 7B provide the nucleic acid and the amino acid sequence of various novel antibody heavy chains (FIG. 7A: MOR07919; FIG. 7B: MOR07692, MOR07923, MOR07924, MOR07925 and MOR07926; respectively) as expressed from pMORPH®2_h_IgG1f. CDR regions are in boldface and underlined. Amino acid sequence of VH leader and heavy chain constant region is indicated in italics or italics and boldface, respectively. Restriction sites and priming sites of sequencing primers are designated above or below the sequence. The nucleic acid sequence of FIG. 7A is represented by SEQ ID NO: 64, while the amino acid sequence is SEQ ID NO: 65. The nucleic acid sequence of FIG. 7B is represented by SEQ ID NO: 66, while the amino acid sequence is SEQ ID NO: 67.

Figure 8:
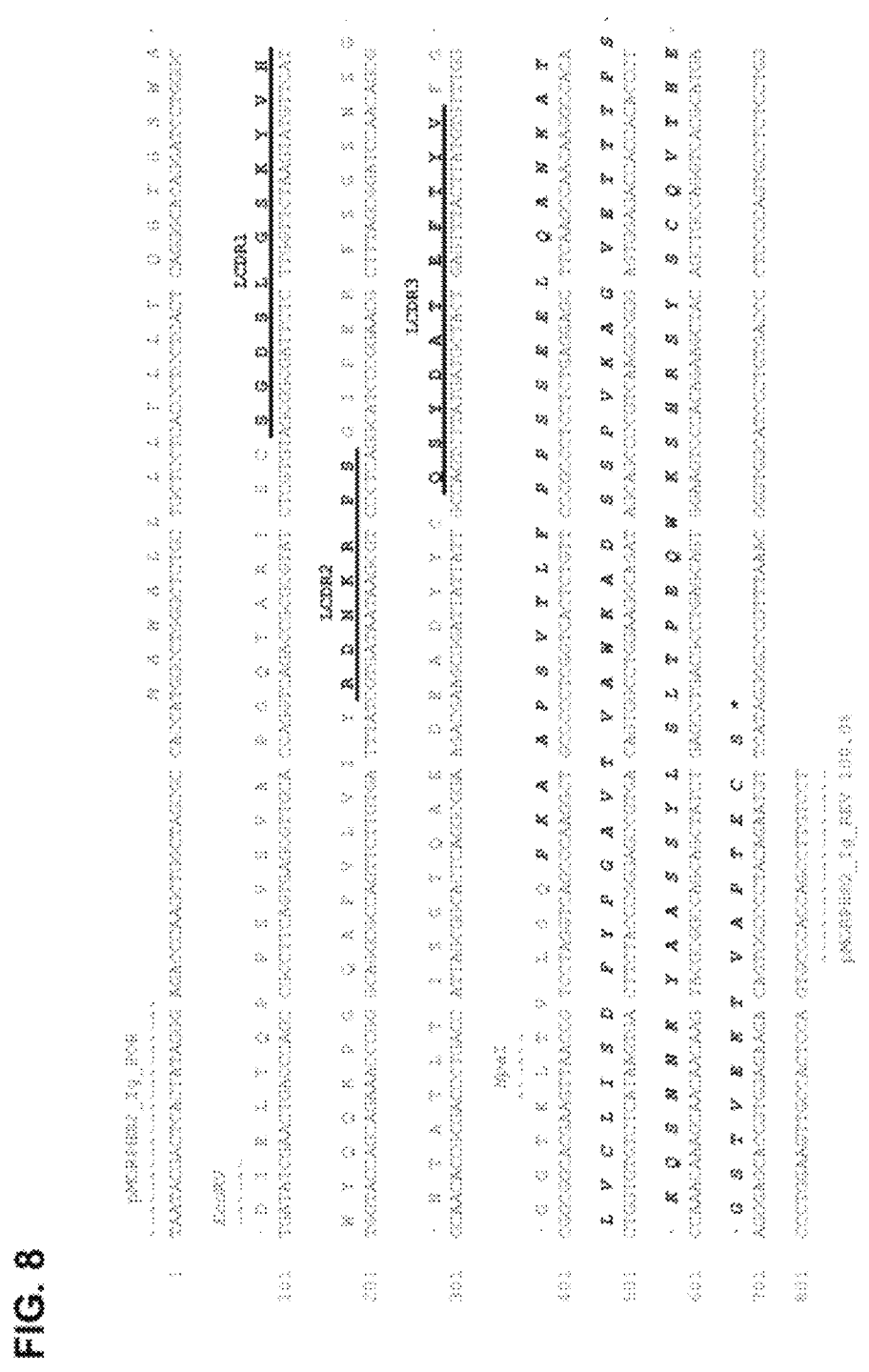

FIG. 8 provides the nucleic acid sequence (SEQ ID NO: 68) and the amino acid sequence (SEQ ID NO: 69) of a novel antibody lambda light chain (MOR07919) as expressed from pMORPH®2_h_Ig_lambda2. CDR regions are in boldface and underlined. Amino acid sequence of VL leader and lambda light chain constant region is indicated in italics or italics and boldface, respectively. Restriction sites and priming sites of sequencing primers are designated above or below the sequence.

Figure 9A:
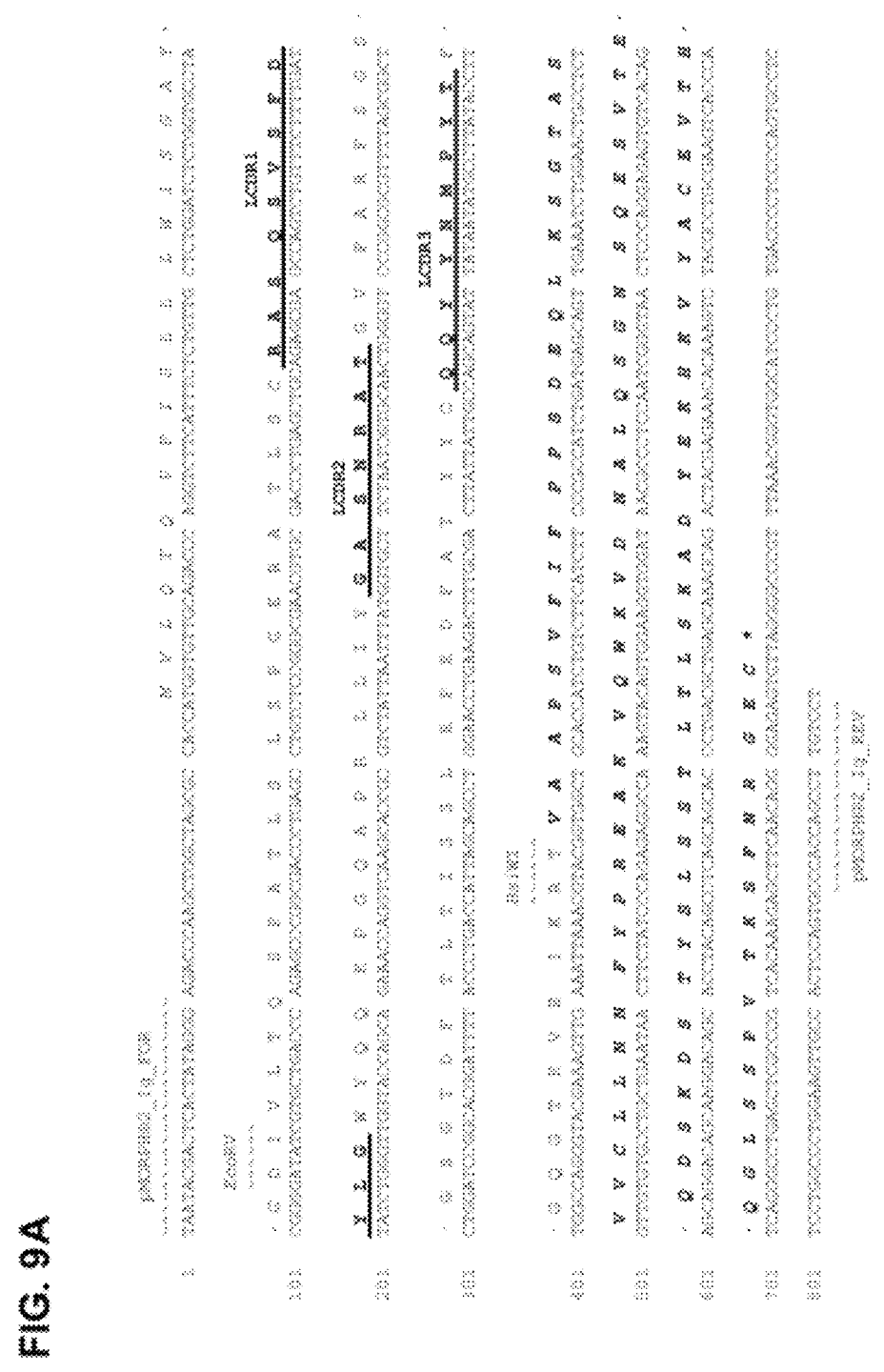
Figure 9B:
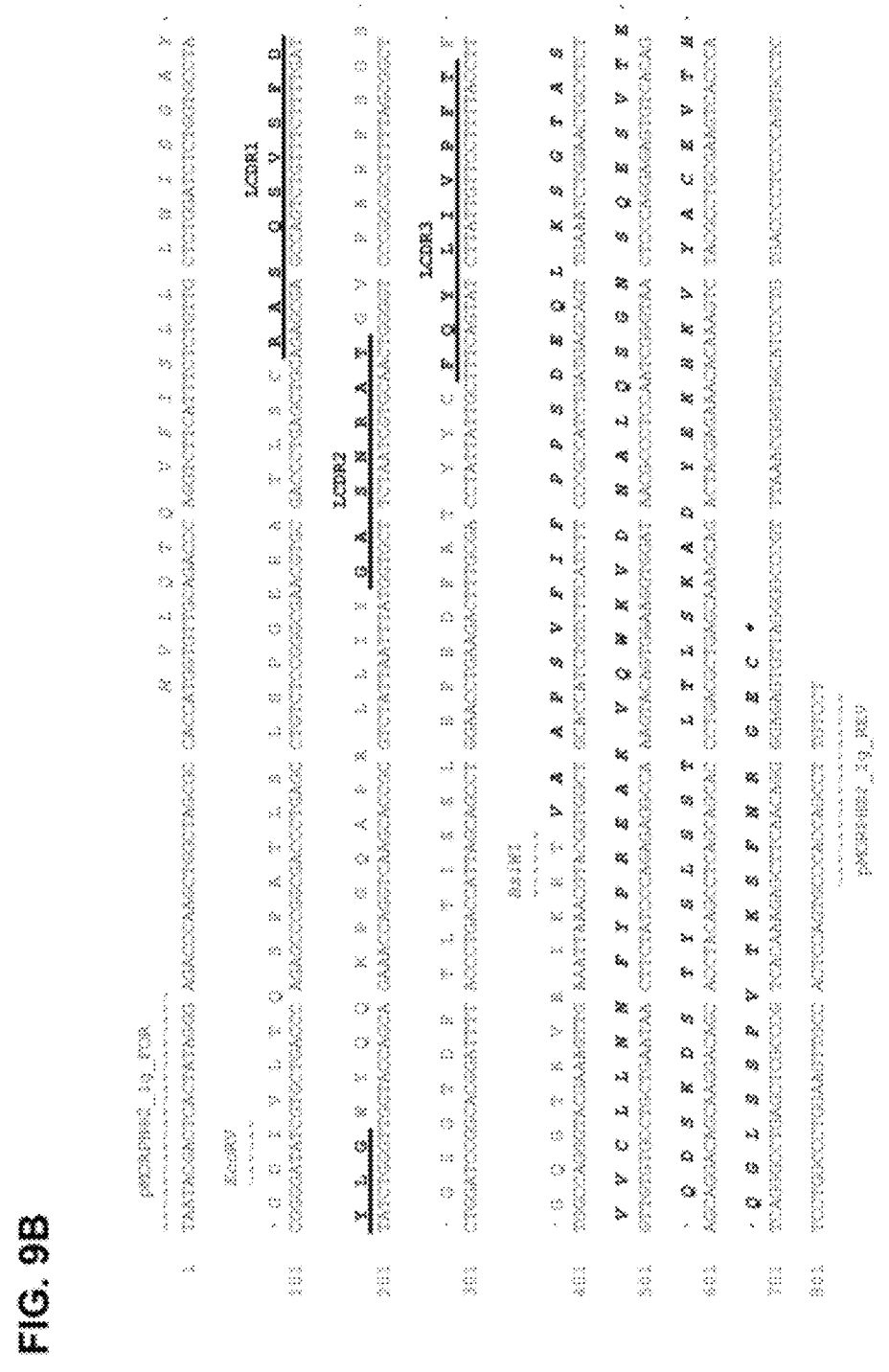
Figure 9C:
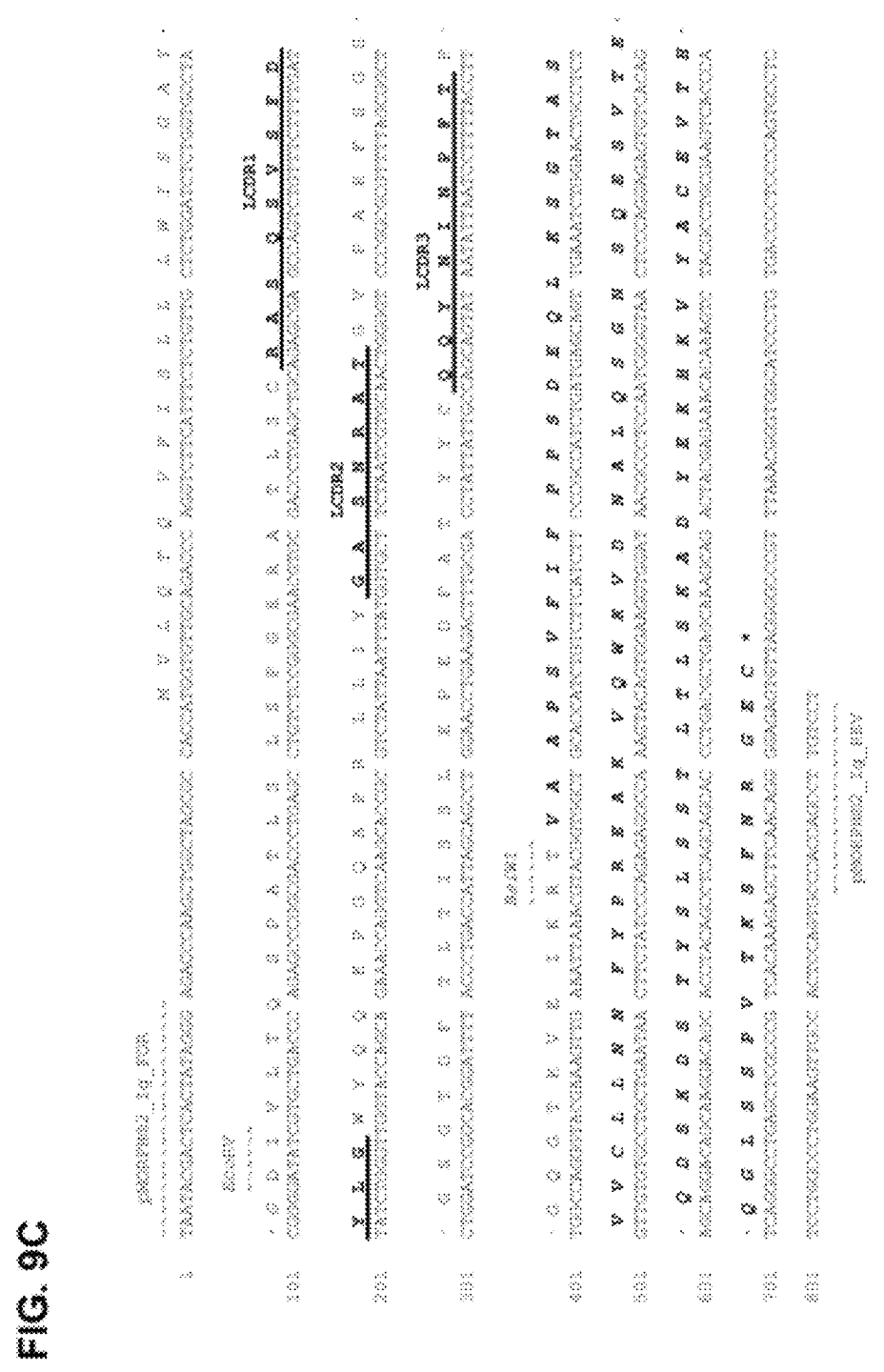
Figure 9D:
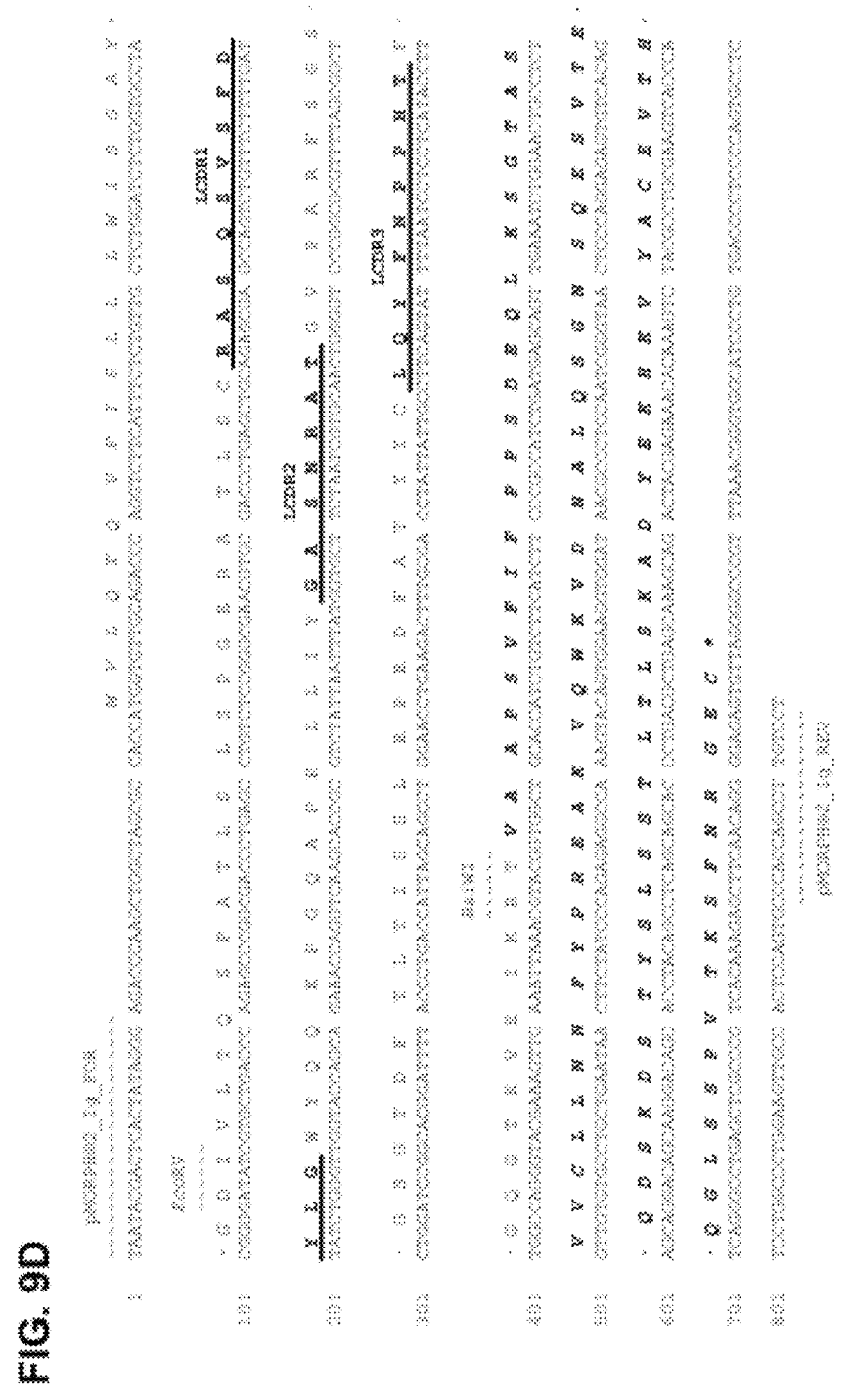
Figure 9E:
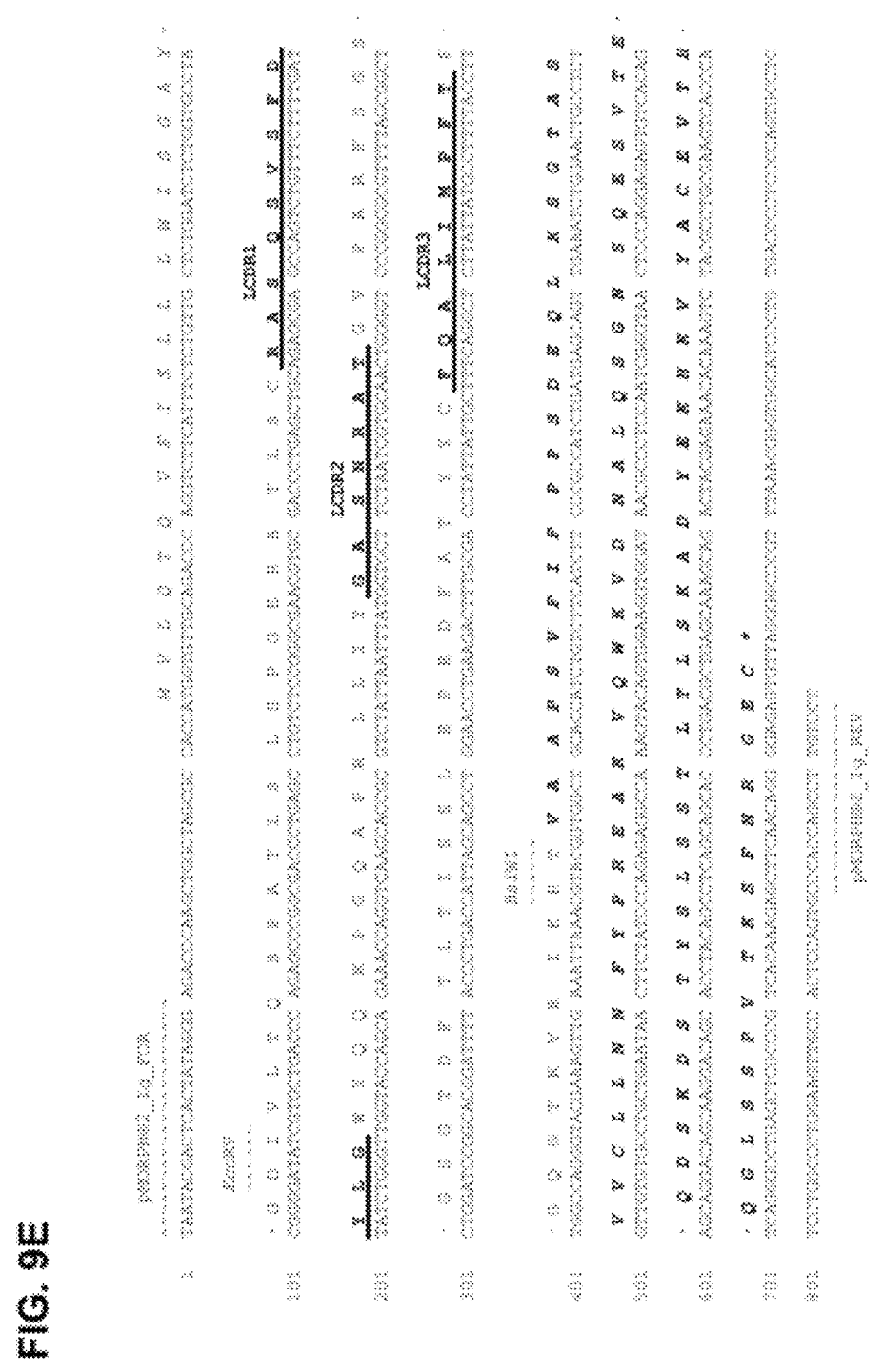

FIG. 9: FIG. 9A to FIG. 9E provide the nucleic acid and the amino acid sequence of various novel antibody kappa light chains as expressed from pMORPH®2_h_Ig kappa. CDR regions are in boldface and underlined. Amino acid sequence of VL leader and kappa light chain constant region is indicated in italics or italics and boldface, respectively. Restriction sites and priming sites of sequencing primers are designated above or below the sequence. The nucleic acid sequence of FIG. 9A is represented by SEQ ID NO: 70, while the amino acid sequence is SEQ ID NO: 71 (MOR07692). The nucleic acid sequence of FIG. 9B is represented by SEQ ID NO: 72, while the amino acid sequence is SEQ ID NO: 73 (MOR07923). The nucleic acid sequence of FIG. 9C is represented by SEQ ID NO: 74, while the amino acid sequence is SEQ ID NO: 75 (MOR07924). The nucleic acid sequence of FIG. 9D is represented by SEQ ID NO: 76, while the amino acid sequence is SEQ ID NO: 77 (MOR07925). The nucleic acid sequence of FIG. 9E is represented by SEQ ID NO: 78, while the amino acid sequence is SEQ ID NO: 79 (MOR07926).

DETAILED DESCRIPTION

Figure 1:
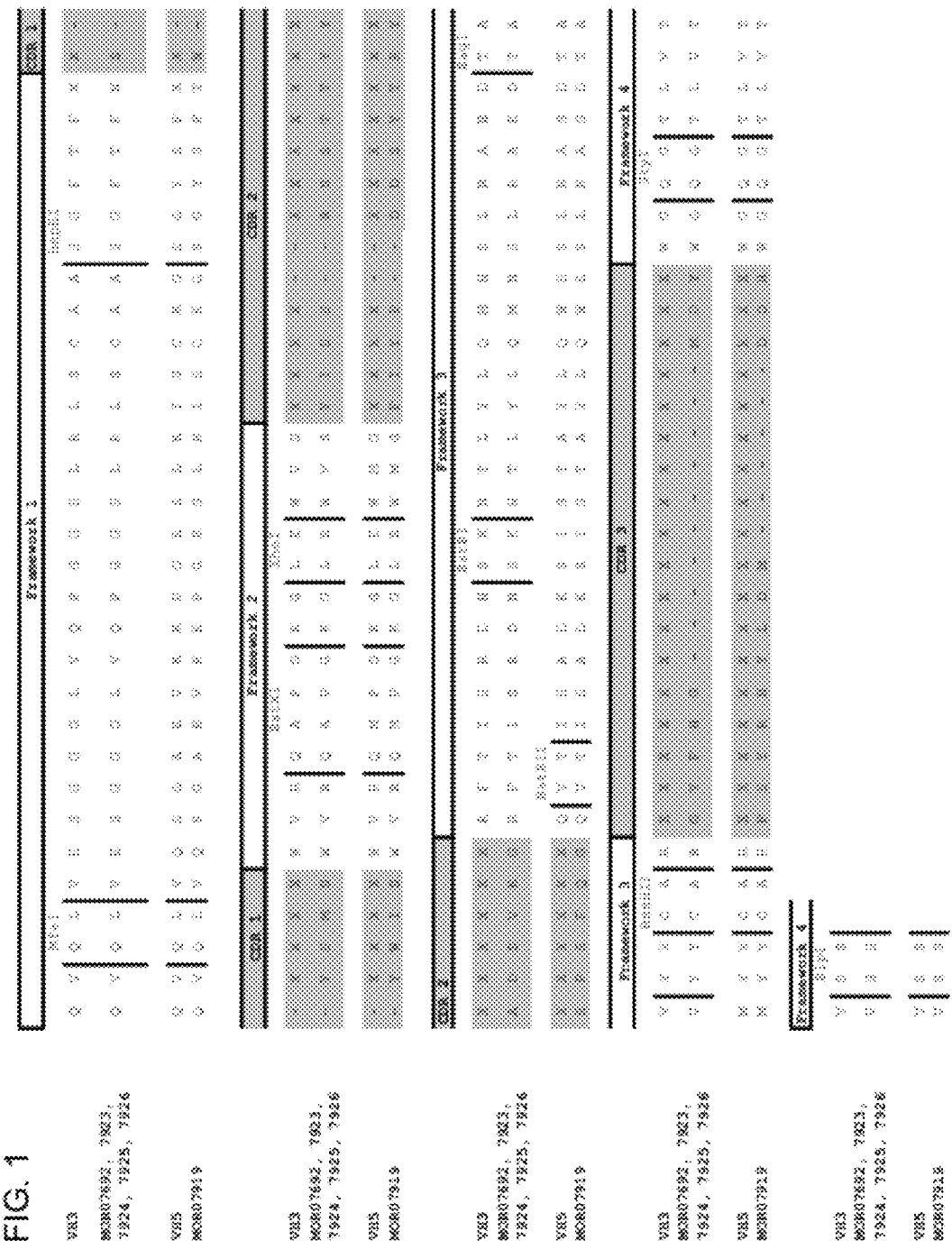
FIG. 1 provides amino acid sequences of various novel antibody variable heavy regions, and which delineates the CDR and framework (FR) regions. The VH3 sequence (SEQ ID NO: 80) is aligned with the MOR07692, MOR07923, MOR07924, MOR07925, MOR07926 variable heavy region sequence (SEQ ID NO: 19), and the VH5 sequence (SEQ ID NO: 81) is aligned with MOR07919 variable heavy region sequence (SEQ ID NO: 21).

The present disclosure is based on the discovery of novel antibodies that are specific to or have a high affinity for MST1R and can deliver a therapeutic benefit to a subject. The antibodies disclosed herein, which may be human or humanized, can be used in many contexts, which are more fully described herein.

A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment, is one that is encoded by a nucleic acid isolated from a library of antibody sequences of human origin (i.e., such library being based on antibodies taken from a human natural source).

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) complementarity determining regions (CDR)-grafted, wherein the CDRs of the variable domain are from a non-human origin, while one or more frameworks of the variable domain are of human origin and the constant domain (if any) is of human origin.

As used herein, an antibody "binds specifically to," is "specific to/for" or "specifically recognizes" an antigen (here, MST1R) if such antibody is able to discriminate between such antigen and one or more reference antigen(s), since binding specificity is not an absolute, but a relative property. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like.

However, "specific binding" also may refer to the ability of an antibody to discriminate between the target antigen and one or more closely related antigen(s), which are used as reference points, e.g. between target MST1R and target semaphorin. Additionally, "specific binding" may relate to the ability of an antibody to discriminate between different parts of its target antigen, e.g. different domains or regions of MST1R, such as epitopes in the N-terminal or in the C-terminal region of target MST1R, or between one or more key amino acid residues or stretches of amino acid residues of target MST1R.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. In various embodiments, the "antigen-binding region" comprises at least amino acid residues 4 to 103 of the variable light (VL) chain and 5 to 109 of the variable heavy (VH) chain, amino acid residues 3 to 107 of VL and 4 to 111 of VH, and are the complete VL and VH chains (amino acid positions 1 to 109 of VL and 1 to 113 of VH; numbering according to WO 97/08320). A exemplary class of immunoglobulins for use in the embodiments described herein is IgG. "Functional fragments" of the invention include the domain of a F(ab')$_2$ fragment, a Fab fragment and scFv. The F(ab')$_2$ or Fab may be engineered to minimize or completely remove the intermolecular disulphide interactions that occur between the CH1 and CL domains.

An antibody described herein may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., *J. Mol. Biol.* 296: 57-86, 2000; Krebs et al., *J. Immunol. Methods.* 254:67-84, 2001; and U.S. Pat. No. 6,300,064 issued to Knappik et al., which hereby are incorporated by reference in their entirety.
Antibodies Described Herein Throughout this disclosure, reference is made to the following representative antibodies: "antibody nos." or "LACS" or "MOR" X. MOR X represents an antibody having a variable heavy region corresponding to SEQ ID NO: 18 or 20 (DNA)/SEQ ID NO: 19 or 21 (protein) and a variable light region selected from the group consisting of SEQ ID NOs: 22, 24, 26, 28, 30 and 32 (DNA)/SEQ ID NOs: 23, 25, 27, 29, 31 and 33 (protein).

In one example, the disclosure provides an antibody having a variable heavy region corresponding to SEQ ID NO: 18 (DNA)/SEQ ID: NO: 19 (protein) and a variable light chain corresponding to SEQ ID NO: 22 (DNA)/SEQ ID NO: 23 (protein).

In one example, the disclosure provides an antibody having a variable heavy region corresponding to SEQ ID NO: 20 (DNA)/SEQ ID: NO: 21 (protein) and a variable light chain corresponding to SEQ ID NO: 24 (DNA)/SEQ ID NO: 25 (protein).

In one example, the disclosure provides an antibody having a variable heavy region corresponding to SEQ ID NO: 18 (DNA)/SEQ ID: NO: 19 (protein) and a variable light chain corresponding to SEQ ID NO: 26 (DNA)/SEQ ID NO: 27 (protein).

In one example, the disclosure provides an antibody having a variable heavy region corresponding to SEQ ID NO: 18 (DNA)/SEQ ID: NO: 19 (protein) and a variable light chain corresponding to SEQ ID NO: 28 (DNA)/SEQ ID NO: 29 (protein).

In one example, the disclosure provides an antibody having a variable heavy region corresponding to SEQ ID NO: 18 (DNA)/SEQ ID: NO: 19 (protein) and a variable light chain corresponding to SEQ ID NO: 30 (DNA)/SEQ ID NO: 31 (protein).

In one example, the disclosure provides an antibody having a variable heavy region corresponding to SEQ ID NO: 18 (DNA)/SEQ ID: NO: 19 (protein) and a variable light chain corresponding to SEQ ID NO: 32 (DNA)/SEQ ID NO: 33 (protein).

In another aspect, the disclosure provides following antibodies.

In one example, the disclosure provides an antibody containing an antigen-binding region that contains an H-CDR3 (heavy chain CDR3) region having the amino acid sequence of SEQ ID NO: 1 or 4; the antigen-binding region may further include an H-CDR2 (heavy chain CDR2) region having the amino acid sequence of SEQ ID NO: 2 or 5; and the antigen-binding region also may contain an H-CDR1 (heavy chain CDR1) region having the amino acid sequence of SEQ ID NO: 3 or 6. Such an antibody thereof may contain an antigen-binding region that contains an L-CDR3 (light chain CDR3) region having the amino acid sequence of SEQ ID NO: 7, 8, 9, 10, 11 or 12; the antigen-binding region may further include an L-CDR1 (light chain CDR1) region having the amino acid sequence of SEQ ID NO: 13 or 15; and the antigen-binding region also may contain an L-CDR2 (light chain CDR2) region having the amino acid sequence of SEQ ID NO: 14 or 16.

The disclosure also provides an antibody containing the antigen-binding region (i) H-CDR3 region having the amino acid sequence of SEQ ID NO: 1, H-CDR2 region having the amino acid sequence of SEQ ID NO: 2 and H-CDR1 region having the amino acid sequence of SEQ ID NO: 3, (ii) H-CDR3 region having the amino acid sequence of SEQ ID NO: 4, H-CDR2 region having the amino acid sequence of SEQ ID NO: 5 and H-CDR1 region having the amino acid sequence of SEQ ID NO: 6.

One embodiment also provides an antibody containing an antigen-binding region selected from the group consisting of (i) L-CDR3 region having the amino acid sequence of SEQ ID NO: 7, L-CDR1 region having the amino acid sequence of SEQ ID NO: 13 and L-CDR2 region having the amino acid sequence of SEQ ID NO: 14, (ii) L-CDR3 region having the amino acid sequence of SEQ ID NO: 8, L-CDR1 region having the amino acid sequence of SEQ ID NO: 15 and L-CDR2 region having the amino acid sequence of SEQ ID NO: 16, (iii) L-CDR3 region having the amino acid sequence of SEQ ID NO: 9, L-CDR1 region having the amino acid sequence of SEQ ID NO: 13 and L-CDR2 region having the amino acid sequence of SEQ ID NO: 14, (iv) L-CDR3 region having the amino acid sequence of SEQ ID NO: 10, L-CDR1 region having the amino acid sequence of SEQ ID NO: 13 and L-CDR2 region having the amino acid sequence of SEQ ID NO: 14, (v) L-CDR3 region having the amino acid sequence of SEQ ID NO: 11, L-CDR1 region having the amino acid sequence of SEQ ID NO: 13 and L-CDR2 region having the amino acid sequence of SEQ ID NO: 14, or (vi) L-CDR3 region having the amino acid sequence of SEQ ID NO: 12, L-CDR1 region having the amino acid sequence of SEQ ID NO: 13 and L-CDR2 region having the amino acid sequence of SEQ ID NO: 14.

Another embodiment provides an antibody containing an antigen-binding region selected from the group consisting of (i) H-CDR3 region having the amino acid sequence of SEQ ID NO: 1, H-CDR2 region having the amino acid sequence of SEQ ID NO: 2, H-CDR1 region having the amino acid sequence of SEQ ID NO: 3, L-CDR3 region having the amino acid sequence of SEQ ID NO: 7, L-CDR1 region having the amino acid sequence of SEQ ID NO: 13 and L-CDR2 region having the amino acid sequence of SEQ ID NO: 14, (ii) H-CDR3 region having the amino acid sequence of SEQ ID NO: 4, H-CDR2 region having the amino acid sequence of SEQ ID NO: 5, H-CDR1 region having the amino acid sequence of SEQ ID NO: 6, L-CDR3 region having the amino acid sequence of SEQ ID NO: 8, L-CDR1 region having the amino acid sequence of SEQ ID NO: 15 and L-CDR2 region having the amino acid sequence of SEQ ID NO: 16, (iii) H-CDR3 region having the amino acid sequence of SEQ ID NO: 1, H-CDR2 region having the amino acid sequence of SEQ ID NO: 2, H-CDR1 region having the amino acid sequence of SEQ ID NO: 3, L-CDR3 region having the amino acid sequence of SEQ ID NO: 9, L-CDR1 region having the amino acid sequence of SEQ ID NO: 13 and L-CDR2 region having the amino acid sequence of SEQ ID NO: 14, (iv) H-CDR3 region having the amino acid sequence of SEQ ID NO: 1, H-CDR2 region having the amino acid sequence of SEQ ID NO: 2, H-CDR1 region having the amino acid sequence of SEQ ID NO: 3, L-CDR3 region having the amino acid sequence of SEQ ID NO: 10, L-CDR1 region having the amino acid sequence of SEQ ID NO: 13 and L-CDR2 region having the amino acid sequence of SEQ ID NO: 14, (v) H-CDR3 region having the amino acid sequence of SEQ ID NO: 1, H-CDR2 region having the amino acid sequence of SEQ ID NO: 2, H-CDR1 region having the amino acid sequence of SEQ ID NO: 3, L-CDR3 region having the amino acid sequence of SEQ ID NO: 11, L-CDR1 region having the amino acid sequence of SEQ ID NO: 13 and L-CDR2 region having the amino acid sequence of SEQ ID NO: 14, and (vi) H-CDR3 region having the amino acid sequence of SEQ ID NO: 1, H-CDR2 region having the amino acid sequence of SEQ ID NO: 2, H-CDR1 region having the amino acid sequence of SEQ ID NO: 3, L-CDR3 region having the amino acid sequence of SEQ ID NO: 12, L-CDR1 region having the amino acid sequence of SEQ ID NO: 13 and L-CDR2 region having the amino acid sequence of SEQ ID NO: 14, In another aspect, the disclosure provides the following antibodies.

One embodiment also provides an antibody comprising (i) a heavy chain having an amino acid sequence of SEQ ID NO: 49 or 51; and (ii) a light chain having an amino acid sequence selected from the group of SEQ ID NOs: 53, 55, 57, 59, 61 and 63.

Yet another embodiment provides an antibody selected from the group of (i) a heavy chain having an amino acid sequence of SEQ ID NO: 49 and a light chain having an amino acid sequence of SEQ ID NO: 53 (named as "MOR07919"), (ii) a heavy chain having an amino acid sequence of SEQ ID NO: 51 and a light chain having an amino acid sequence of SEQ ID NO: 55 (named as "MOR07692"), (iii) a heavy chain having an amino acid sequence of SEQ ID NO: 51 and a light chain having an amino acid sequence of SEQ ID NO: 57 (named as "MOR07923"), (iv) a heavy chain having an amino acid sequence of SEQ ID NO: 51 and a light chain having an amino acid sequence of SEQ ID NO: 59 (named as "MOR07924"), (v) a heavy chain having an amino acid sequence of SEQ ID NO: 51 and a light chain having an amino acid sequence of SEQ ID NO: 61 (named as "MOR07925"), (vi) a heavy chain having an amino acid sequence of SEQ ID NO: 51 and a light chain having an amino acid sequence of SEQ ID NO: 63 named as "MOR07926").

In one aspect, the disclosure provides antibodies having an antigen-binding region that can bind specifically to or has a high affinity for one or more regions of target MST1R, having the amino acid sequence of SEQ ID NO: 17. An antibody is said to have a "high affinity" for an antigen if the affinity measurement is at least 100 nM (monovalent affinity of Fab fragment) as a $K_D$. An antibody or antigen-binding region described herein can, for example, bind to MST1R with an affinity of about less than 100 nM, less than about 60 nM, or less than about 30 nM. Further embodiments include antibodies that bind to MST1R with an affinity of less than about 10 nM or less than about 3 nM. In particular, isolated human or humanized antibodies or functional fragments thereof comprising an antigen-binding region that is specific for a partial peptide of MST1R, having an amino acid sequence of SEQ ID NO: 17, where the antibody or functional fragment thereof has an affinity against the partial peptide of MST1R as a $K_D$ of less than about 10 nM, less than about 5 nM, less than about 1 nM, less than about 0.5 nM or less than about 0.1 nM as determined by surface plasmon resonance. While, the affinity against the partial peptide of MST1R as a $K_D$ less than about 10 nM, less than about 5 nM, less than about 1 nM, less than about 0.5 nM or less than 0.1 nM as determined by Solution Equilibrium Titration. For instance, the affinity of an antibody, described herein, against MST1R may be about 0.98 nM or 0.02 nM (monovalent affinity of Fab fragment).

Table 1 provides a summary of affinities of representative antibodies disclosed herein, as determined by surface plasmon resonance (BIACORE) and Solution Equilibrium Titration (SET):

TABLE 1

| Antibody Affinities | | |
|---|---|---|
| Antibody (Fab) | BIACORE (Fab) $K_D$ [nM] | SET (Fab) $K_D$ [nM] |
| MOR07692 | 0.80 | 0.25 |
| MOR07919 | 0.98 | 0.27 |
| MOR07923 | 0.07 | 0.02 |
| MOR07924 | 0.20 | 0.03 |
| MOR07925 | 0.02 | 0.01 |
| MOR07926 | 0.13 | 0.04 |

With reference to Table 1, the affinity of MOR X antibodies was measured by surface plasmon resonance (BIACORE) on immobilized recombinant human MST1R. The BIACORE studies were performed on directly immobilized antigen. The Fab format of MORS X exhibit a monovalent affinity range between about 0.02 and 0.98 nM on immobilized MST1R protein with Fab MOR07925 showing the highest affinity, followed by Fabs MOR07923 and MOR07926. In addition, the Fab format of MORs X exhibit affinity range between about 0.01 and 0.27 nM with Fab MOR07925 showing the highest affinity, followed by Fabs MOR07923 and MOR07924 in SET studies.

Another feature of antibodies described herein is their specificity for an area within the N-terminal region of MST1R. For example, MOR X disclosed herein can bind specifically to the N-terminal region of MST1R.

The type of epitope to which an antibody as described herein binds may be linear (i.e. one consecutive stretch of amino acids) or conformational (i.e. multiple stretches of amino acids). In order to determine whether the epitope of a particular antibody is linear or conformational, the skilled practitioner can analyze the binding of antibodies to overlapping peptides (e.g., 13-mer peptides with an overlap of 11 amino acids) covering different domains of MST1R. ELISA analysis was performed using a recombinant MST1R partial peptide, having the amino acid sequence of SEQ ID NO: 17. Since MOR X was not applicable to immunoblot analysis in order to detect denatured form of the same recombinant MST1R protein, then MOR X must have conformational epitopes within amino acids residues of SEQ ID NO: 17.

An antibody disclosed herein is species cross-reactive with humans and at least one other species, which may be, for example, a monkey or a mouse. An antibody that is cross reactive with at least cynomolgus monkey, for example, can provide greater flexibility and benefits over known anti-target MST1R antibodies, for purposes of conducting in vivo studies in multiple species with the same antibody.

In one embodiment, the described antibody not only is able to bind to MST1R, but also is able to inhibit activation of the MST1R Inhibition of the receptor leads to suppression of intrinsic kinase activity of the receptor and down-regulates signal transduction. Such down regulation can occur for example by limiting ligand binding to MST1R, changing conformation of MST1R, or internalization of MST1R. More specifically, the antibody disclosed herein can mediate its therapeutic effect by MST1R via antibody-effector functions.

Yet another embodiment relates to the inhibition of ligand-dependent MST1R phosphorylation activity of MST1R by antibodies described herein. The disclosed antibody IC50 value of at least 100 ng/ml, at least 50 ng/ml, at least 20 ng/ml, at least 10 ng/ml or at least 5 ng/ml in MSP-dependent MST1R signal transduction assay system such as an "Elk1 luciferase assay".

Another antibody described herein also inhibits ligand-independent MST1R activation A further antibody disclosed herein also inhibits ERK phosphorylation and/or Akt phosphorylation in response to MST1R ligand MSP.

Yet another antibody described herein also suppresses MSP-promoted proliferation of tumor cells that express MST1R.

Peptide Variants

Antibodies described throughout the disclosure are not limited to the specific peptide sequences provided herein. Rather, variants of these polypeptides are also embodied. With reference to the instant disclosure and conventionally available technologies and references, the skilled practitioner will be able to prepare, test and utilize functional variants of the antibodies disclosed herein, while appreciating these variants having the ability to suppress both/either ligand-dependent and/or -independent activation of MST1R fall within the scope of the present invention.

A variant can include, for example, an antibody that has at least one altered complementarity determining region (CDR) (hyper-variable) and/or framework (FR) (variable) domain/position, vis-à-vis a peptide sequence disclosed herein. To better illustrate this concept, a brief description of antibody structure follows.

An antibody is composed of two peptide chains, each containing one (light chain) or three (heavy chain) constant domains and a variable region (VL, VH), the latter of which is in each case made up of four FR regions and three interspaced CDRs. The antigen-binding site is formed by one or more CDRs, yet the FR regions provide the structural framework for the CDRs and, hence, play an important role in antigen binding. By altering one or more amino acid residues in a CDR or FR region, the skilled worker routinely can generate mutated or diversified antibody sequences, which can be screened against the antigen, for new or improved properties, for example.

Figure 2A:
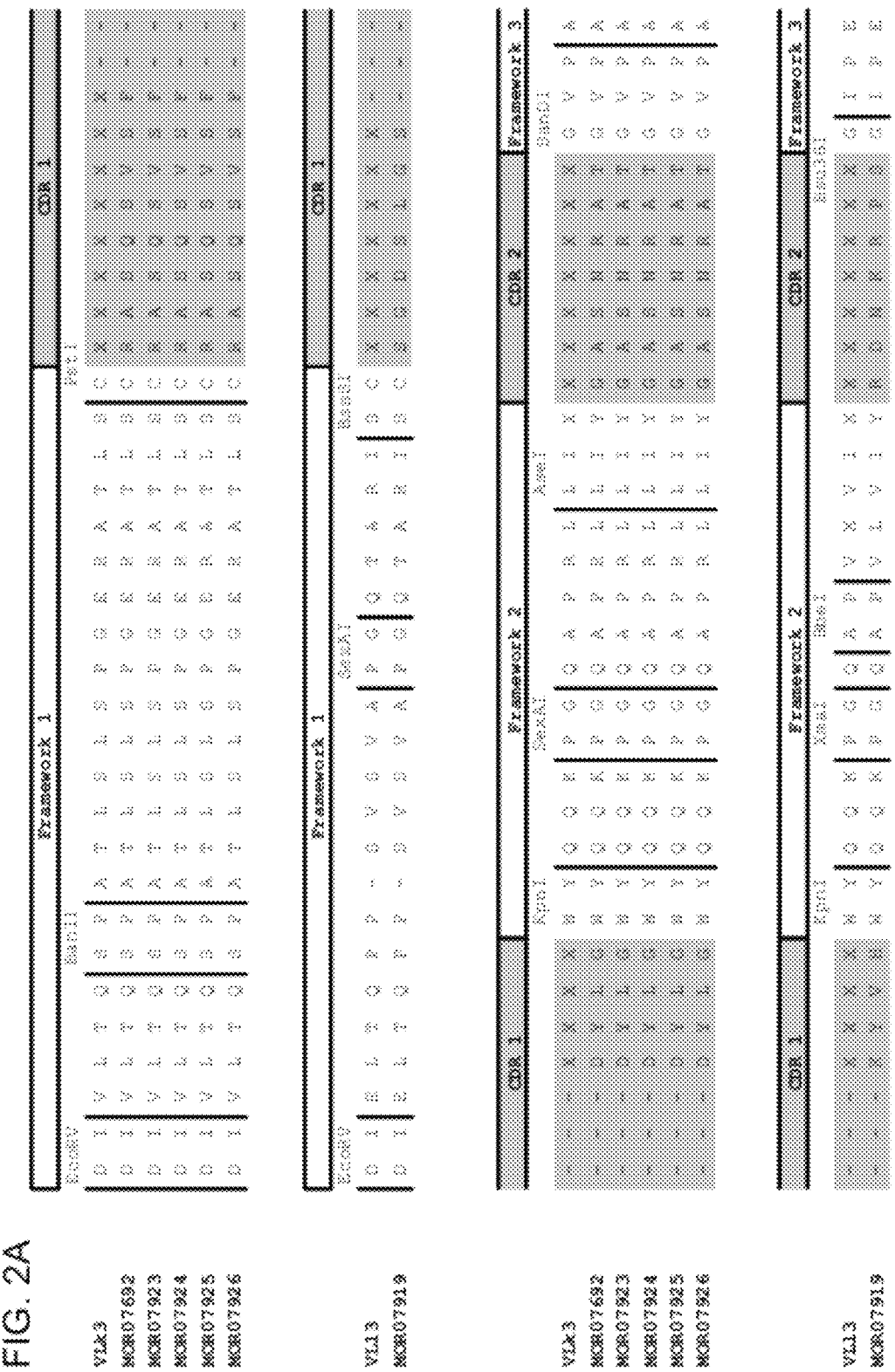
FIG. 2A and FIG. 2B provide amino acid sequences of various novel antibody variable light regions, and which delineates the CDR and framework (FR) regions. The VLκ3 sequence (VLk3; SEQ ID NO: 82) is aligned with the MOR07692 (SEQ ID NO: 23), MOR07923 (SEQ ID NO: 27), MOR07924 (SEQ ID NO: 29), MOR07925 (SEQ ID NO: 31), MOR07926 (SEQ ID NO: 33) variable light region sequences, and the VLλ3 sequence (VL13; SEQ ID NO: 83) is aligned with MOR07919 variable light region sequence (SEQ ID NO: 25).
Figure 2B:
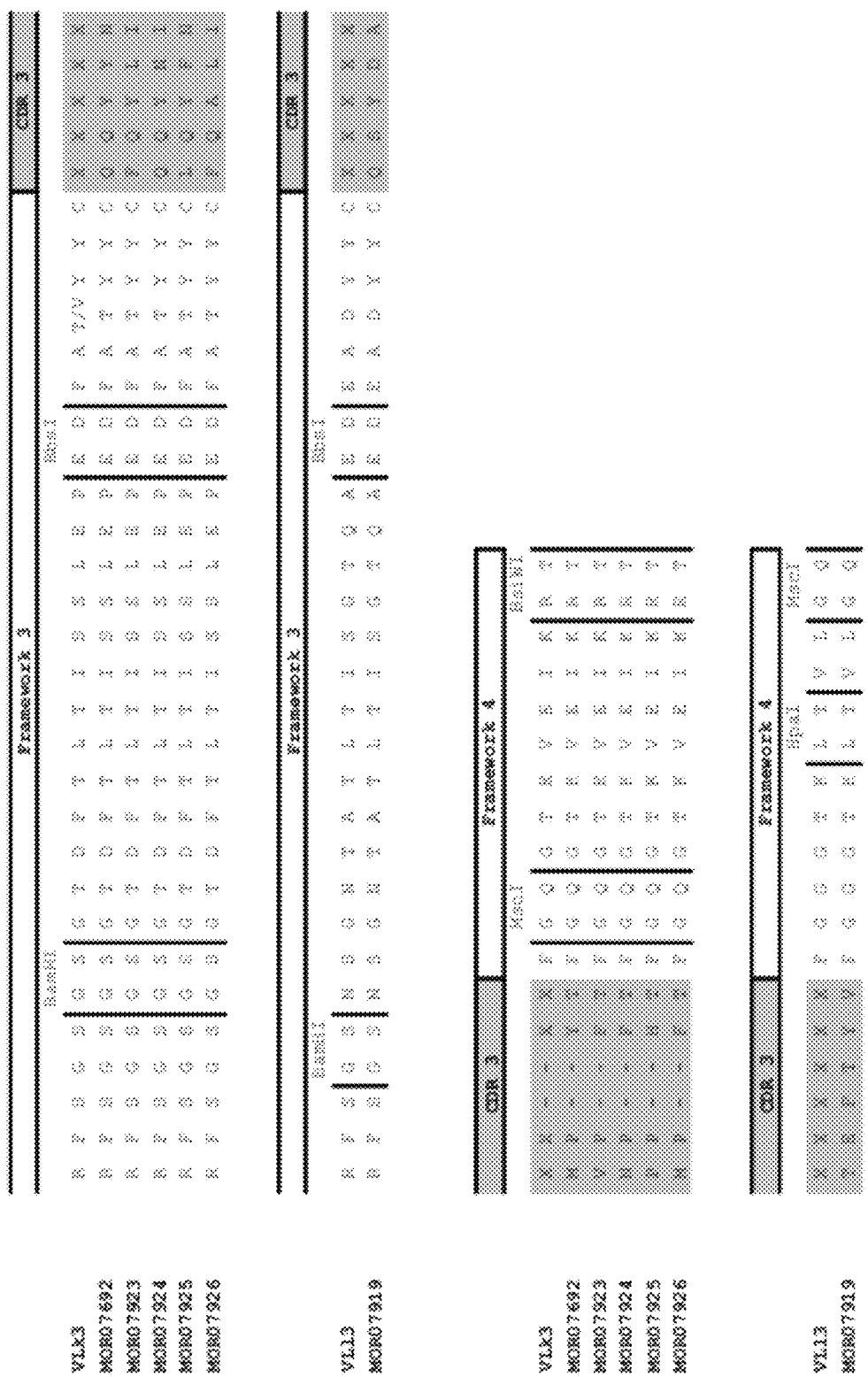

FIG. 1 (VH) and FIG. 2: (VL) delineate the CDR and FR regions (according to Kabat definition) for certain antibodies disclosed herein and compare amino acids at a given position to each other and to corresponding HuCAL "master gene" sequences (as described in U.S. Pat. No. 6,300,064):

The skilled practitioner can use the data in FIG. 1 and FIG. 2 to design peptide variants that are within the scope of the embodiments disclosed herein. In one embodiment, variants are constructed by changing amino acids within one or more CDR regions; a variant might also have one or more altered framework regions. With reference to a comparison of the novel antibodies to each other, candidate residues that can be changed include residues of the variable light and residues of the variable heavy chains of MORs X. Alterations also may be made in the framework regions. For example, a peptide FR domain might be altered where there is a deviation in a residue compared to a germline sequence.

With reference to a comparison of the novel antibodies to the corresponding consensus or "master gene" sequence, candidate residues that can be changed including residues of the variable light chain of MOR X, such as residues of VLλ3 and including residues of the variable heavy chain of MOR X, such as residues of VH3. Alternatively, the skilled worker could make the same analysis by comparing the amino acid sequences disclosed herein to known sequences of the same class of such antibodies, using, for example, the procedure described by Knappik et al. (*J. Mol. Biol.* 296, 57-86, 2000) and U.S. Pat. No. 6,300,064 issued to Knappik et al.

Furthermore, variants may be obtained by using one MOR X as a starting point for optimization by diversifying one or more amino acid residues in the MOR X sequence, preferably amino acid residues in one or more CDRs, and by screening the resulting collection of antibody variants for variants with improved properties. Diversification of one or more amino acid residues in the CDR-3 of VL, the CDR-3 of VH, the CDR-1 of VL and/or the CDR-2 of VH may be accomplished by synthesizing a collection of DNA molecules using trinucleotide mutagenesis (TRIM) technology (Virnekäs, B., Ge, L., Plückthun, A., Schneider, K. C., Wellnhofer, G., and Moroney S. E. (1994) "Trinucleotide phosphoramidites: ideal reagents for the synthesis of mixed oligonucleotides for random mutagenesis." *Nucl. Acids Res.* 22, 5600.).

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled practitioner readily can construct DNAs encoding the conservative amino acid variants.

As used herein, "sequence identity" between two polypeptide sequences, indicates the percentage of amino acids that are identical between the sequences. "Sequence homology" indicates the percentage of amino acids that either is identical or that represents conservative amino acid substitutions. Polypeptide sequences of the invention have a sequence identity in the CDR regions of at least 60%, at least 70% or 80%, at least 90% or at least 95%. Embodied antibodies also have a sequence homology in the CDR regions of at least 80%, at least 90% or at least 95%.

DNA Molecules

The present disclosure also relates to the DNA molecules that encode an antibody described herein. These sequences include, but are not limited to, those DNA molecules set forth in FIGS. 3A, 3B, and 4A to 4F.

DNA molecules of the disclosure are not limited to the sequences disclosed herein, but also include variants thereof. DNA variants within the various embodiments may be described by reference to their physical properties in hybridization. The skilled practitioner will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 (Sambrook, J., E. F. Fritsch, and T. Maniatis (1989) *Molecular Cloning: A laboratory manual*, Cold Spring Harbor Laboratory Press, Cold Spring Harbor, USA) and Ausubel et al., 1995 (Ausubel, F. M., R. Brent, R. E. Kingston, D. D. Moore, J. G. Sedman, J. A. Smith, & K. Struhl. eds. (1995). *Current Protocols in Molecular Biology*. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences. The following relationships are useful in correlating hybridization and relatedness (where $T_m$ is the melting temperature of a nucleic acid duplex):

a. $T_m=69.3+0.41(G+C)$ %
b. The $T_m$ of a duplex DNA decreases by 1° C. with every increase of 1% in the number of mismatched base pairs.
c. $(T_m)_{\mu 2}-(T_m)_{\mu 1}=18.5 \log_{10}\mu 2/\mu 1$ where $\mu 1$ and $\mu 2$ are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

First, in the binding phase, the probe is bound to the target under conditions favoring hybridization. Stringency is usually controlled at this stage by altering the temperature. For high stringency, the temperature is usually between 65° C. and 70° C., unless short (<20 nt) oligonucleotide probes are used. A representative hybridization solution comprises 6×SSC, 0.5% SDS, 5×Denhardt's solution and 100 µg of non-specific carrier DNA. See Ausubel et al., section 2.9, supplement 27 (1994). Of course, many different, yet functionally equivalent, buffer conditions are known. Where the degree of relatedness is lower, a lower temperature may be chosen. Low stringency binding temperatures are between about 25° C. and 40° C. Medium stringency is between at least about 40° C. to less than about 65° C. High stringency is at least about 65° C.

Second, the excess probe is removed by washing. It is at this phase that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS. A high stringency wash solution contains the equivalent (in ionic strength) of less than about 0.2×SSC, with a preferred stringent solution containing about 0.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 60° C.

Accordingly, the present disclosure includes nucleic acid molecules that hybridize to the molecules of set forth in FIGS. 3A, 3B, and 4A to 4F under high stringency binding and washing conditions, where such nucleic molecules encode an antibody or functional fragment thereof having properties as described herein. Embodied molecules (from an mRNA perspective) are those that have at least 75% or 80% (preferably at least 85%, more preferably at least 90% and most preferably at least 95%) homology or sequence identity with one of the DNA molecules described herein. In one particular example of a variant of the disclosure, nucleic acid position 7 in SEQ ID NO: 18 or 20 can be substituted from a C to a G, thereby changing the codon from CAA to GAA.

Functionally Equivalent Variants

Figure 4H:
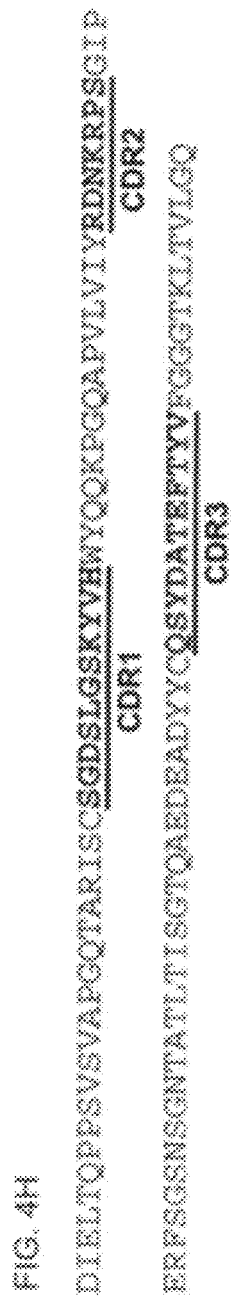
FIG. 4.
FIG. 4A (MOR07692; SEQ ID NO: 22), FIG. 4B (MOR07919; SEQ ID NO: 24), FIG. 4C (MOR07923; SEQ ID NO: 26), FIG. 4D (MOR07924; SEQ ID NO: 28), FIG. 4E (MOR07925; SEQ ID NO: 30) and FIG. 4F (MOR07926; SEQ ID NO: 32) provide nucleic acid sequences of various novel antibody variable light regions.
FIG. 4G (MOR07692; SEQ ID NO: 23), FIG. 4H (MOR07919; SEQ ID NO: 25), FIG. 4I (MOR07923; SEQ ID NO: 27), FIG. 4J (MOR07924; SEQ ID NO: 29), FIG. 4K (MOR07925; SEQ ID NO: 31), and FIG. 4L (MOR07926; SEQ ID NO: 33) provide amino acid sequences of various novel antibody variable light regions. CDR regions L-CDR1, L-CDR2 and L-CDR3 are designated from N- to C-terminus in boldface and underlined.
Figure 41:
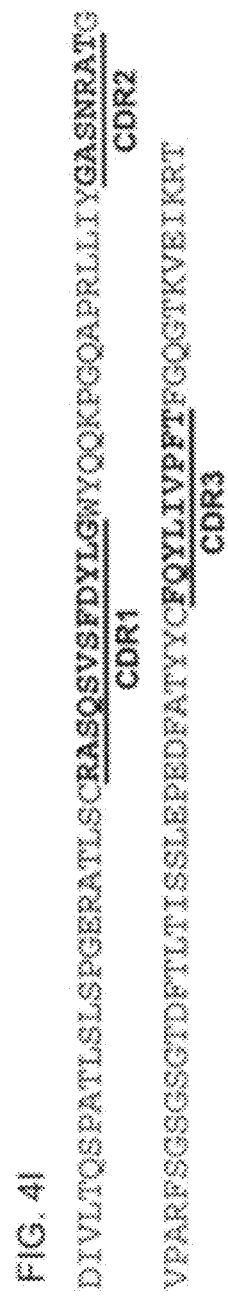

Yet another class of DNA variants within the scope of the invention may be described with reference to the product they encode (see the peptides listed in FIGS. 3C, 3D, and 4G to 4L). These functionally equivalent genes are characterized by the fact that they encode the same peptide sequences found in FIGS. 3C, 3D, and 4G to 4L due to the degeneracy of the genetic code. The amino acid sequence in FIG. 3C is also shown as SEQ ID NO: 19. The amino acid sequence in FIG. 3D is also shown as SEQ ID: NO:21. The amino acid sequence in FIG. 4G is also shown as SEQ ID: NO:23. The amino acid sequence in FIG. 4H is also shown as SEQ ID: NO:25. The amino acid sequence in FIG. 4I is also shown as SEQ ID: NO: 27. The amino acid sequence in FIG. 4J is also shown as SEQ ID: NO: 29. The amino acid sequence in FIG. 4K is also shown as SEQ ID: NO: 31. The amino acid sequence in FIG. 4L is also shown as SEQ ID: NO: 33.

It is recognized that variants of DNA molecules provided herein can be constructed in several different ways. For example, they may be constructed as completely synthetic DNAs. Methods of efficiently synthesizing oligonucleotides in the range of 20 to about 150 nucleotides are widely available. See Ausubel et al., section 2.11, Supplement 21 (1993). Overlapping oligonucleotides may be synthesized and assembled in a fashion first reported by Khorana et al., *J. Mol. Biol.* 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s).

The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present disclosure further provides recombinant DNA constructs comprising one or more of the nucleotide sequences described herein. These recombinant constructs are used in connection with a vector, such as a plasmid, phagemid, phage or viral vector, into which a DNA molecule encoding any disclosed antibody is inserted.

The encoded gene may be produced by techniques described in Sambrook et al., 1989, and Ausubel et al., 1989. Alternatively, the DNA sequences may be chemically synthesized using, for example, synthesizers. See, for example, the techniques described in *Oligonucleotide Synthesis* (1984, Gait, ed., IRL Press, Oxford), which is incorporated by reference herein in its entirety. Recombinant constructs of the disclosure are comprised with expression vectors that are capable of expressing the RNA and/or protein products of the encoded DNA(s). The vector may further comprise regulatory sequences, including a promoter operably linked to the open reading frame (ORF). The vector may further comprise a selectable marker sequence. Specific initiation and bacterial secretory signals also may be required for efficient translation of inserted target gene coding sequences.

The present disclosure further provides host cells containing at least one of the DNAs described herein. The host cell can be virtually any cell for which expression vectors are available. It may be, for example, a higher eukaryotic host cell, such as a mammalian cell, a lower eukaryotic host cell, such as a yeast cell, and may be a prokaryotic cell, such as a bacterial cell. Introduction of the recombinant construct into the host cell can be effected by calcium phosphate transfection, lipofection, DEAE, dextran mediated transfection, electroporation or phage infection.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces,* and *Staphylococcus.*

Bacterial vectors may be, for example, bacteriophage-, plasmid- or phagemid-based. These vectors can contain a selectable marker and bacterial origin of replication derived from commercially available plasmids typically containing elements of the well known cloning vector pBR322 (ATCC Accession No. 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therapeutic Methods

Therapeutic methods involve administering to a subject in need of treatment a therapeutically effective amount of an antibody contemplated by the disclosure. A "therapeutically effective" amount hereby is defined as the amount of an antibody that is of sufficient quantity to deplete MST1R-positive cells in a treated area of a subject—either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, monkey or other lower-order primate).

An antibody of the disclosure might be co-administered with known medicaments, and in some instances the antibody might itself be modified. For example, an antibody could be conjugated to an immunotoxin or a radio labeled antibody to potentially further increase efficacy.

The antibodies described herein can be used as a therapeutic or a diagnostic tool in a variety of situations where MST1R is undesirably expressed or found. Disorders and conditions particularly suitable for treatment with an antibody of the disclosure are MST1R-expressing malignant tumors and neoplasma, for example, breast, lung, colon, bladder, skin, pancreatic, glioma, lymphoma, prostate, thyroid, ovary, gastric, liver, stomach and on the like.

To treat any of the foregoing disorders, pharmaceutical compositions for use in accordance with the present disclosure may be formulated in a conventional manner using one or more physiologically acceptable carriers or excipients. Any antibody described herein can be administered by any suitable means, which can vary, depending on the type of disorder being treated. Possible administration routes include parenteral (e.g., intramuscular, intravenous, intraarterial, intraperitoneal, or subcutaneous), intrapulmonary and intranasal, and, if desired for local immunosuppressive treatment, intralesional administration. In addition, any disclosed antibody may be administered by pulse infusion, with, e.g., declining doses of the antibody. The dosing can be administered by injections, such as for example, intravenous or subcutaneous injections, depending in part on whether the administration is brief or chronic. The amount to be administered will depend on a variety of factors such as the clinical symptoms, weight of the individual, whether other drugs are administered. The skilled practitioner will recognize that the route of administration will vary depending on the disorder or condition to be treated and will understand which route would be most appropriate for the individual based on the specific factors for each individual.

Determining a therapeutically effective amount of the novel polypeptide, according to this invention, largely will depend on particular patient characteristics, route of administration, and the nature of the disorder being treated. General guidance can be found, for example, in the publications of the *International Conference on Harmonisation* and in *Remington's Pharmaceutical Sciences*, chapters 27 and 28, pp. 484-528 (18th ed., Alfonso R. Gennaro, E D., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

Diagnostic Methods

MST1R is highly expressed on cancer cells in certain malignancies; thus, an anti-MST1R antibody of the disclosure may be employed in order to image or visualize a site or location of possible MST1R in a patient. In this regard, an antibody can be detectably labeled, through the use of radioisotopes, affinity labels (such as biotin, avidin, etc.), fluorescent labels, paramagnetic atoms, etc. Procedures for accomplishing such labeling are well known to the art. Clinical applications of antibodies in diagnostic imaging are reviewed by Grossman, H. B., *Urol. Clin. North Amer.* 13:465-474 (1986)), Unger, E. C. et al., *Invest. Radiol.* 20:693-700 (1985)), and Khaw, B. A. et al., *Science* 209:295-297 (1980)).

The detection of foci of such detectably labeled antibodies might be indicative of MST1R, for example. In one embodiment, this examination is done by removing samples of tissue or blood and incubating such samples in the presence of the detectably labeled antibodies. In a one embodiment, this technique is done in a non-invasive manner through the use of magnetic imaging, fluorography, etc. Such a diagnostic test may be employed in monitoring the success of treatment of diseases, where presence or absence of a MST1R-positive cell is a relevant indicator.

Therapeutic and Diagnostic Compositions

The antibodies of the present disclosure can be formulated according to known methods to prepare pharmaceutically useful compositions, where an antibody described herein (including any functional fragment thereof) is combined in a mixture with a pharmaceutically acceptable carrier vehicle. Suitable vehicles and their formulation are described, for example, in *REMINGTON'S PHARMACEUTICAL SCIENCES* (18th ed., Alfonso R. Gennaro, E D., Easton, Pa.: Mack Pub. Co., 1990). In order to form a pharmaceutically acceptable composition suitable for effective administration, such compositions will contain an effective amount of one or more of the antibodies of the present disclosure, together with a suitable amount of carrier vehicle.

Preparations may be suitably formulated to give controlled-release of the active compound. Controlled-release preparations may be achieved through the use of polymers to complex or absorb anti-MST1R antibody. The controlled delivery may be exercised by selecting appropriate macromolecules (for example polyesters, polyamino acids, polyvinyl, pyrrolidone, ethylenevinyl-acetate, methylcellulose, carboxymethylcellulose, or protamine, sulfate) and the concentration of macromolecules as well as the methods of incorporation in order to control release. Another possible method to control the duration of action by controlled release preparations is to incorporate anti-MST1R antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

The compounds may be formulated for parenteral administration by injection, e.g., by bolus injection or continuous infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration. Moreover, the pack or dispenser device and compositions may be presented in a kit for commercial distribution.

The various embodiments of the invention may further be understood by reference to the following working examples, which are intended to illustrate and, hence, not limit the scope of the inventive disclosure.

EXAMPLES

Cell Culture and Transient Transfection

Human embryonic kidney (HEK) 293FreeStyle™ cells were grown in FreeStyle™ 293 Medium (Invitrogen™) 293α was a stable transfectant obtained by transfection with integrinαv and integrinrβ3 expression vectors into HEK293 cells. HEK293 and 293α cells were propagated in DMEM containing 10% FCS. PC3 and T47D were cultured in RPMI containing 10% FCS. For pannings, screenings and functional assays, HEK 293FreeStyle™ cells were transfected with plasmid DNAs using 293fectin™ (Invitrogen™). 293T and 293α cells were transfected with plasmid DNAs using Lipofectamine® 2000 (Invitrogen™) according to the supplier's instructions.

Flow Cytometry ("FACS")

Cells ($5 \times 10^5$ cells/well) were incubated with Fab or IgG antibodies at the indicated concentrations in 50 µl FACS buffer (PBS, 5% FCS) for 60 min at 4° C. in round bottom 96-well culture plates (Corning). Cells were washed twice and then incubated with Fluorescein Isothiocyanate (FITC) conjugated detection antibody for 30 min at 4° C. Cells were washed again, resuspended in 0.3 ml FACS buffer and then analyzed by flow cytometry in a Cytomics FC500 (Beckman Coulter, Inc.). Data were analysed via FlowJo software (Tomy digital biology Co., Ltd.). Polyclonal goat anti-hMSP R IgG (R&D systems) or anti-FLAG M2 antibody (Sigma) was used as a positive control and MOR03207 (anti-lysozyme) antibody was used as a negative control.

Surface Plasmon Resonance

The kinetic constants $K_{on}$ and $k_{off}$ were determined with serial dilutions of the respective Fab binding to covalently immobilized MST1R-Fc fusion protein (R&D systems) using the BIACORE 3000 instrument (BIACORE). For covalent antigen immobilization standard EDC-NHS amine coupling chemistry was used. For direct coupling of MST1R-Fc fusion protein CM5 senor chips (BIACORE) were coated with ~600-700 RU in 10 mM acetate buffer, pH 4.5. For the reference flow cell a respective amount of HSA (human serum albumin) was used. Kinetic measurements were done in PBS (136 mM NaCl, 2.7 mM KCl, 10mM $Na_2HPO_4$, 1.76 mM $KH_2PO_4$ pH 7.4) at a flow rate of 20 µl/min using Fab concentration range from 15.6-500 nM. Injection time for each concentration was 1 min, followed by 3 min dissociation phase. For regeneration 5 µl 10 mM HCl was used. All sensograms were globally fitted using BIA evaluation software 3.2 (BIACORE).

Solution Equilibrium Titration (SET)

Affinity determination in solution was basically performed as described in the literature (Friguet, B., Chaffotte, A. F., Djavadi-Ohaniance, L., and Goldberg, M. E. (1985) *J Immunol Methods* 77, 305-319.). In order to improve the sensitivity and accuracy of the SET method, the method was modified from classical ELISA to ECL based technology (Haenel, C., Satzger, M., Ducata, D. D., Ostendorp, R., and Brocks, B. (2005) *Anal Biochem* 339, 182-184).

Example 1

Antibody Generation from HuCAL Libraries

For the generation of therapeutic antibodies against MST1R, selections with the MorphoSys HuCAL GOLD phage display library were carried out. HuCAL GOLD® is a Fab library based on the HuCAL® concept (Knappik et al. (*J. Mol. Biol.*, 296, 57-86, 2000); Krebs et al., *J. Immunol. Methods*, 254, 67-84, 2001; Rothe et al., *J. Mol. Biol.*, 376(4): 1182-200, 2008), in which all six CDRs are diversified, and which employs the CysDisplay™ technology for linking Fab fragments to the phage surface (WO 01/05950).

A. Phagemid Rescue, Phage Amplification and Purification

HuCAL GOLD® phagemid library was amplified in 2×YT medium containing 34 µg/ml chloramphenicol and 1% glucose (2×YT-CG). After helper phage infection (VCSM13) at an $OD_{600\,nm}$ of 0.5 (30 min at 37° C. without shaking; 30 min at 37° C. shaking at 250 rpm), cells were spun down (4120 g; 5 min; 4° C.), resuspended in 2×YT/34 µg/ml chloramphenicol/50 µg/ml kanamycin/0.25 mM IPTG and grown overnight at 22° C. Phages were PEG-precipitated from the supernatant, resuspended in PBS/20% glycerol and stored at −80° C. Phage amplification between two panning rounds was conducted as follows: mid-log phase TG1 cells were infected with eluted phages and plated onto LB-agar supplemented with 1% of glucose and 34 µg/ml of chloramphenicol (LB-CG). After overnight incubation at 30° C., colonies were scraped off, and used to inoculate 2xYT-CG until an $OD_{600\,nm}$ of 0.5 was reached and VCSM13 helper phages added for infection as described above.

B. Pannings with HuCAL GOLD®

For the selections HuCAL GOLD antibody-phages were divided into six pools comprising different combinations of VH master genes (pool 1: VH1/3/5κ, pool 2: VH1/3/5λ, pool 3: VH2/4/6κ, pool 4: VH2/4/6λ, pool 5: VH1-6κ, pool 6: VH1-6λ). These pools were individually subjected to 3 rounds of whole cell panning on MST1R expression vector-transfected HEK 293FreeStyle™ cells followed by pH-elution and a post-adsorption step on MST1R-negative HEK 293FreeStyle™ cells for depletion of irrelevant antibody-phages. Finally, the remaining antibody phages were used to infect *E. coli* TG1 cells which were then plated on agar plates and incubated overnight at 30° C. The next day, the bacterial colonies were scraped off the plates, phages were rescued and amplified as described above. The second and the third round of selections were performed as the initial one. In addition to standard pannings, the LCDR3-RapMAT®technology was applied to potentially identify clones with higher affinities. RapMAT® represents a built-in affinity maturation process for the rapid selection of high affinity antibodies. This technology is based on the modular design of the HuCAL GOLD® Fab library. For the RapMAT® method two rounds of standard panning were performed with separate pools of lambda and kappa libraries. The selected 2nd round Fab pools were diversified via exchange of the LCDR3 with LCDR3 library cassettes. The resulting Fab libraries were subjected to two further rounds of pannings under stringent conditions.

C. Subcloning and Expression of Soluble Fab Fragments

The Fab encoding inserts of the selected HuCAL GOLD® phagemids were subcloned into the expression vector pMORPH® x9_Fab_FS (Rauchenberger et al., *J. Biol. Chem.* 278(40):38194-205, 2003) to facilitate rapid expression of soluble Fab. For this purpose, the Fab encoding insert (ompA-VLCL and phoA-Fd) of the selected clones was cut out of the plasmid DNA with XbaI and EcoRI, and cloned into the XbaI/EcoRI cut vector pMORPH® x9_FS. Fabs expressed in this vector carry two C-terminal tags (FLAG™ and Strep-tag® II) for detection and purification.

D. Expression of HuCAL GOLD Fab Antibodies in *E. coli* and Purification

Expression of Fab fragments encoded by pMORPH® x9_Fab_FS in *E. coli* TG-1 cells was carried out in shaker flask cultures using 750 ml of 2×YT medium supplemented with 34 µg/ml chloramphenicol. Cultures were shaken at 30° C. until the OD600 nm reached 0.5. Expression was induced by addition of 0.75 mM IPTG for 20 hr at 30° C. Bacteria were harvested by centrifugation and the periplasmic fraction prepared using 30-35 ml BBS. Fabs were purified via Strep-tag® II using Step-Tactin sepharose columns. Purity of the samples was analyzed together with calibration standards by SDS-PAGE in denatured, reduced state and by size exclusion chromatography (SEC) in native state. Protein concentrations were determined by UV-spectrophotometry (Krebs et al., *J. Immunol. Methods* 254, 67-84, 2001).

Example 2

Cloning, Expression and Purification of HuCAL® IgG1

In order to express full length IgG1, variable domain fragments of heavy (VH) and light chains (VL) were subcloned from Fab expression vector into pMORPH®2_hIg vectors. Restriction enzymes MfeI and BlpI were used for subcloning of VH fragments. Restriction enzymes EcoRV and BsiWI or HpaI were used for subcloning of VL kappa or VL lambda fragments, respectively. After digestion, VH and VL fragments were isolated from preparative agarose gel and ligated into the respective IgG expression vectors (VH fragment into pMORPH® 2_h_IgG1f; Vkappa fragment into pMORPH® 2_h_Igκ; Vlambda fragment into pMORPH® 2_h_Igλ2). The resulting IgG expression plasmids were characterized by restriction analysis and sequencing. Transient expression of full length human IgG was performed in HKB11 cells, which were transfected with IgG heavy and light chain expression vectors. IgGs were purified from cell culture supernatants by affinity chromatography via Protein A Sepharose column. Further down stream processing included a buffer exchange by gel filtration and sterile filtration of purified IgG. Quality control revealed a purity of >90% by reducing SDS-PAGE and >90% monomeric IgG as determined by analytical size exclusion chromatography.

Example 3

Elisa Screening of HuCAL® Fab Clones and HuCAL® IgG1

Wells of a 384-well MaxiSorp™ microtiter plate were coated with 0.5 µg/ml recombinant MST1R-Fc fusion protein diluted in PBS. The plate was incubated overnight at 4° C. Next day, the wells were washed 3 times with PBST (0.05% Tween20 in PBS) and then blocked with MPBST (5% milk powder in PBST) for 30 min at room temperature on a microtiter plate shaker. The wells were washed 3 times with PBST before adding the primary antibody, i.e. preblocked BEL extracts of HuCAL® Fab clones or purified HuCAL® antibodies and control antibodies. The plate was incubated for 2 hr at room temperature on a microtiter plate shaker and then washed 3 times with PBST. For detection of HuCAL® antibodies, goat anti-human IgG alkaline phosphatase (Dianova, diluted 1:5,000 in 0.5% milkpowder in PBST) was added and the plate incubated for 1 h at room temperature on a microtiter plate shaker. Subsequently, the plate was washed 5 times with TBST (0.05% Tween20 in TBS). Attophos (AttoPhos Substrate Set, Roche) was added (diluted 1:10 in TBS) and fluorescence was measured in a TECAN microtiter plate reader (emission: 535 nm, excitation: 430 nm).

Example 4

Cross-Reactivity Analysis by FACs

Figure 10:
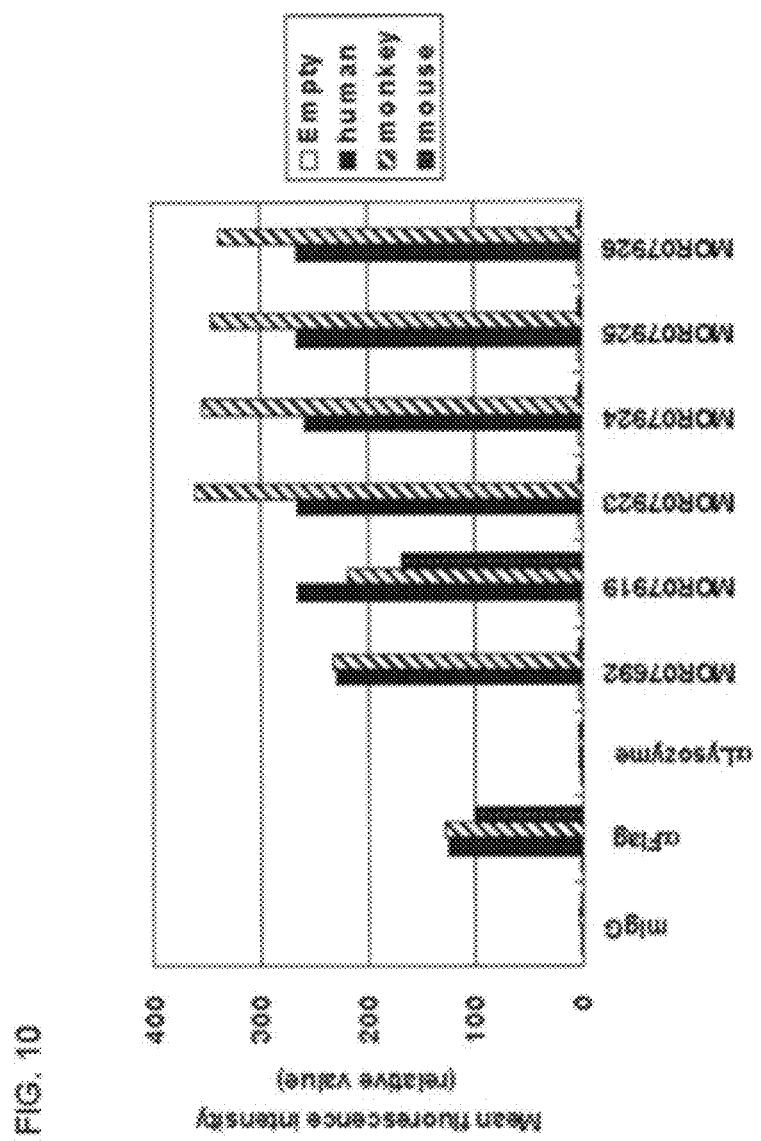
FIG. 10 provides a FACS analysis demonstrating crossreactivity of isolated antibodies (MorphoSys IgG1-2 µg/ml) to MST1R orthologs.

FACS-analysis of MST1R ortholog-expressing cells: Human MST1R (cDNA nucleotide sequence is shown as GenBank® Accession No: NM_002447.2), cynomolgus monkey MST1R and mouse MST1R (cDNA nucleotide sequence is shown as GenBank® Accession No: NM_009074.1) expression vector containing N-terminal Flag tag (pFLAG-myc-CMV-19, Sigma) were constructed. cDNA encoding cynomolgus monkey MST1R was amplified by PCR using cynomolgus monkey stomach cDNA as a template with forward and reverse primers having nucleotide sequences of SEQ ID NO: 34 and 35, respectively. By sequencing analysis of PCR product, the cynomolgus MST1R ORF nucleotide sequence was identified as shown in SEQ ID NO: 36. The corresponding amino acid sequence was shown in SEQ ID NO: 37. Then human, cynomolgus monkey and mouse MST1R ORF cDNA, excluding signal peptide regions, were amplified using respective forward and reverse primers having nucleotide sequences of SEQ ID NO: 38 and 39 (human), 40 and 41 (cynomolgus monkey), and 42 and 43 (mouse) with appropriate cloning sites and then cloned into pFLAG-myc-CMV-19. An amplified human MST1R fragment encodes amino acids corresponding to GenBank® Accession No: NP_002438.2 (SEQ ID NO: 45). A Mouse MST1R fragment encodes amino acids corresponding to GenBank® Accession No: NP_033100.1 (SEQ ID NO: 47) except for those amino acid differences at positions: 688 (Leu to Pro), 713 (Ile to Val), 714 (Ala to Gly) and 719 (Ala to Val). These expression vectors were transfected into HEK293T cells. For FACS-analysis, cells were incubated with 2 µg/ml primary antibodies followed by incubation with FITC-labeled secondary antibody as described above. In FIG. 10, anti-Flag antibody confirmed expression of each (human, cynomolgus monkey and mouse MST1R) protein. MOR07692, MOR07923, MOR07924, MOR07925 and MOR07926 showed binding to both human and monkey MST1R. On the other hand, MOR07919 also exhibited binding to mouse MST1R besides human and monkey MST1R.

The nucleotide sequence of these antibodies was decided by DNA sequencer. The nucleotide sequence of variable heavy chain of MOR07692, MOR07923, MOR07924, MOR07925 and MOR07926 was decided as shown in FIG. 3A and SEQ ID NO: 18. The nucleotide sequence of variable heavy chain of MOR07919 is shown in FIG. 3B and SEQ ID NO: 20. The amino acid sequence of variable heavy chain of MOR07692, MOR07923, MOR07924, MOR07925 and MOR07926 was decided as shown in FIG. 3C and SEQ ID NO: 19. The amino acid sequence of variable heavy chain of MOR07919 is shown in FIG. 3D and SEQ ID NO: 21.

The nucleotide sequence of variable light chain of MOR07692 is shown in FIG. 4A and SEQ ID NO: 22. The amino acid sequence of variable light chain of MOR07692 is shown in FIG. 4G and SEQ ID NO: 23. The nucleotide sequence of variable light chain of MOR07919 is shown in FIG. 4B and SEQ ID NO: 24. The amino acid sequence of variable light chain of MOR07919 is shown in FIG. 4H and SEQ ID NO: 25. The nucleotide sequence of variable light chain of MOR07923 is shown in FIG. 4C and SEQ ID NO: 26. The amino acid sequence of variable light chain of MOR07923 is shown in FIG. 4I and SEQ ID NO: 27. The nucleotide sequence of variable light chain of MOR07924 is shown in FIG. 4D and SEQ ID NO: 28. The amino acid sequence of variable light chain of MOR07924 is shown in FIG. 4J and SEQ ID NO: 29. The nucleotide sequence of variable light chain of MOR07925 is shown in FIG. 4E and SEQ ID NO: 30. The amino acid sequence of variable light chain of MOR07925 is shown in FIG. 4K and SEQ ID NO: 31. The nucleotide sequence of variable light chain of MOR07926 is shown in FIG. 4F and SEQ ID NO: 32. The amino acid sequence of variable light chain of MOR07926 is shown in FIG. 4L and SEQ ID NO: 33.

The amino acid sequence of variable heavy chain CDR3 (H-CDR3) of MOR07692, MOR07923, MOR07924, MOR07925 and MOR07926 is shown in SEQ ID NO: 1. The amino acid sequence of variable heavy chain CDR3 (H-CDR3) of MOR07919 is shown in SEQ ID NO: 4.

The amino acid sequence of variable heavy chain CDR2 (H-CDR2) of MOR07692, MOR07923, MOR07924, MOR07925 and MOR07926 is shown in SEQ ID NO: 2. The amino acid sequence of variable heavy chain CDR2 (H-CDR2) of MOR07919 is shown in SEQ ID NO: 5.

The amino acid sequence of variable heavy chain CDR1 (H-CDR1) of MOR07692, MOR07923, MOR07924, MOR07925 and MOR07926 is shown in SEQ ID NO: 3. The amino acid sequence of variable heavy chain CDR1 (H-CDR1) of MOR07919 is shown in SEQ ID NO: 6.

The amino acid sequence of variable light chain CDR3 (L-CDR3) of MOR07692, is shown in SEQ ID NO: 7. The amino acid sequence of variable light chain CDR3 (L-CDR3) of MOR07919 is shown in SEQ ID NO: 8. The amino acid sequence of variable light chain CDR3 (L-CDR3) of MOR07923 is shown in SEQ ID NO: 9. The amino acid sequence of variable light chain CDR3 (L-CDR3) of MOR07924 is shown in SEQ ID NO: 10. The amino acid sequence of variable light chain CDR3 (L-CDR3) of MOR07925 is shown in SEQ ID NO: 11 The amino acid sequence of variable light chain CDR3 (L-CDR3) of MOR07926 is shown in SEQ ID NO: 12.

The amino acid sequence of variable light chain CDR2 (L-CDR2) of MOR07692, MOR07923, MOR07924, MOR07925 and MOR07926 is shown in SEQ ID NO: 14. The amino acid sequence of variable light chain CDR2 (L-CDR2) of MOR07919 is shown in SEQ ID NO: 16.

The amino acid sequence of variable light chain CDR1 (L-CDR1) of MOR07692, MOR07923, MOR07924, MOR07925 and MOR07926 is shown in SEQ ID NO: 13. The amino acid sequence of variable light chain CDR1 (L-CDR1) of MOR07919 is shown in SEQ ID NO: 15.

The nucleotide sequence of heavy chain of MOR07692 is shown in SEQ ID: NO: 50. The amino acid sequence of heavy chain of MOR07692 is shown in SEQ ID NO: 51. The nucleotide sequence of light chain of MOR07692 is shown in SEQ ID: NO: 54. The amino acid sequence of light chain of MOR07692 is shown in SEQ ID NO: 55.

The nucleotide sequence of heavy chain of MOR07923 is shown in SEQ ID: NO: 50. The amino acid sequence of heavy chain of MOR07923 is shown in SEQ ID NO: 51. The nucleotide sequence of light chain of MOR07923 is shown in SEQ ID: NO: 56. The amino acid sequence of light chain of MOR07923 is shown in SEQ ID NO: 57.

The nucleotide sequence of heavy chain of MOR07924 is shown in SEQ ID: NO: 50. The amino acid sequence of heavy chain of MOR07924 is shown in SEQ ID NO: 51. The nucleotide sequence of light chain of MOR07924 is shown in SEQ ID: NO: 58. The amino acid sequence of light chain of MOR07924 is shown in SEQ ID NO: 59.

The nucleotide sequence of heavy chain of MOR07925 is shown in SEQ ID: NO: 50. The amino acid sequence of heavy chain of MOR07925 is shown in SEQ ID NO: 51. The nucleotide sequence of light chain of MOR07925 is shown in SEQ ID: NO: 60. The amino acid sequence of light chain of MOR07925 is shown in SEQ ID NO: 61.

The nucleotide sequence of heavy chain of MOR07926 is shown in SEQ ID: NO: 50. The amino acid sequence of heavy chain of MOR07926 is shown in SEQ ID NO: 51. The nucleotide sequence of light chain of MOR07926 is shown in SEQ ID: NO: 62. The amino acid sequence of light chain of MOR07926 is shown in SEQ ID NO: 63

The nucleotide sequence of heavy chain of MOR07919 is shown in SEQ ID: NO: 48. The amino acid sequence of heavy chain of MOR07919 is shown in SEQ ID NO: 49. The nucleotide sequence of light chain of MOR07919 is shown in SEQ ID: NO: 52. The amino acid sequence of light chain of MOR07919 is shown in SEQ ID NO: 53.

Example 5

Binding Activity Analysis by ELISA

Figure 11:
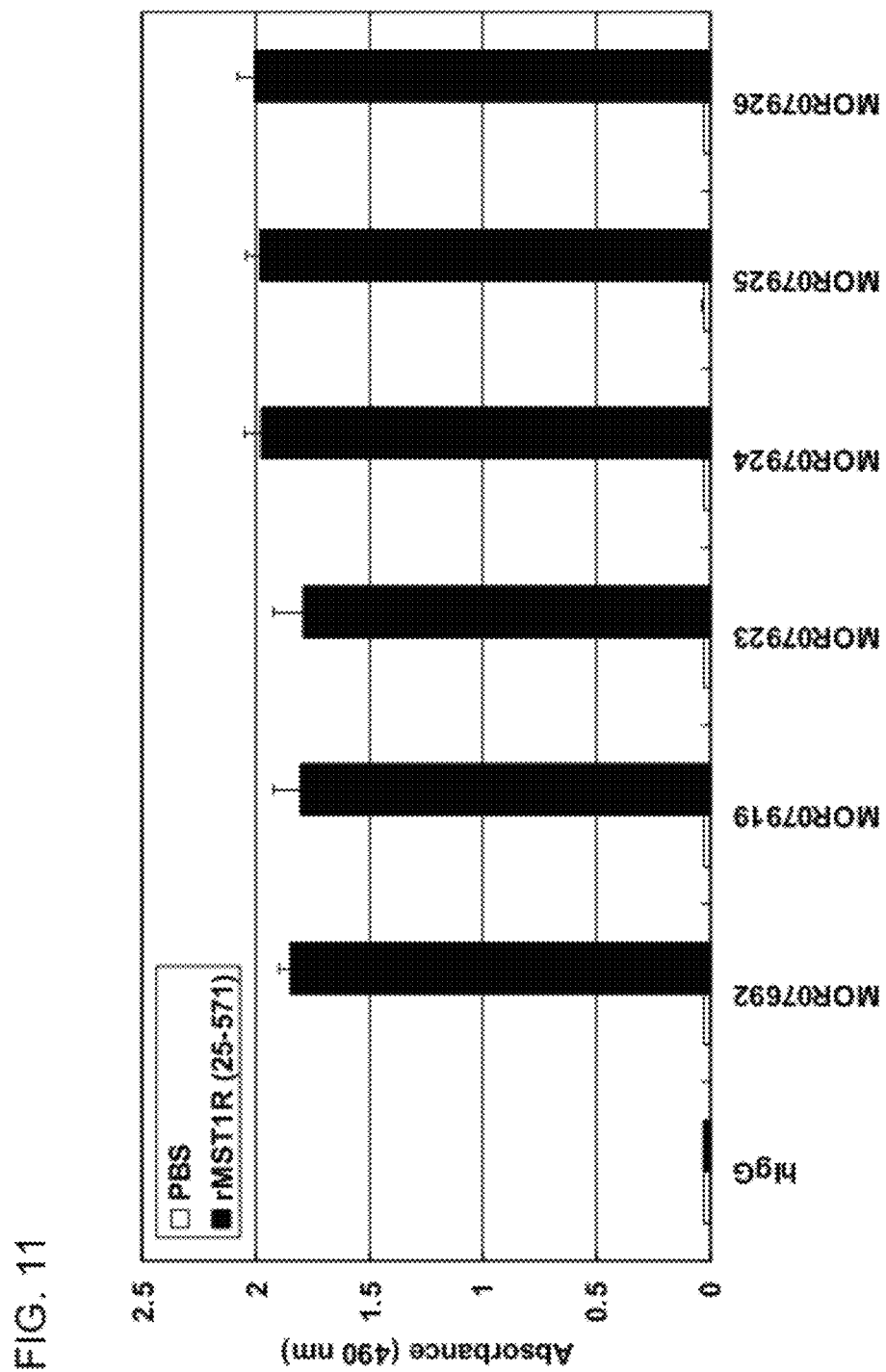
FIG. 11 shows binding activity of MOR07692, MOR07919, MOR07923, MOR07924, MOR07925 and MOR07926 to the 25-571 portion of human MST1R compared to PBS control. Using the t-test analysis for n=3, the p values are as follows: MOR07692: 4.56E–07; MOR07919: 1.43E–05; MOR07923: 2.10E–05; MOR07924: 1.42E–06; MOR07925: 9.74E–07; and MOR07926: 1.53E–06.

Wells of a 96-well MaxiSorp™ microtiter plate were coated with 1 μg/ml recombinant MST1R-Fc fusion protein (containing 25-571 amino acid sequence of human MST1R, R&D) diluted in PBS. The plate was incubated overnight at 4° C. Next day, the wells were washed once with PBS-FCS buffer (5% FCS in PBS) and then blocked with PBS-FCS buffer for 1 hr at room temperature. After removal of the PBS-FCS buffer 4 μg/ml primary antibody was added to the MST1R-Fc coated wells and incubated for 1 hr at room temperature. After washing once with PBS-FCS buffer, the secondary antibody was added and allowed to incubate for 1 hr at room temperature. After washing 3 times with PBS-FCS buffer, substrate of HRP (0.4 mg/ml o-Phenylenediamine Dihydrochloride and 0.006% Hydrogen peroxide in substrate buffer (50 mM tri-sodium citrate dehydrate, 100 mM di-sodium Hydrorogen Phosphate, pH4.5)) was added. After yellow color developed, 1 M HCl was further added to stop reaction. Absorbance at 490 nm was measured in EnVision microtiter plate reader. In FIG. 11, all of the obtained antibodies (MOR07692, MOR07919, MOR07923, MOR07924, MOR07925 and MOR07926) showed binding to 25-571 portion of human MST1R. Each antibody was applicable for immunoprecipitation of non-reduced and non-denatured MST1R, but not for Western blotting to detect reduced and denatured MST1R (data not shown). It indicates that these antibodies recognize native conformation within amino acids residues in SEQ ID NO: 17.

Example 6

Biological Assays

A. Elk1 Luciferase Reporter Gene Assay

Figure 12:
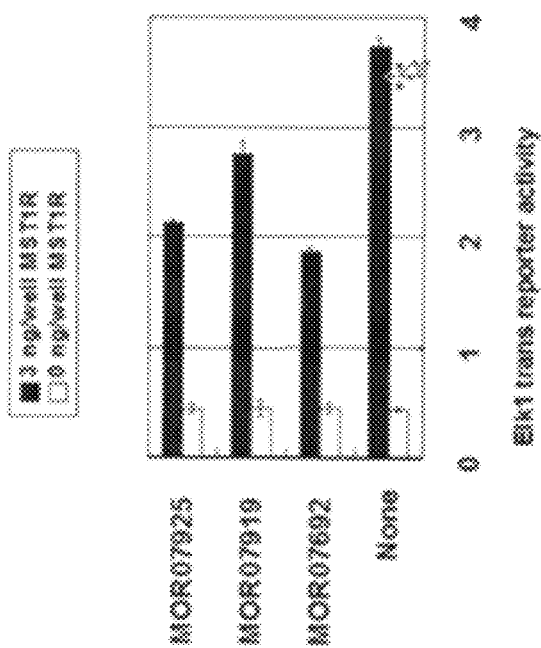
FIG. 12 shows inhibitory Elk1 trans reporter activity in the absence of ligand. Using the t-test analysis and an antibody concentration of 5 µg/ml, the p values are as follows: MOR07692: 5.39E–06; MOR07919: 3.19E–04; and MOR07925: 3.78E–05.

Functionality of antibodies was tested via Elk1 luciferase reporter gene assay. The principle of the assay is based on the co-transfection of 293α cells with several vectors. MST1R is integrated into the cell membrane and becomes activated (phosphorylated) to transduce signal to ERK (extracellullar signal-regulated kinase) when it is overexpressed or stimulated with MSP. To test functionality of antibodies, Elk1 luciferase reporter gene assay was established as follows: First we constructed pFR-Luc2CP vector. To construct pFR-Luc2CP, pFR-Luc vector (Stratagene) was digested with HindIII, treated with T4 DNA polymerase for blunting, and digested with BamHI to obtain about 140 bp fragment containing the 5×GAL4 binding element and TATA box. pGL4.12[luc2CP] (Promega) was digested with EcoICRI/BglII, dephosphorylated, and ligated with the above fragment to generate pFR-Luc2CP. Then, 293α cells were transiently co-transfectd with pcDNA-DEST40 MST1R, pcDNA-DEST40, pFA2-Elk1 (Stratagene), pFR-Luc2CP and pGL4.74 [hRluc/TK] (Promega) using a Lipofectamine 2000 (Invitrogen) transfection procedure and seeded onto white 96-well cell culture plates. The next day after transfection, the cells were preincubated with the antibodies for 1 hr and then the ligand (human MSP) was added to the wells. After 6 hr incubation, cell lysates were prepared and the firefly luciferase activity (specific signal) and the *Renilla* luciferase activity (signal for normalization) were measured using the Dual-luciferase reporter assay system (Promega). The firefly/*Renilla* ratio was calculated to normalize the data of each well. Table 2 shows $IC_{50}$ values in the presence of 100 ng/ml MSP ligand. MOR07692, MOR07919, MOR07923, MOR07924, MOR07925 and MOR07926 showed low $IC_{50}$ value ranging between 4 and 100 ng/ml. As shown in FIG. 12, overexpression of MST1R by itself induced ligand-independent activation of MST1R. MOR07925, MOR07919 and MOR07692 also suppressed this type of activation of MST1R.

TABLE 2

| $IC_{50}$ value of Elk1 luciferase reporter gene assay | |
|---|---|
| Clone ID | Reporter assay IC50 (ng/ml) |
| MOR07692 | 4.4 |
| MOR07919 | 87.6 |
| MOR07923 | 9 |
| MOR07924 | 15.7 |
| MOR07925 | 5.9 |
| MOR07926 | 11.4 |

B. ELISA for Detection of Phosphorylation of MST1R

Figure 13:
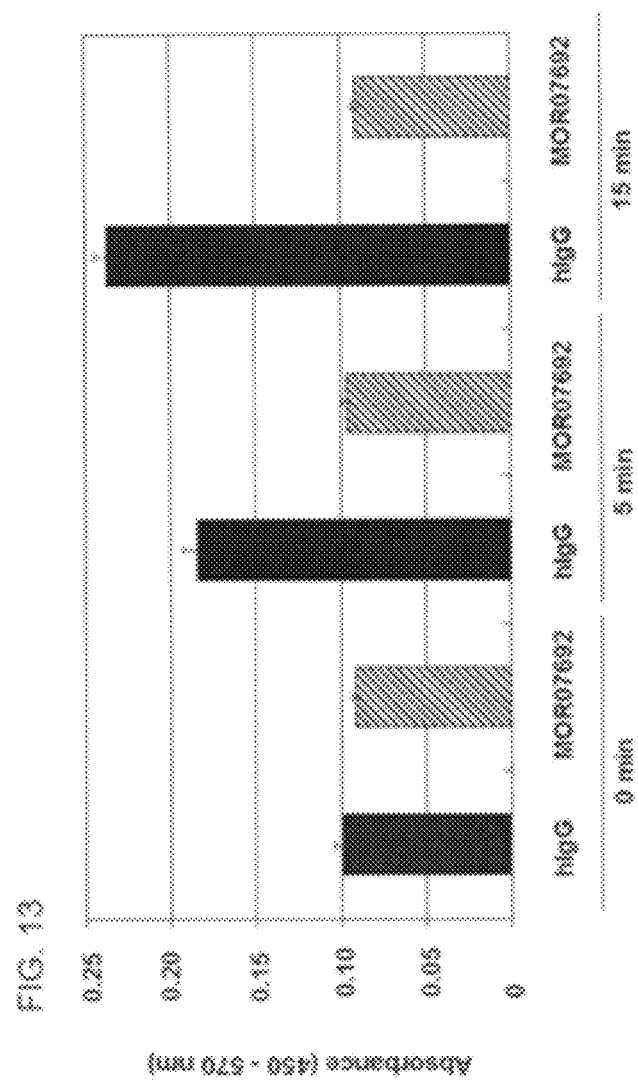
FIG. 13 shows inhibition of 200 ng/ml MSP-induced phosphorylation by MOR07692 compared to hIgG control at various time points (min) at an absorbance of 450 nm with a 570 nm reference) At the 5 min time point, the p value is 5.43E–05, while at the 15 min time point, the p value is 4.76E–06.

The change in phosphorylation status of MST1R after treatment with ligand and/or antibody was determined by ELISA system. After overnight incubation of PC3 cells ($1 \times 10^6$) on 6 cm-diameter dishes, cells were washed with PBS, and incubated with 0.1% BSA-RPMI medium. After overnight incubation, cells were treated with 1 μg/ml MOR07692 antibody for 1 hr at 37° C., and then stimulated with 200 ng/ml of recombinant MSP (R&D systems) for 0 min to 15 min. Then cell lysates were prepared and phosphorylated forms of MST1R were measured by Human Phospho-MSP R/Ron ELISA system (R&D systems) according to the supplier's instruction. MOR07692 showed complete inhibition of MST1R phosphorylation promoted by addition of MSP ligand as shown in FIG. 13.

C. Western Blotting for Activated ERK

Figure 14:
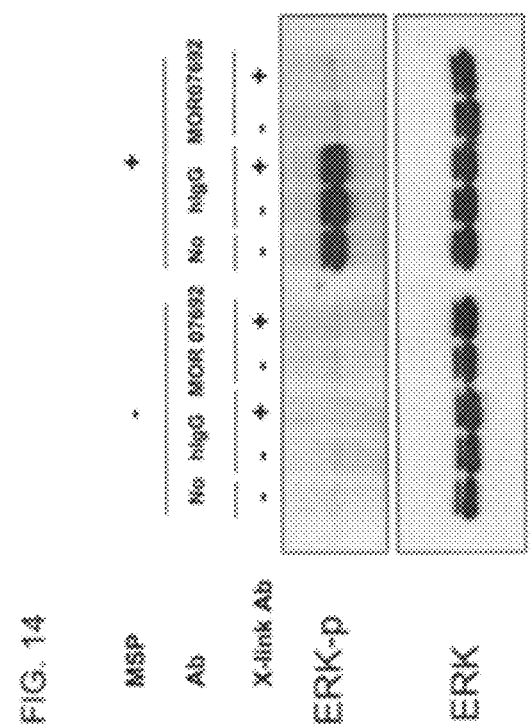
FIG. 14 is a western blot illustrating inhibition of 100 ng/ml MSP-induced phosphorylation of ERK by 1 µg/ml MOR07692 compared to no antibody and hIgG controls in the presence or absence of 1 µg/ml cross-linked antibody.

The change in phosphorylation status of ERK after treatment with ligand and/or antibody was determined by Western blotting. After overnight cultivation of PC3 cells ($2 \times 10^5$) on 12 wells plate, cells were washed with PBS, and incubated with 0.1% BSA-RPMI medium. After overnight incubation, cells were treated with 1 μg/ml MOR07692 antibody with or without 1 μg/ml goat affinity purified antibody to human IgG-Fc (Cappel) for 1 hr at 37° C. After the incubation, 100 ng/ml of recombinant MSP (R&D systems) was added, and further incubated for 30 min. Then cells were lysed with RIPA buffer containing complete mini (Roche) and phosphatase inhibitor (Nakarai tesque). Lysates were cleared from cellular debris by centrifugation, and protein concentrations were determined using BCA protein assay (PIERCE). Lysates were resuspended in buffer containing β-mercaproethanol and denatured at 99° C. for 5 minutes. Protein (10 μg/lane) was resolved by SDS-PAGE on 5-20% gels. Proteins were blotted onto PVDF membrane (BioRad). Membranes were blocked with Blockace (Yukijirushi), for 1 hr at room temperature and incubated overnight at 4° C. with polyclonal antibodies against ERK or phospho-ERK antibody. After washing, membranes were incubated with secondary anti-rabbit horseradish peroxidase-conjugated antibody (Amersham). Immunoreactive bands were visualized on X-ray films using ECL plus substrate (GE Healthcare). FIG. 14 represented ERK phosphorylation in response to ligand MSP. The increase was almost completely inhibited by the addition of MOR07692 in the presence and absence of cross link antibody to human IgG-Fc.

D. Cell Proliferation Assay

Figure 15:
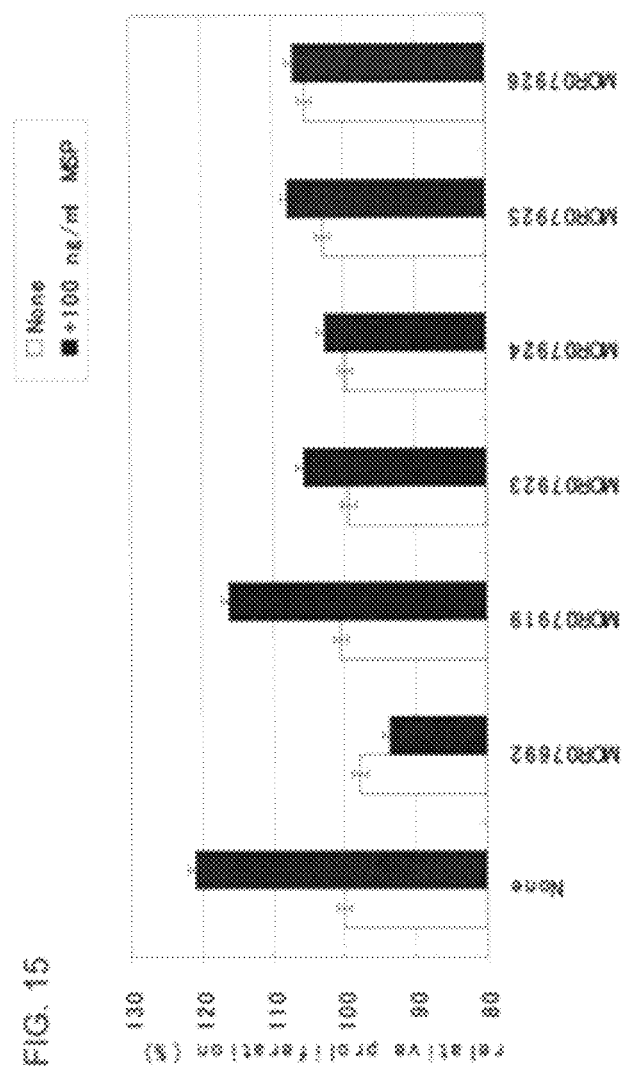
FIG. 15 shows inhibitory activity of the specified antibodies or without antibody control on MSP-induced cell proliferation (%) in the presence or absence of 100 ng/ml MSP. For the various antibodies, the p values are as follows: MOR07692: 0.0001; MOR07919: 0.2037; MOR07923: 0.0106; MOR07924: 0.0203; MOR07925: 0.0042; and MOR07926: 0.0044.

T-47D cells (5000 cells/well) suspended in RPMI medium containing 2% charcoal/dextran-treated FCS (Hyclone) were seeded onto 96-well plates. Cells were incubated with 1 μg/ml antibodies for 1 hr at 37° C., and then stimulated with 100 ng/ml recombinant MSP. After 5 days incubation, cellular ATP was measured by CellTiter-Glo luminescent cell viability assay kit (Promega), according to the supplier's instruction. As shown in FIG. 15, MOR07692, MOR07923, MOR07924, MOR07925 and MOR07926 clearly suppressed MSP-promoted proliferation of T-47D cells. MOR07919 had a weaker inhibitory activity than other antibodies.

E. Migration Assay

Figure 16:
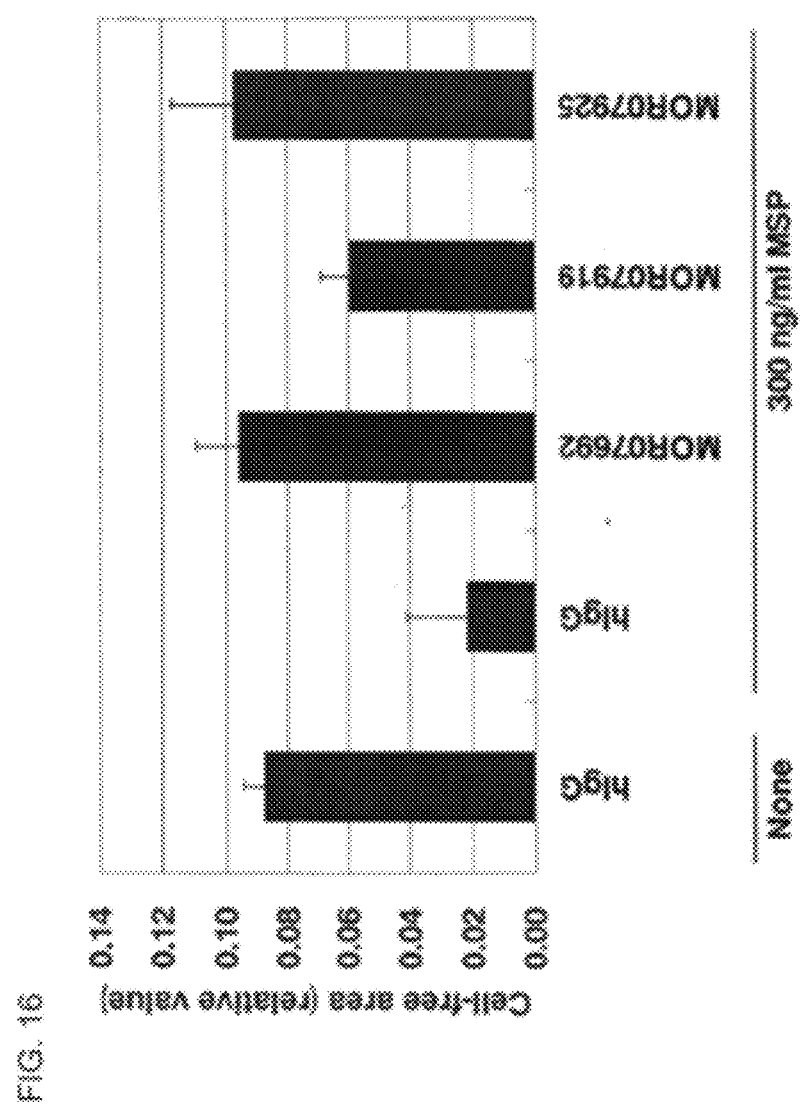
FIG. 16 shows inhibition of MSP-induced migration by indicated anti-MST1R antibodies.

BxPC-3 cells ($5 \times 10^4$ cells/well) suspended in RPMI medium containing 10% FCS were seeded onto 96-well Oris™ Cell Migration Assay plates (Platypus Technologies, LLC.). After overnight cultivation, the stoppers were removed from test wells and medium was replaced with 2% charcoal/dextran-treated FCS (Hyclone). Cells were incubated with 10 μg/ml antibodies for 1 hr at 37° C., and then stimulated with 300 ng/ml recombinant MSP. After 24 hr incubation, migrated cells were observed using bright field microscopy (Nikon) and then their images were analyzed by Image J software to calculate cell-free area. As shown in FIG. 16, MOR07919, MOR07692 and MOR07925 clearly suppressed MSP-promoted cell migration of BxPC-3 cells. MOR07692 and MOR07925 had stronger inhibitory activity compared to MOR07919.

F. Internalization Assay

Figure 17:
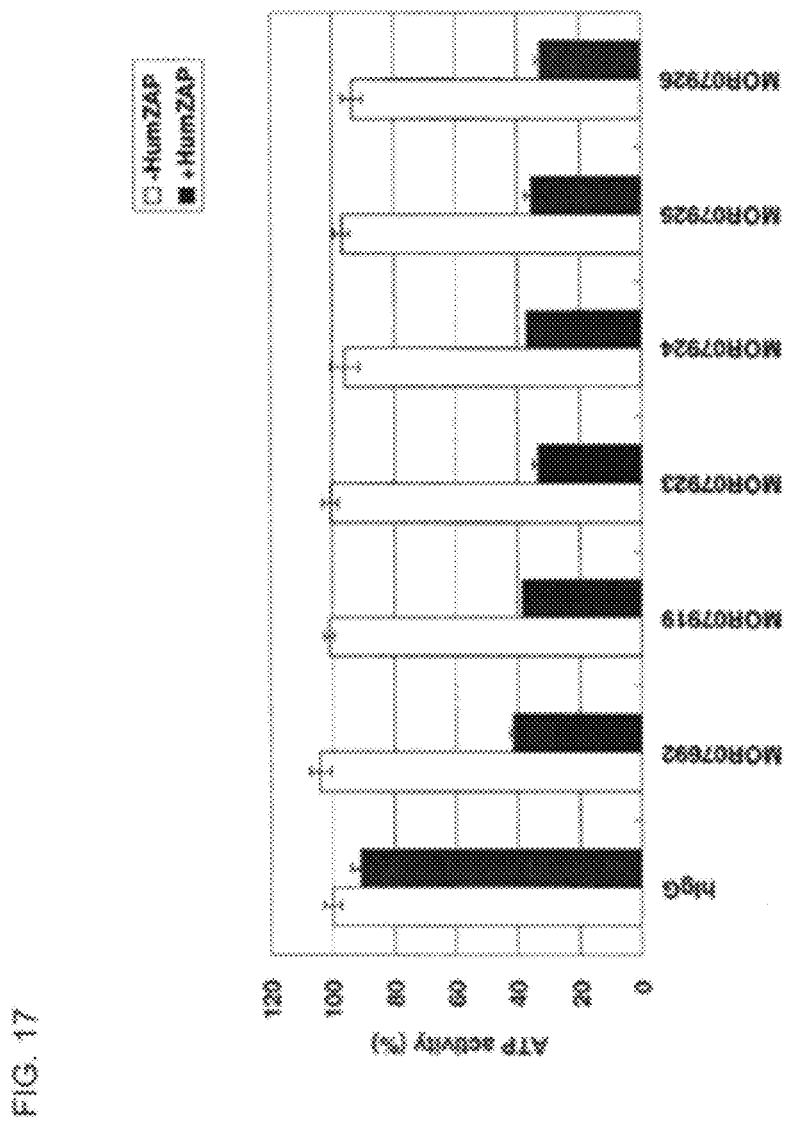
FIG. 17 shows potential of indicted anti-MST1R antibodies to induce internalization.

In order to evaluate the ability of antibodies to internalize, Hum-ZAP secondary conjugate (affinity-purified goat anti-human IgG-saporin provided by ADVANCED TARGETING SYSTEMS) was used as the secondary antibody to cause protein synthesis inhibition and, ultimately, cell death after internalization into cells. PC3 cells (2000 cells/well) suspended in RPMI medium containing 10% FCS were seeded onto 96-well flat clear bottom white culture plates. The next day, the cells were preincubated with antibodies for 1 hr at 4° C. After removal of the medium containing the antibodies, 0.5 μg/ml Hum-ZAP secondary conjugate was added to the wells. The plates were incubated for 1 hr at 4° C. and then for 3 days at 37° C. The cellular ATP was measured as readout for cell viability by CellTiter-Glo luminescent cell viability assay kit (Promega), according to the supplier's instruction. As shown in FIG. 17, viability of PC3 cells was greatly reduced by the treatment with MOR07692, MOR07919, MOR07923, MOR07924, MOR07925 and MOR07926, suggesting the potential of these antibodies to internalize.

The contents of all patents, patent applications, published PCT applications and articles, books, references, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

The invention claimed is:

1. An antibody or functional fragment thereof comprising an antigen-binding region that is specific for a partial peptide of MST1R having an amino acid sequence of SEQ ID NO: 17, wherein the antigen-binding region comprises:
  a heavy chain variable domain comprising:
    (a) a H-CDR1 comprising SEQ ID NO: 3;
    (b) a H-CDR2 comprising SEQ ID NO: 2; and
    (c) a H-CDR3 comprising SEQ ID NO: 1; and
  a light chain variable domain comprising:
    (a) a L-CDR1 comprising SEQ ID NO: 13;
    (b) a L-CDR2 comprising SEQ ID NO: 14; and
    (c) a L-CDR3 comprising an amino acid sequence selected from the group consisting of SEQ ID NOs: 7 and 9-12.

2. The antibody or functional fragment thereof according to claim 1, wherein said antibody or functional fragment thereof inhibits ligand-dependent and independent phosphorylation of MST1R.

3. The antibody or functional fragment thereof according to claim 1, wherein said antibody or functional fragment thereof inhibits ligand-dependent and independent phosphorylation of MST1R, in addition to inhibiting phosphorylation of ERK.

4. The antibody or functional fragment thereof according to claim 1, wherein said antibody or functional fragment thereof has an affinity against said partial peptide of MST1R as a $K_D$ of less than about 10 nM as determined by surface plasmon resonance.

5. The antibody or functional fragment thereof according to claim 1, wherein said antibody or functional fragment thereof has an affinity against said partial peptide of MST1R as a $K_D$ less than about 10 nM as determined by Solution Equilibrium Titration.

6. The antibody or functional fragment thereof according to claim 1, wherein said antibody or functional fragment thereof suppresses MSP-promoted cell proliferation of tumor cells that express MST1R.

7. The antibody or functional fragment thereof according to claim 1, wherein said antibody or functional fragment thereof suppresses MSP-promoted cell migration of tumor cells that express MST1R.

8. The antibody or functional fragment thereof according to claim 1, wherein said antibody or functional fragment thereof internalizes MST1R.

9. The antibody or functional fragment thereof according to claim 1, wherein said antibody or functional fragment thereof is cross-reactive with human MST1R and cynomolqus monkey MST1R.

10. The antibody or functional fragment thereof according to claim 1, wherein said antibody is an IgG.

11. The antibody or functional fragment thereof according to claim 10, wherein said antibody is an IgG1.

12. The antibody or functional fragment thereof according to claim 1, wherein the antibody or functional fragment thereof comprises a variable heavy chain of SEQ ID NO: 19.

13. The antibody or functional fragment thereof according to claim 1, wherein the antibody or functional fragment thereof comprises a variable light chain having the amino acid sequence of SEQ ID NO: 23, 27, 29, 31 or 33.

14. The antibody or functional fragment thereof according to claim 1, wherein the antigen-binding region comprises a heavy chain comprising an amino acid sequence selected from the group consisting of:
  (i) SEQ ID NO: 51; and
  (ii) a sequence having at least 80 percent sequence identity to SEQ ID NO: 51 and which still comprises a heavy chain variable domain comprising:
    (a) a H-CDR1 comprising SEQ ID NO: 3;
    (b) a H-CDR2 comprising SEQ ID NO: 2; and
    (c) a H-CDR3 comprising SEQ ID NO: 1.

15. The antibody or functional fragment thereof according to claim 1, wherein the antigen-binding region comprises a light chain comprising an amino acid sequence selected from the group consisting of:
  (i) SEQ ID NOs: 55, 57, 59, 61 and 63; and
  (ii) a sequence having at least 80 percent sequence identity to any of SEQ ID NOs: 55, 57, 59, 61 and 63 and still comprises a light chain variable domain comprising:
    (a) a L-CDR1 comprising SEQ ID NO: 13;
    (b) a L-CDR2 comprising SEQ ID NO: 14; and
    (c) a L-CDR3 comprising an amino acid sequence selected from the group consisting of SEQ ID NOs: 7 and 9-12.

16. The antibody or functional fragment thereof according to claim 14 or 15, wherein the antibody or functional fragment thereof comprises a heavy chain having the amino acid sequence of SEQ ID NO: 51 and a light chain having the amino acid sequence of SEQ ID NO: 55.

17. The antibody or functional fragment thereof according to claim 14 or 15, wherein the antibody or functional fragment thereof comprises a heavy chain having the amino acid sequence of SEQ ID NO: 51 and a light chain having the amino acid sequence of SEQ ID NO: 57.

18. The antibody or functional fragment thereof according to claim 14 or 15, wherein the antibody or functional fragment thereof comprises a heavy chain having the amino acid sequence of SEQ ID NO: 51 and a light chain having the amino acid sequence of SEQ ID NO: 59.

19. The antibody or functional fragment thereof according to claim 14 or 15, wherein the antibody or functional fragment thereof comprises a heavy chain having the amino acid sequence of SEQ ID NO: 51 and a light chain having the amino acid sequence of SEQ ID NO: 61.

20. The antibody or functional fragment thereof according to claim 14 or 15, wherein the antibody or functional fragment thereof comprises a heavy chain having the amino acid sequence of SEQ ID NO: 51 and a light chain having the amino acid sequence of SEQ ID NO: 63.

21. The functional fragment according to claim 1, which is a Fab, or the antibody according to claim 1, which is a scFv antibody.

22. A variable heavy chain of an antibody or functional fragment thereof that specifically binds to a partial peptide of MST1R comprising SEQ ID NO: 17, wherein said variable heavy chain comprises:
  (a) a H-CDR1 comprising SEQ ID NO: 3;
  (b) a H-CDR2 comprising SEQ ID NO: 2; and
  (c) a H-CDR3 comprising SEQ ID NO: 1 and is encoded by
    (i) a nucleic acid sequence comprising SEQ ID NO: 18, or
    (ii) a nucleic acid sequence having at least 80 percent sequence identity to SEQ ID NO: 18.

23. A variable light chain of an antibody or functional fragment thereof that specifically binds to a partial peptide of MST1R comprising SEQ ID NO: 17, wherein said variable light chain comprises:
  (a) a L-CDR1 comprising SEQ ID NO: 13;
  (b) a L-CDR2 comprising SEQ ID NO: 14; and
  (c) a L-CDR3 comprising an amino acid sequence selected from the group consisting of SEQ ID NOs: 7 and 9-12 and is encoded by (i) a nucleic acid sequence comprising a sequence selected from the group consisting of SEQ ID NOs: 22, 26, 28, 30 and 32, or (ii) a nucleic acid sequence having at least 80 percent sequence identity to a sequence selected from the group consisting of SEQ ID NOs: 22, 26, 28, 30 and 32.

24. A nucleic acid that encodes the antibody or functional fragment of claim 1.

25. A nucleic acid encoding a variable heavy chain of an antibody or functional fragment thereof that specifically binds to a partial peptide of MST1R comprising SEQ ID NO: 17, wherein said variable heavy chain comprises:
   (a) a H-CDR1 comprising SEQ ID NO: 3;
   (b) a H-CDR2 comprising SEQ ID NO: 2; and
   (c) a H-CDR3 comprising SEQ ID NO: 1, comprising
   (i) the sequence of SEQ ID NO: 18 or
   (ii) a nucleic acid sequence having at least 80 percent sequence identity to SEQ ID NO: 18.

26. A nucleic acid encoding a variable light chain of an antibody or functional fragment thereof that specifically binds to a partial peptide of MST1R comprising SEQ ID NO: 17, wherein said variable light chain comprises:
   (a) a L-CDR1 comprising SEQ ID NO: 13;
   (b) a L-CDR2 comprising SEQ ID NO: 14; and
   (c) a L-CDR3 comprising an amino acid sequence selected from the group consisting of SEQ ID NOs: 7 and 9-12, comprising
   (i) a sequence selected from the group consisting of SEQ ID NOs: 22, 26, 28, 30 and 32 or
   (ii) a nucleic acid sequence having at least 80 percent sequence identity to a sequence selected from the group consisting of SEQ ID NOs: 22, 26, 28, 30 and 32.

27. A vector comprising the nucleic acid sequence according to claim 24.

28. An isolated cell comprising the vector according to claim 27.

29. The cell according to claim 28, wherein said cell is bacterial.

30. The cell according to claim 28, wherein said cell is mammalian.

31. A pharmaceutical composition comprising an antibody or functional fragment thereof according to claim 1, and a pharmaceutically acceptable carrier or excipient thereof.

32. The antibody or functional fragment thereof according to claim 1, wherein the antibody is a synthetic human antibody.

33. A method for producing an antibody or functional fragment thereof comprising an antigen-binding region that is specific for a partial peptide of MST1R having an amino acid sequence of SEQ ID NO: 17 comprising:
   (a) culturing a cell that has been transformed with the vector of claim 27;
   (b) harvesting the cell; and
   (c) disrupting the cell to obtain a crude extract containing the antibody or functional fragment thereof.

34. A method for producing an antibody or functional fragment thereof comprising an antigen-binding region that is specific for a partial peptide of MST1R having an amino acid sequence of SEQ ID NO: 17 comprising:
   (a) culturing the cell of claim 28;
   (b) harvesting the cell; and
   (c) disrupting the cell to obtain a crude extract containing the antibody or functional fragment thereof.

35. The antibody or functional fragment thereof according to claim 1, wherein the heavy chain variable domain comprises:
   (a) a H-CDR1 comprising SEQ ID NO: 3;
   (b) a H-CDR2 comprising SEQ ID NO: 2; and
   (c) a H-CDR3 comprising SEQ ID NO: 1; and the light chain variable domain comprises:
   (a) a L-CDR1 comprising SEQ ID NO: 13;
   (b) a L-CDR2 comprising SEQ ID NO: 14; and
   (c) a L-CDR3 comprising SEQ ID NO: 7.

36. The antibody or functional fragment thereof according to claim 1, wherein the heavy chain variable domain comprises:
   (a) a H-CDR1 comprising SEQ ID NO: 3;
   (b) a H-CDR2 comprising SEQ ID NO: 2; and
   (c) a H-CDR3 comprising SEQ ID NO: 1; and the light chain variable domain comprises:
   (a) a L-CDR1 comprising SEQ ID NO: 13;
   (b) a L-CDR2 comprising SEQ ID NO: 14; and
   (c) a L-CDR3 comprising SEQ ID NO: 9.

37. The antibody or functional fragment thereof according to claim 1, wherein the heavy chain variable domain comprises:
   (a) a H-CDR1 comprising SEQ ID NO:3;
   (b) a H-CDR2 comprising SEQ ID NO: 2; and
   (c) a H-CDR3 comprising SEQ ID NO: 1; and the light chain variable domain comprises:
   (a) a L-CDR1 comprising SEQ ID NO: 13;
   (b) a L-CDR2 comprising SEQ ID NO: 14; and
   (c) a L-CDR3 comprising SEQ ID NO: 10.

38. The antibody or functional fragment thereof according to claim 1, wherein the heavy chain variable domain comprises:
   (a) a H-CDR1 comprising SEQ ID NO: 3;
   (b) a H-CDR2 comprising SEQ ID NO: 2; and
   (c) a H-CDR3 comprising SEQ ID NO: 1; and the light chain variable domain comprises:
   (a) a L-CDR1 comprising SEQ ID NO: 13;
   (b) a L-CDR2 comprising SEQ ID NO: 14; and
   (c) a L-CDR3 comprising SEQ ID NO: 11.

39. The antibody or functional fragment thereof according to claim 1, wherein the heavy chain variable domain comprises:
   (a) a H-CDR1 comprising SEQ ID NO: 3;
   (b) a H-CDR2 comprising SEQ ID NO: 2; and
   (c) a H-CDR3 comprising SEQ ID NO: 1; and the light chain variable domain comprises:
   (a) a L-CDR1 comprising SEQ ID NO: 13;
   (b) a L-CDR2 comprising SEQ ID NO: 14; and
   (c) a L-CDR3 comprising SEQ ID NO: 12.

* * * * *